United States Patent
Choi et al.

(10) Patent No.: US 10,461,256 B2
(45) Date of Patent: *Oct. 29, 2019

(54) COMPOUND AND PHOTOELECTRIC DEVICE, IMAGE SENSOR AND ELECTRONIC DEVICE INCLUDING THE SAME

(71) Applicant: Samsung Electronics Co., Ltd., Suwon-si, Gyeonggi-do (KR)

(72) Inventors: Yeong Suk Choi, Suwon-si (KR); Ohkyu Kwon, Seoul (KR); Youn Hee Lim, Hwaseong-si (KR); Hyesung Choi, Seoul (KR); Moon Gyu Han, Suwon-si (KR); Hiromasa Shibuya, Seongnam-si (KR); Yong Wan Jin, Seoul (KR); Katsunori Shibata, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,901

(22) Filed: Jun. 2, 2017

(65) Prior Publication Data
US 2017/0352811 A1  Dec. 7, 2017

(30) Foreign Application Priority Data

Jun. 3, 2016 (KR) .................. 10-2016-0069805
Jun. 1, 2017 (KR) .................. 10-2017-0068530

(51) Int. Cl.
| | |
|---|---|
| *H01L 51/00* | (2006.01) |
| *C07F 7/08* | (2006.01) |
| *H01L 27/30* | (2006.01) |
| *C07D 471/14* | (2006.01) |
| *C07D 471/04* | (2006.01) |
| *C07D 421/14* | (2006.01) |
| *C07D 421/04* | (2006.01) |
| *C07D 495/04* | (2006.01) |

(52) U.S. Cl.
CPC ........ *H01L 51/0053* (2013.01); *C07D 421/04* (2013.01); *C07D 421/14* (2013.01); *C07D 471/04* (2013.01); *C07D 471/14* (2013.01); *C07D 495/04* (2013.01); *C07F 7/0816* (2013.01); *H01L 51/0062* (2013.01); *H01L 51/0071* (2013.01); *H01L 51/0072* (2013.01); *H01L 51/0074* (2013.01); *H01L 51/0094* (2013.01); *H01L 27/307* (2013.01)

(58) Field of Classification Search
None
See application file for complete search history.

(56) References Cited

U.S. PATENT DOCUMENTS

| | | |
|---|---|---|
| 2011/0074491 A1 | 3/2011 | Yofu et al. |
| 2013/0299799 A1 | 11/2013 | Yofu et al. |
| 2016/0111651 A1 | 4/2016 | Yun et al. |
| 2016/0126470 A1 | 5/2016 | Ro et al. |
| 2016/0149132 A1 | 5/2016 | Lim et al. |
| 2017/0062726 A1 | 3/2017 | Choi et al. |
| 2017/0213973 A1 | 7/2017 | Yun et al. |

FOREIGN PATENT DOCUMENTS

| | | |
|---|---|---|
| EP | 2317582 A1 | 5/2011 |
| EP | 3018723 A1 | 5/2016 |
| EP | 3026722 A1 | 6/2016 |
| KR | 2017/0027223 A | 3/2017 |

OTHER PUBLICATIONS

Bulliard, et al. "Dipolar donor-acceptor molecules in the cyanine limit for high efficiency green-light-selective organic photodiodes," Journal of Materials Chemistry C., vol. 4, pp. 1117-1125 (2016).
Heichert, et al. "Synthesis and characterization of long wavelength-absorbing donor/acceptor-substituted methane dyes," Zeitschrift for Naturforschung—Section B, Journal of Chemical Sciences, vol. 71, No. 6, pp. 2-9 (2016).
Matsumoto, et al. "Utilization of Carboxylated 1, 3-Indandione as an Electron Acceptor in Dye-Sensitized Solar Cells," Bulletin of the Chemical Society of Japan, vol. 85, No. 12, pp. 1329-1331 (2012).
Extended European Search Report dated Nov. 2, 2017 issued in corresponding European Patent Application No. 17174434.5.

*Primary Examiner* — Tanisha Diggs
(74) *Attorney, Agent, or Firm* — Harness, Dickey & Pierce, P.L.C.

(57) ABSTRACT

A compound represented by Chemical Formula 1, and a photoelectric device, an image sensor, and an electronic device including the same are disclosed.

[Chemical Formula 1]

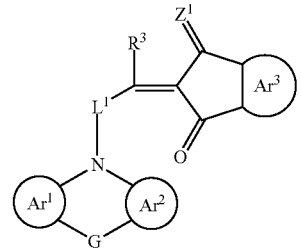

In Chemical Formula 1, each substituent is the same as defined in the detailed description.

34 Claims, 12 Drawing Sheets

COMPOUND AND PHOTOELECTRIC DEVICE, IMAGE SENSOR AND ELECTRONIC DEVICE INCLUDING THE SAME

CROSS-REFERENCE TO RELATED APPLICATION

This application claims priority under 35 U.S.C. § 119 to Korean Patent Application Nos. 10-2016-0069805, filed in the Korean Intellectual Property Office on Jun. 3, 2016, and 10-2017-0068530, filed in the Korean Intellectual Property Office on Jun. 1, 2017, the entire contents of each of which are incorporated herein by reference.

BACKGROUND

1. Field

Example embodiments relate to compound and a photoelectric device, an image sensor, and/or an electronic device including the same.

2. Description of Related Art

A photoelectric device converts light into an electrical signal using photoelectric effects, it may include a photodiode, a phototransistor, and the like, and it may be applied to an image sensor, a solar cell, an organic light emitting diode, and the like.

An image sensor including a photodiode may have high resolution and thus a small pixel. At present, a silicon photodiode is widely used, but it has a problem of deteriorated sensitivity since it has a small absorption area due to small pixels. Accordingly, an organic material that is capable of replacing silicon has been researched.

An organic material has a high extinction coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound having improved light absorption efficiency in a green wavelength region, an absorption intensity, and heat resistance.

Example embodiments also provide a photoelectric device capable of selectively absorbing light in a green wavelength region and improving efficiency.

Example embodiments also provide an image sensor including the photoelectric device.

Example embodiments also provide an electronic device including the image sensor.

According to example embodiments, a compound represented by Chemical Formula 1 is provided.

[Chemical Formula 1]

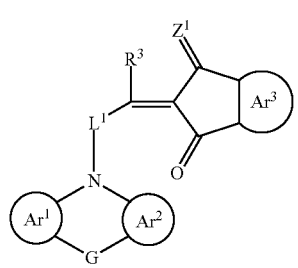

In Chemical Formula 1, $Ar^1$ to $Ar^3$ independently may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^3$ may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G may be one of a single bond, —O—, —S—, —Se—, —N=, —$(CR^fR^g)_k$—, —$NR^h$—, —$SiR^iR^j$—, —$GeR^kR^l$—, —$(C(R^m)=C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, $R^k$ and $R^l$, $R^m$ and $R^n$, and $R^o$ and $R^p$ independently may be present or linked with each other to provide a ring, and k may be one of 1 and 2, $Z^1$ may be one of O or $CR^bR^c$, wherein $R^b$ and $R^c$ independently may be one of hydrogen, a substituted or unsubstituted C1 to C10 alkyl group, a cyano group, and a cyano-containing group, provided that at least one of $R^b$ and $R^c$ may be a cyano group or a cyano-containing group, and $L^1$ may be one of linking groups of Group 1,

[Group 1]

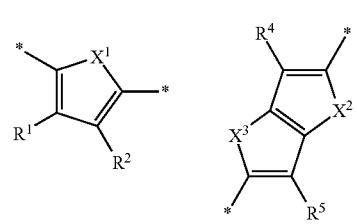

wherein, in Group 1, $X^1$ may be one of —Se—, —Te—, —O—, —S(=O)—, —$S(=O)_2$—, —$SiR^bR^c$—, and —$GeR^dR^e$—, $X^2$ and $X^3$ are the same or different and independently may be one of —S—, —Se—, —Te—, —O—, —S(=O)—, —$S(=O)_2$—, —$NR^a$—, —$SiR^bR^c$—, and —$GeR^dR^e$—, $R^a$ to $R^e$ are the same or different and independently may be one of hydrogen and a substituted or unsubstituted C1 to C10 alkyl group, $R^1$, $R^2$, $R^4$, and $R^5$ are the same or different and independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and

* may be a linking point.

In some example embodiments, $R^3$ may be one of hydrogen, deuterium, and a methyl group.

In some example embodiments, at least one of $Ar^1$ and $Ar^2$ may be a substituted or unsubstituted C3 to C30 heterocyclic group including at least one hetero atom selected from nitrogen (N), sulfur (S), selenium (Se), and a combination thereof and optionally $R^3$ may be hydrogen, deuterium, or a methyl group.

In some example embodiments, Ar³ may be a condensed ring of a substituted or unsubstituted C6 to C30 arylene group, a substituted or unsubstituted C6 to C30 arene group, and a substituted or unsubstituted C3 to C30 heterocyclic group.

In some example embodiments, Ar³ may be a condensed ring of a substituted or unsubstituted phenylene group and a substituted or unsubstituted heterocyclic group having S, Se, Ge, and Te, and optionally R³ may be one of hydrogen, deuterium, and a methyl group:

In some example embodiments, the compound may be represented by one of Chemical Formulae 1-A to 1-D4.

[Chemical Formula 1-A]

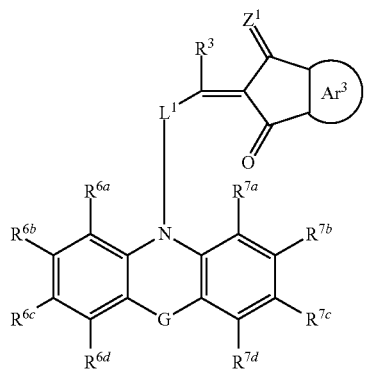

[Chemical Formula 1-B1]

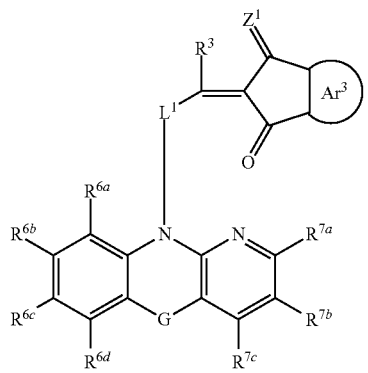

[Chemical Formula 1-B2]

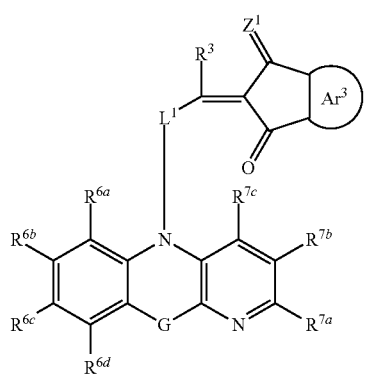

[Chemical Formula 1-C1]

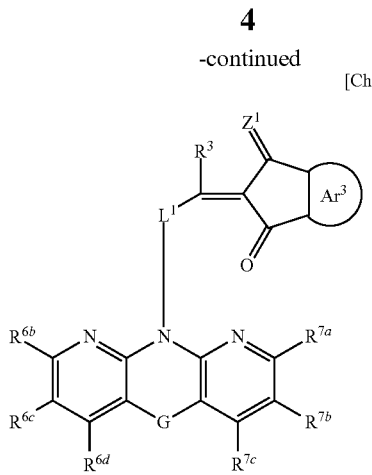

[Chemical Formula 1-C2]

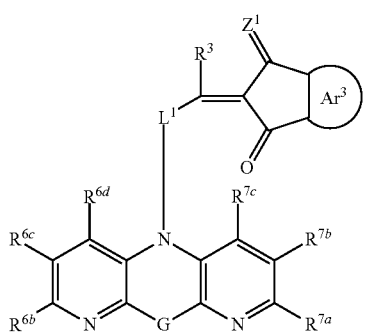

[Chemical Formula 1-D1]

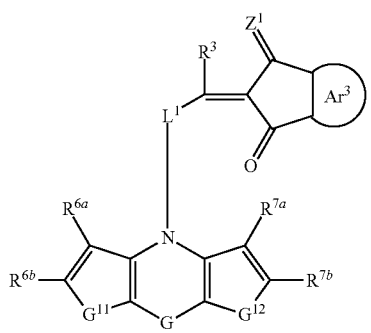

[Chemical Formula 1-D2]

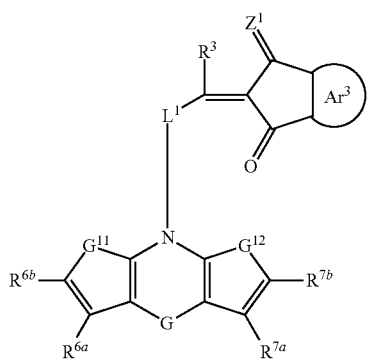

-continued

[Chemical Formula 1-D3]

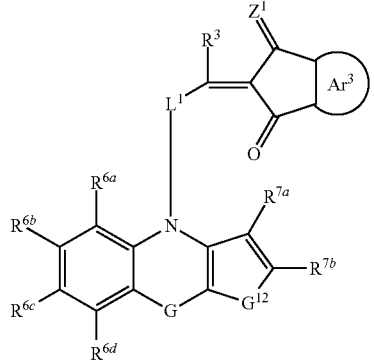

[Chemical Formula 1-D4]

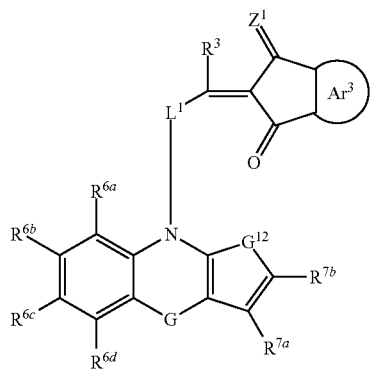

In Chemical Formulae 1-A to 1-D4, $L^1$ may be one of linking groups of Group 1, $Ar^3$ may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^3$ may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G may be one of a single bond, —O—, —S—, —Se—, —N═, —$(CR^fR^g)_k$—, —$NR^h$—, —$SiR^iR^j$—, —$GeR^kR^l$—, —$(C(R^m)$═$C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, and $R^k$ and $R^l$, $R^m$ and $R^n$, and $R^o$ and $R^p$ independently may be present or linked with each other to provide a ring, and k may be one of 1 and 2, $G^{11}$ and $G^{12}$ are the same or different and independently may be one of —S—, —Se—, —Te—, —$GeR^xR^y$—, and —$CR^zR^w$—, wherein $R^x$, $R^y$, $R^z$, and $R^w$ are the same or different and independently may be one of hydrogen, a halogen, a substituted or unsubstituted C1 to C10 alkyl group, and a substituted or unsubstituted C6 to C10 aryl group, $R^{6a}$ to $R^{6d}$ and $R^{7a}$ to $R^{7d}$ are the same or different and independently may be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ independently may be present or two adjacent groups thereof are linked with each other to provide a fused cycle, and $R^{7a}$ to $R^{7d}$ independently may be present or two adjacent groups thereof are linked with each other to provide a fused cycle.

In some example embodiments, the compound may be represented by one of Chemical Formulae 1-E to 1-G.

[Chemical Formula 1-E]

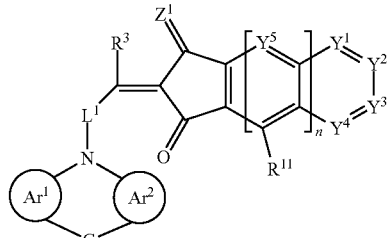

[Chemical Formula 1-F]

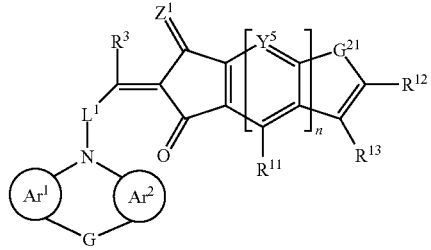

[Chemical Formula 1-G]

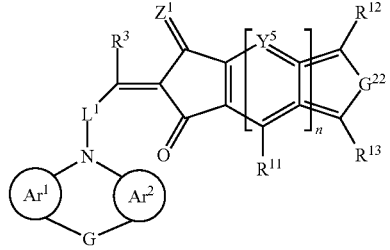

In Chemical Formulae 1-E to 1-G, $L^1$ may be one of linking groups of Group 1, $R^3$ may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, each of $Ar^1$ and $Ar^2$ are the same or different and independently may be one of a substituted or unsubstituted C6 to C30 arylene group, a substituted or unsubstituted C6 to C30 arene group, a substituted or unsubstituted C3 to C30 heterocyclic group, and combination thereof in a condensed, G may be one of a single bond, —O—, —S—, —Se—, —N═, —$(CR^fR^g)_k$—, —$NR^h$—, —$SiR^iR^j$—, —$GeR^kR^l$—, —$(C(R^m)$═$C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, $R^k$ and $R^l$, $R^m$ and $R^n$, and $R^o$ and $R^p$ independently may be present or linked with each other to provide a ring, and k may be one of 1 and 2, $Z^1$ may be O or $CR^bR^c$, wherein $R^b$ and $R^c$ are the same or different and independently may be hydrogen, a substituted or unsubstituted C1 to C10 alkyl group, a cyano group, or a cyano-containing group, provided that at least one of $R^b$ and $R^c$ may be a cyano group or a cyano-containing group, $Y^1$ to $Y^5$ are the same or different and independently may be one of N and $CR^d$, wherein $R^d$ may be one of hydrogen and a substituted or unsubstituted C1 to C10 alkyl group, $R^{11}$ to $R^{13}$ are the same or different and independently may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, n may be 0 or 1, and $G^{21}$ and $G^{22}$ independently may be one of —S—, —Se—, —$GeR^xR^y$—, and —Te—, wherein $R^x$ and $R^y$ are the same or different and independently may be one of hydrogen, a halogen, a substituted or unsubstituted C1 to C10 alkyl group, and a substituted or unsubstituted C6 to C10 aryl group.

In some example embodiments, at least one of $Y^1$ to $Y^4$ may be N.

In some example embodiments, at least one of $Ar^1$ and $Ar^2$ may be a heteroarylene (or heteroarene) group including at least one hetero atom selected from nitrogen (N), sulfur (S), selenium (Se), and a combination thereof.

In some example embodiments, at $R^3$ may be one of hydrogen, deuterium, and a methyl group.

In some example embodiments, the compound may be represented by one of Chemical Formulae 1-H to 1-S4.

[Chemical Formula 1-H]

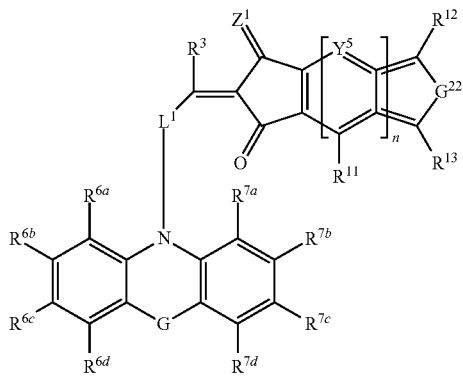

[Chemical Formula 1-I]

[Chemical Formula 1-J]

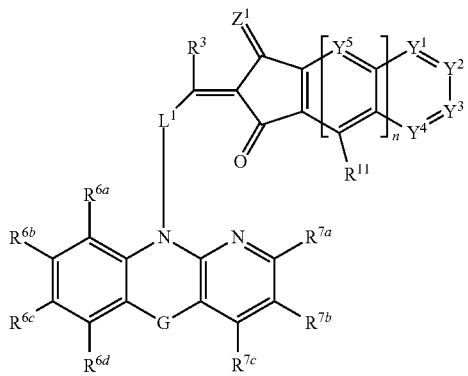

[Chemical Formula 1-K1]

[Chemical Formula 1-L1]

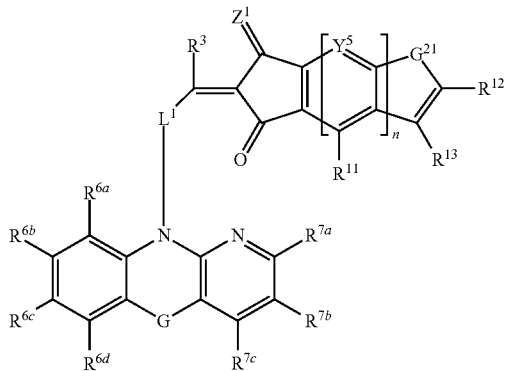

[Chemical Formula 1-M1]

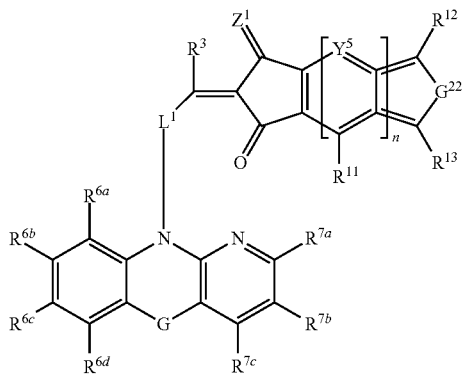

-continued
[Chemical Formula 1-K2]
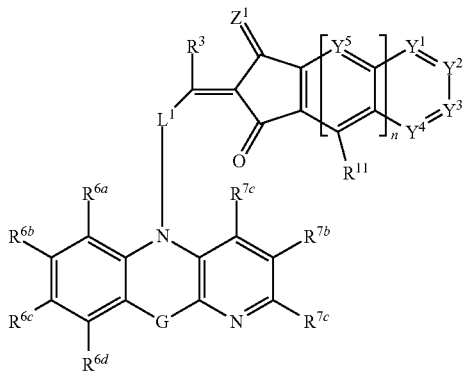
[Chemical Formula 1-L2]
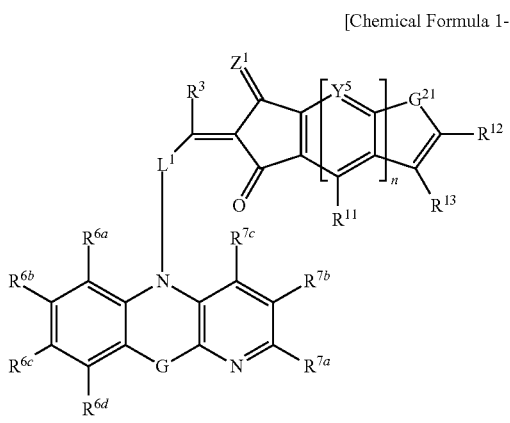
[Chemical Formula 1-M2]
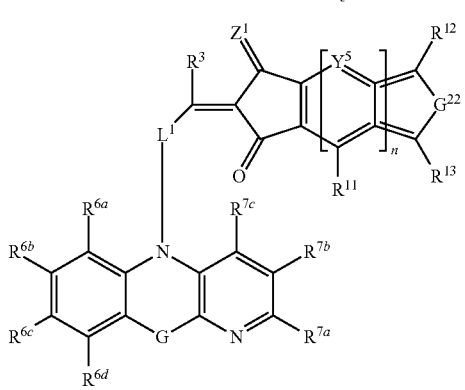
[Chemical Formula 1-N1]
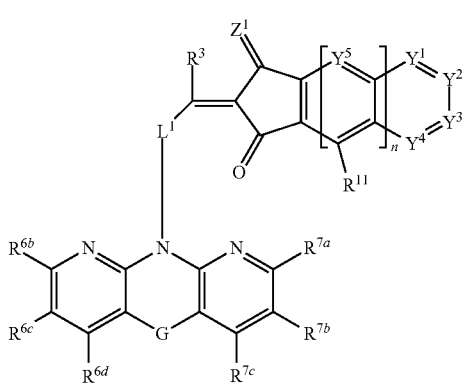
[Chemical Formula 1-O1]
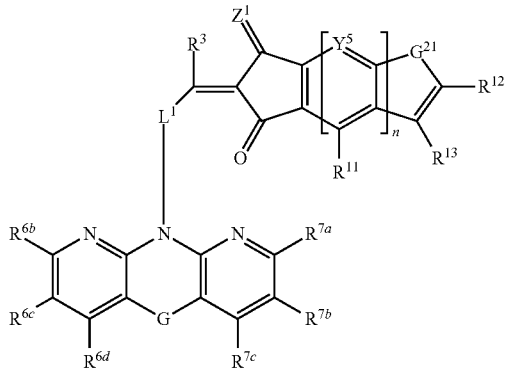
[Chemical Formula 1-P1]
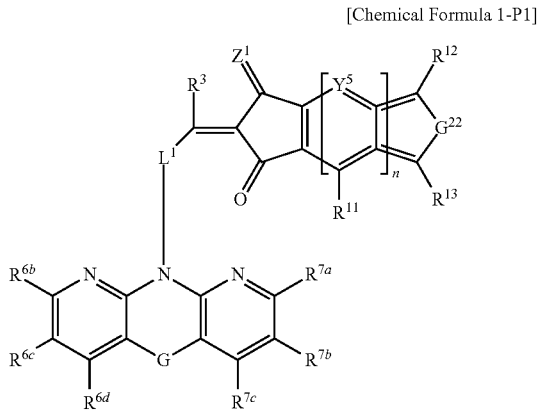
[Chemical Formula 1-N2]
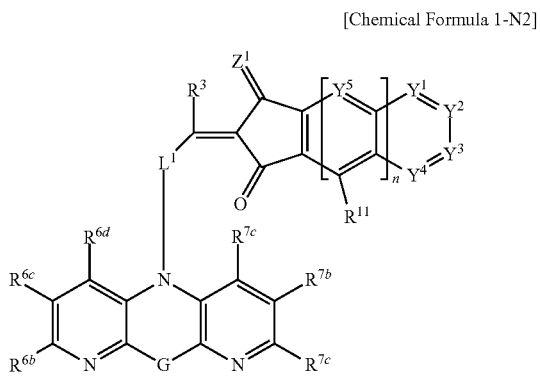
[Chemical Formula 1-O2]
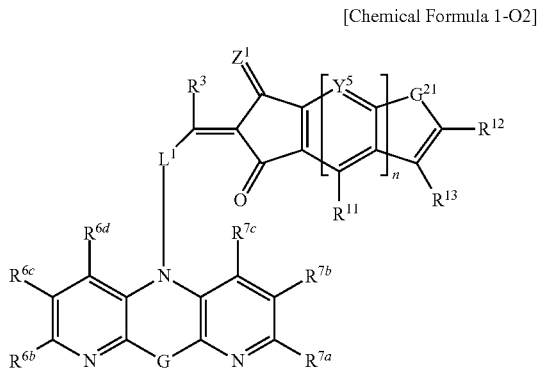

[Chemical Formula 1-P2]
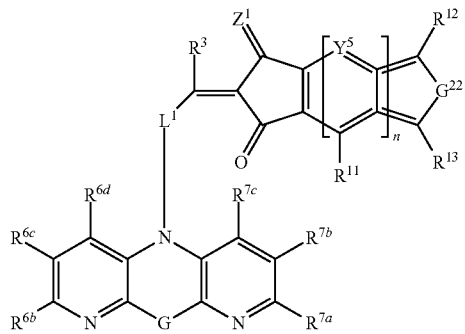
[Chemical Formula 1-Q1]
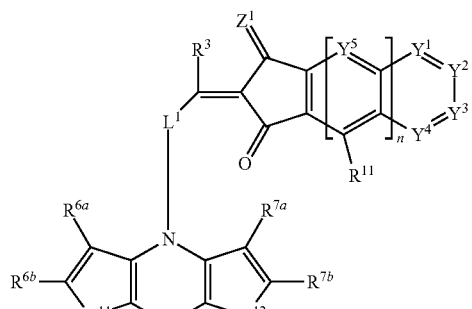
[Chemical Formula 1-R1]
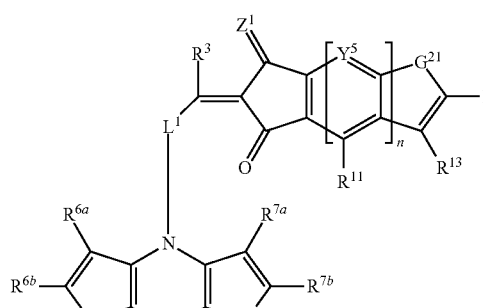
[Chemical Formula 1-S1]
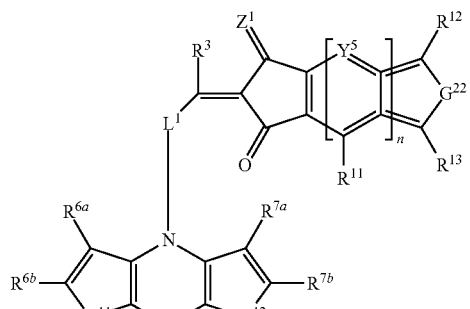
[Chemical Formula 1-Q2]
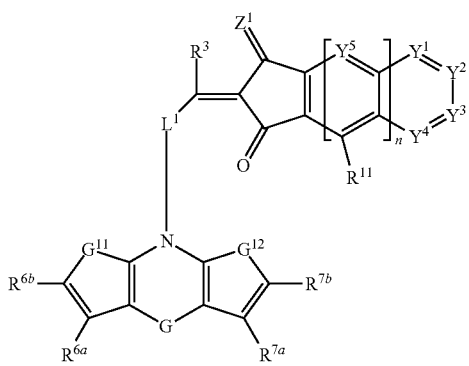
[Chemical Formula 1-R2]
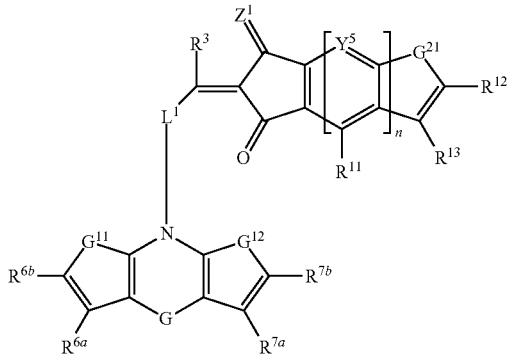
[Chemical Formula 1-S2]
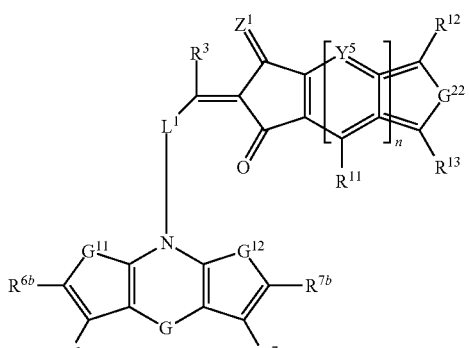
[Chemical Formula 1-Q3]
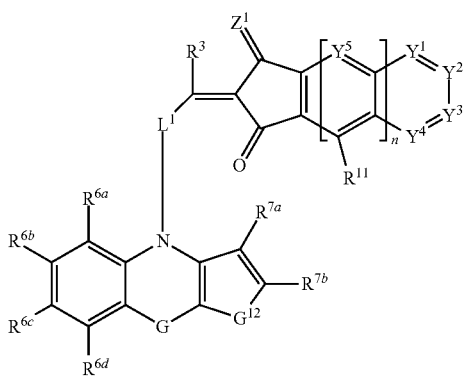

-continued

[Chemical Formula 1-R3]

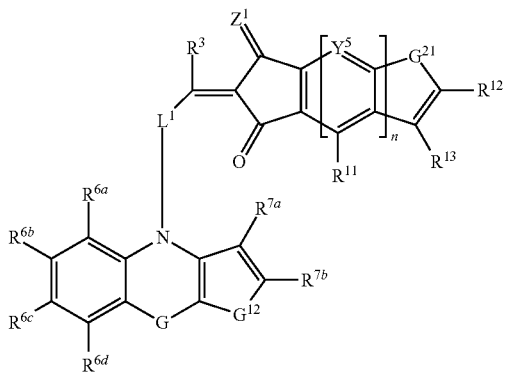

[Chemical Formula 1-S3]

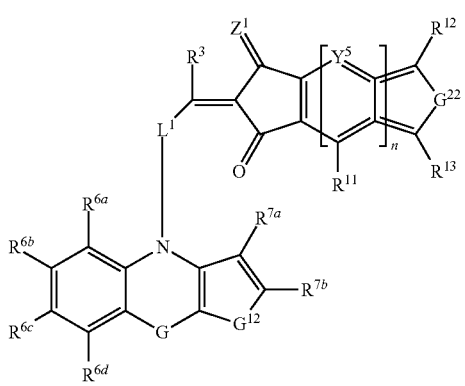

[Chemical Formula 1-Q4]

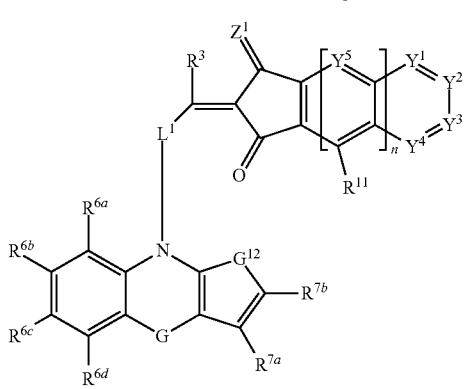

[Chemical Formula 1-R4]

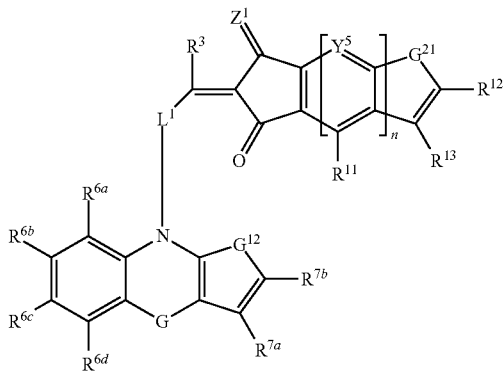

-continued

[Chemical Formula 1-S4]

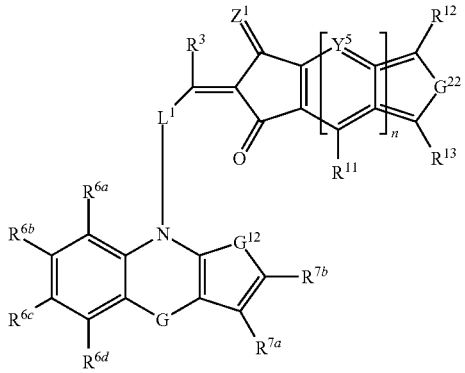

In Chemical Formulae 1-H to 1-S4, $L^1$ may be one of linking groups of Group 1, $R^3$ may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G may be one of a single bond, —O—, —S—, —Se—, —N═, —(CR$^f$R$^g$)$_k$—, —NR$^h$—, —SiR$^i$R$^j$—, —GeR$^k$R$^l$—, —(C(R$^m$)═C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ independently may be present or linked with each other to provide a ring, and k may be one of 1 and 2, $G^{11}$ and $G^{12}$ are the same or different and independently may be one of —S—, —Se—, —Te—, —GeR$^x$R$^y$—, and —CR$^z$R$^w$—, wherein R$^x$, R$^y$, R$^z$, and R$^w$ are the same or different and independently may be one of hydrogen, a halogen, a substituted or unsubstituted C1 to C10 alkyl group, and a substituted or unsubstituted C6 to C10 aryl group, $R^{6a}$ to $R^{6d}$ and $R^{7a}$ to $R^{7d}$ are the same or different and independently may be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ independently may be present or two adjacent groups thereof are linked with each other to provide a fused cycle, $R^{7a}$ to $R^{7d}$ independently may be present or two adjacent groups thereof are linked with each other to provide a fused cycle, $Z^1$ may be O or CR$^b$R$^c$, wherein R$^b$ and R$^c$ are the same or different and independently may be hydrogen, a substituted or unsubstituted C1 to C10 alkyl group, a cyano group, or a cyano-containing group, provided that at least one of R$^b$ and R$^c$ may be a cyano group or a cyano-containing group, $Y^1$ to $Y^5$ are the same or different and independently may be one of N and CR$^d$, wherein R$^d$ may be one of hydrogen and a substituted or unsubstituted C1 to C10 alkyl group, $R^{11}$ to $R^{13}$ are the same or different and independently may be one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, n may be 0 or 1, and $G^{21}$ and $G^{22}$ independently may be one of —S—, —Se—, —GeR$^x$R$^y$—, and —Te—, wherein R$^x$ and R$^y$ are the same or different and independently may be one of hydrogen, a halogen, a substituted or unsubstituted C1 to C10 alkyl group, and a substituted or unsubstituted C6 to C10 aryl group.

In some example embodiments, $R^3$ may be one of hydrogen, deuterium, and a methyl group.

In some example embodiments, the compound may be represented by Chemical Formula 1-T.

[Chemical Formula 1-T]

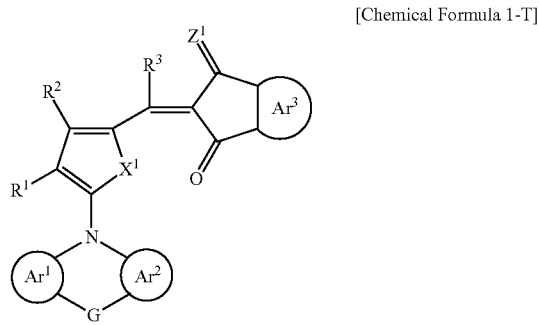

In Chemical Formula 1-T, $X^1$ may be one of —Se—, —Te—, —O—, —S(=O)—, —S(=O)$_2$—, —NR$^a$—, —SiR$^b$R$^c$—, and —GeR$^d$R$^e$—, wherein R$^a$, R$^b$, R$^c$, R$^d$, and R$^e$ are the same or different and independently may be one of hydrogen and a substituted or unsubstituted C1 to C10 alkyl group, Ar$^3$ may be one of a substituted or unsubstituted C6 to C30 arylene group, a substituted or unsubstituted C6 to C30 arene group, a substituted or unsubstituted heterocyclic group including at least one hetero atom selected from S, Se, Te, Ge, N, and a combination thereof in a condensed ring, $R^1$ to $R^3$ are the same or different and independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, each of $Ar^1$ and $Ar^2$ are the same or different and independently may be one of a substituted or unsubstituted C6 to C30 arylene group, a substituted or unsubstituted C6 to C30 arene group, and G may be one of a single bond, —O—, —S—, —Se—, —N=, —(CR$^f$R$^g$)$_k$—, —NR$^h$—, —SiR$^i$R$^j$, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ independently may be present or linked with each other to provide a ring, and k may be one of 1 and 2.

In some example embodiments, the compound may be represented by Chemical Formula 1-U.

[Chemical Formula 1-U]

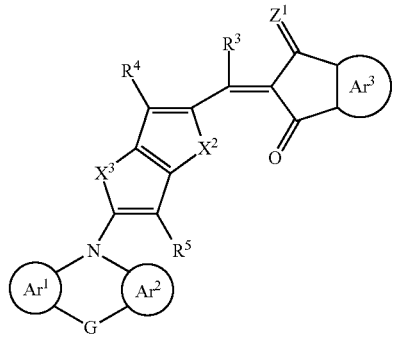

In Chemical Formula 1-U, $X^2$ and $X^3$ are the same or different and independently may be one of —S—, —Se—, —Te—, —O—, —S(=O)—, —S(=O)$_2$—, —NR$^a$—, —SiR$^b$R$^c$—, and —GeR$^d$R$^e$—, wherein R$^a$, R$^b$, R$^c$, R$^d$, and R$^e$ are the same or different and independently may be one of hydrogen and a substituted or unsubstituted C1 to C10 alkyl group, $Ar^1$ to $Ar^3$ are the same or different and independently may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^3$ to $R^5$ are the same or different and independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G may be one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ independently may be present or linked with each other to provide a ring, and k may be one of 1 and 2.

In some example embodiments, the compound may be represented by Chemical Formula 1-V.

[Chemical Formula 1-V]

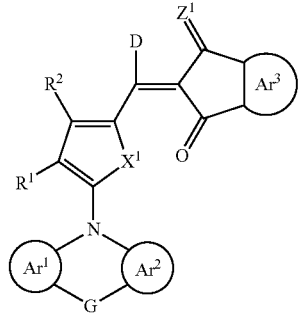

In Chemical Formula 1-V, $X^1$ may be one of —Se—, —Te—, —O—, —S(=O)—, —S(=O)$_2$—, —NR$^a$—, —SiR$^b$R$^c$—, and —GeR$^d$R$^e$—, wherein $R^a$, $R^b$, $R^c$, $R^d$, and $R^e$ are the same or different and independently may be one of hydrogen and a substituted or unsubstituted C1 to C10 alkyl group, D may be deuterium, $Ar^1$ to $Ar^3$ are the same or different and independently may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^1$ and $R^2$ are the same or different and independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G may be one of a single bond, —O—, —S—, —Se—, —N=, —$(CR^fR^g)_k$—, —$NR^h$—, —$SiR^iR^j$—, —$GeR^kR^l$—, —$(C(R^m)=C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, $R^k$ and $R^l$, $R^m$ and $R^n$, and $R^o$ and $R^p$ independently may be present or linked with each other to provide a ring, and k may be one of 1 and 2.

In some example embodiments, the compound may be represented by Chemical Formula 1-W.

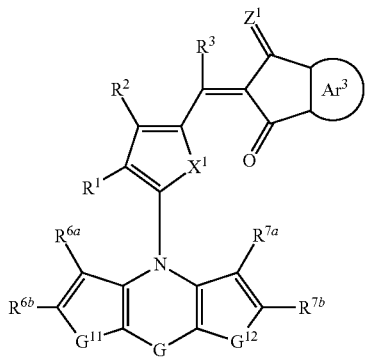

[Chemical Formula 1-W]

In Chemical Formula 1-W, $X^1$ may be one of —Se—, —Te—, —O—, —S(=O)—, —S(=O)$_2$—, —$NR^a$—, —$SiR^bR^c$—, and —$GeR^dR^e$—, wherein $R^a$, $R^b$, $R^c$, $R^d$, and $R^e$ are the same or different and independently may be one of hydrogen and a substituted or unsubstituted C1 to C10 alkyl group, $Ar^3$ may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^1$ to $R^3$ are the same or different and independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G may be one of a single bond, —O—, —S—, —Se—, —N=, —$(CR^fR^g)_k$—, —$NR^h$—, —$SiR^iR^j$—, —$GeR^kR^l$—, —$(C(R^m)=C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, and $R^k$ and $R^l$, $R^m$ and $R^n$, and $R^o$ and $R^p$ independently may be present or linked with each other to provide a ring, and k may be one of 1 and 2.

$G^{11}$ and $G^{12}$ are the same or different and independently may be one of —S—, —Se—, —Te—, —$GeR^xR^y$—, and —$CR^zR^w$—, wherein $R^x$, $R^y$, $R^z$, and $R^w$ are the same or different and independently may be one of hydrogen, a halogen, a substituted or unsubstituted C1 to C10 alkyl group, and a substituted or unsubstituted C6 to C10 aryl group, $R^{6a}$ and $R^{6b}$ and $R^{7a}$ and $R^{7b}$ are the same or different and independently may be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ and $R^{6b}$ independently may be present or linked with each other to provide a fused cycle, and $R^{7a}$ and $R^{7b}$ independently may be present or linked with each other to provide a fused cycle.

In some example embodiments, the compound may have a maximum absorption wavelength ($\lambda_{max}$) of greater than or equal to about 510 nm and less than or equal to about 565 nm in a thin film state.

According to some example embodiments, a photoelectric device includes a first electrode and a second electrode facing each other and an organic layer between the first electrode and the second electrode, wherein the organic layer includes the compound.

In some example embodiments, the organic layer may include an active layer, the active layer may include a p-type semiconductor and an n-type semiconductor, and the compound may be included in the active layer.

In some example embodiments, the active layer may have a maximum absorption wavelength of greater than or equal to about 510 nm and less than or equal to about 565 nm.

According to some example embodiments, an image sensor includes the photoelectric device.

In some example embodiments, the image sensor may include a semiconductor substrate integrated with a plurality of first photo-sensing device sensing light in a blue wavelength region and a plurality of second photo-sensing device sensing light in a red wavelength region, and the photoelectric device may be on the semiconductor substrate and configured to selectively sense light in a green wavelength region.

In some example embodiments, the image sensor may further include a color filter layer including a blue filter overlapping with the first photo-sensing device and a red filter overlapping with the second photo-sensing device.

In some example embodiments, the first photo-sensing device and the second photo-sensing device may be stacked in a vertical direction in the semiconductor substrate.

In some example embodiments, the image sensor may include green photoelectric device configured to sense light in a green wavelength region, a blue photoelectric device configured to sense light in a blue wavelength region, and a red photoelectric device configured to sense light in a red wavelength region that are stacked, and the green photoelectric device may be the photoelectric device.

According to example embodiments, an electronic device includes the photoelectric device.

According to example embodiments, an electronic device includes the image sensor.

According to example embodiments, a compound may include a structure represented by one of Chemical Formulae 1-T to 1-W:

[Chemical Formula 1-T]

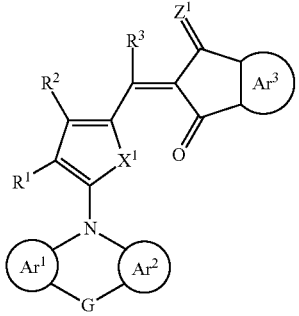

[Chemical Formula 1-U]

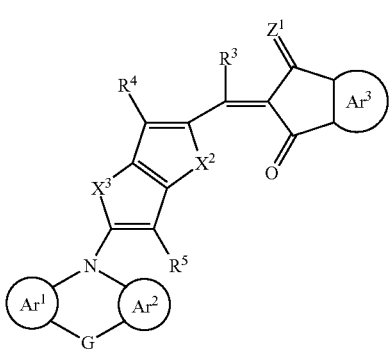

[Chemical Formula 1-V]

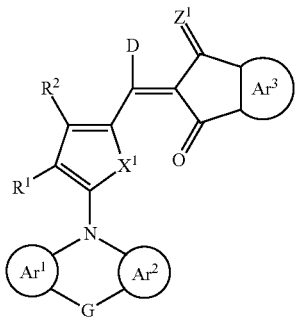

[Chemical Formula 1-W]

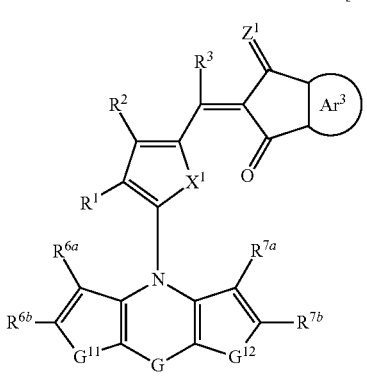

wherein in Chemical Formulae 1-T to 1-W, $Ar^1$ to $Ar^3$ independently may be one of a substituted or unsubstituted C6 to C30 arylene group, a substituted or unsubstituted C6 to C30 arene group, a substituted or unsubstituted C3 to C30 heterocyclic group, and a combination thereof in a condensed ring, D may be deuterium, $R^1$, $R^2$, $R^3$, $R^4$, and $R^5$ independently may be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G may be one of a single bond, —O—, —S—, —Se—, —N═, —(CR$^f$R$^g$)$_k$—, —NR$^h$—, —SiR$^i$R$^j$—, —GeR$^k$R$^l$—, —(C(R$^m$)═C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ independently may be one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ independently may be present or linked with each other to provide a ring, and k may be one of 1 and 2, $Z^1$ may be one of O or CR$^b$R$^c$, wherein R$^b$ and R$^c$ independently may be one of hydrogen, a substituted or unsubstituted C1 to C10 alkyl group, a cyano group, and a cyano-containing group, provided that at least one of R$^b$ and R$^c$ may be a cyano group or a cyano-containing group, and $X^1$, $X^2$ and $X^3$ independently may be one of —S—, —Se—, —Te—, —O—, —S(═O)—, —S(═O)$_2$—, —NR$^a$—, —SiR$^b$R$^c$—, and —GeR$^d$R$^e$—, $R^a$ to $R^e$ independently may be one of hydrogen and a substituted or unsubstituted C1 to C10 alkyl group, $G^{11}$ and $G^{12}$ independently may be one of —S—, —Se—, —Te—, —GeR$^x$R$^y$—, and —CR$^z$R$^w$—, wherein R$^x$, R$^y$, R$^z$, and R$^w$ independently may be one of hydrogen, a halogen, a substituted or unsubstituted C1 to C10 alkyl group, and a substituted or unsubstituted C6 to C10 aryl group, $R^{6a}$ and $R^{6b}$ and $R^{7a}$ and $R^{7b}$ independently may be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ may be present or two adjacent groups thereof are linked with each other to provide a fused cycle, and $R^{7a}$ to $R^{7d}$ may be present or two adjacent groups thereof are linked with each other to provide a fused cycle, and

* may be a linking point.

In some example embodiments, the structure may be represented by one of the groups listed in Group 2:

[Group 2]

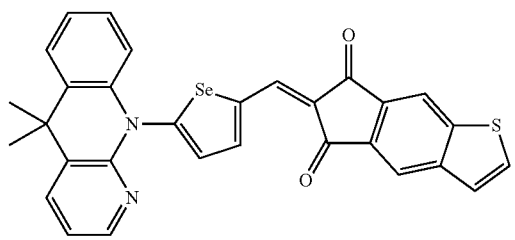

21
-continued
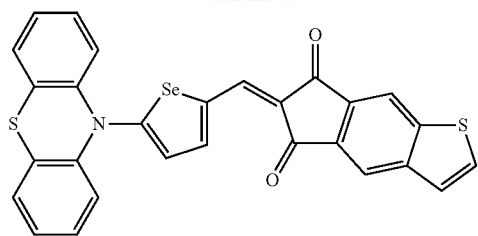
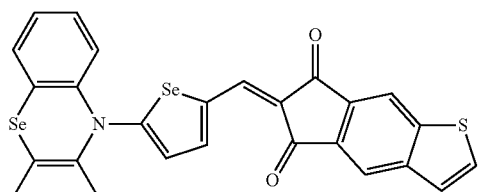
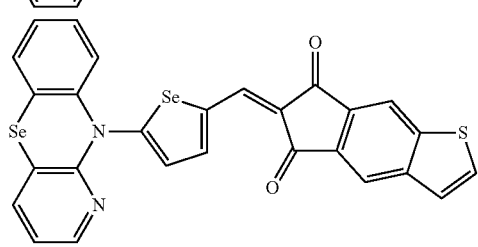
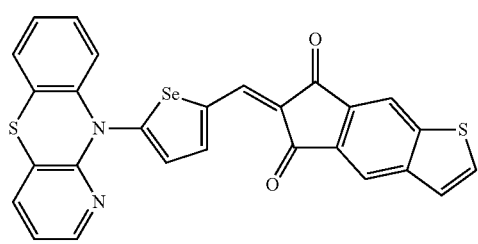
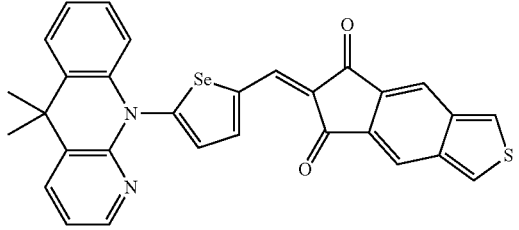
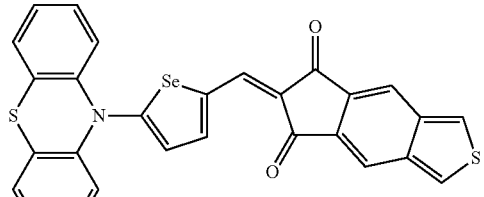
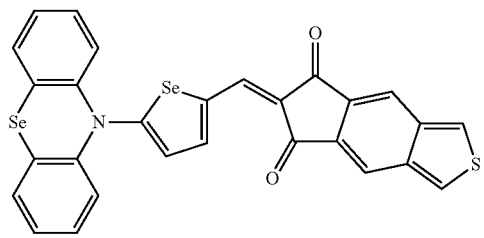
22
-continued
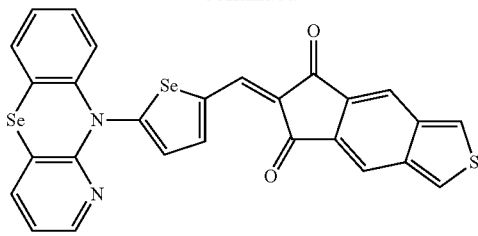
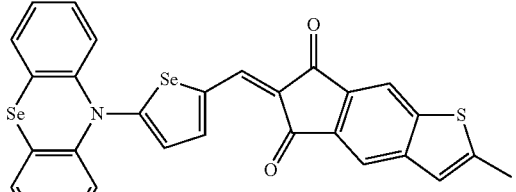
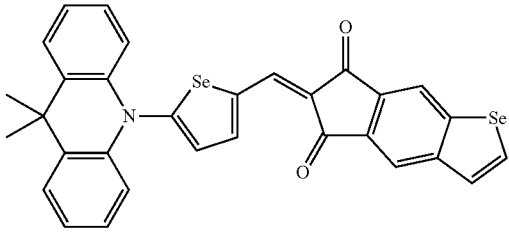
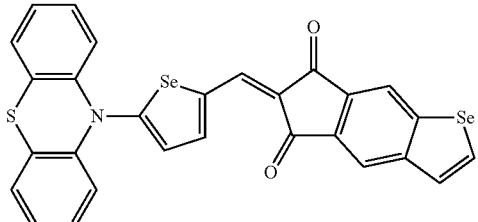
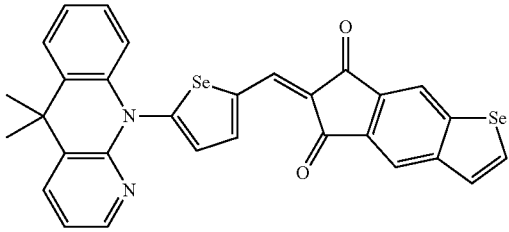
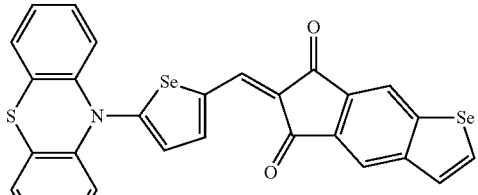
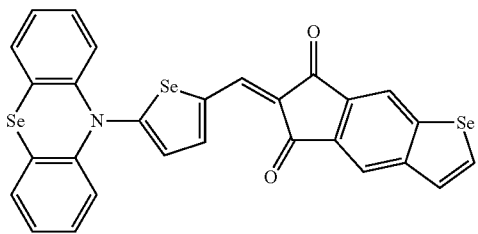

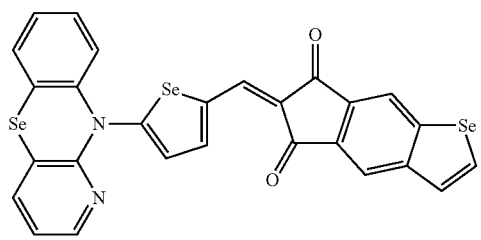
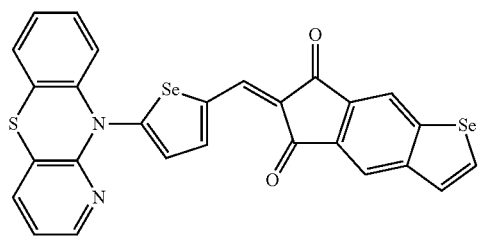
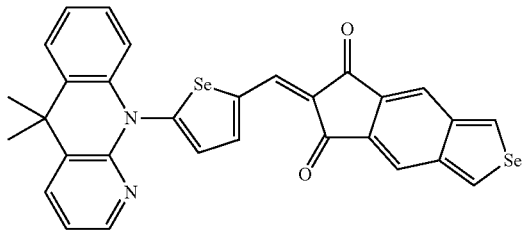
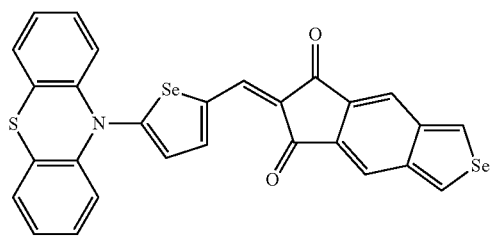
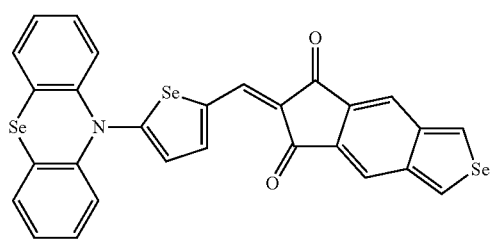
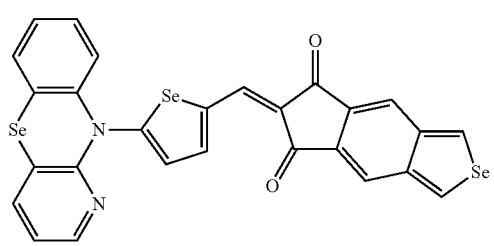
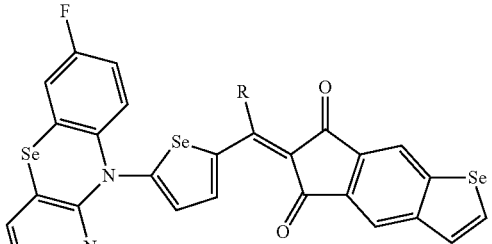
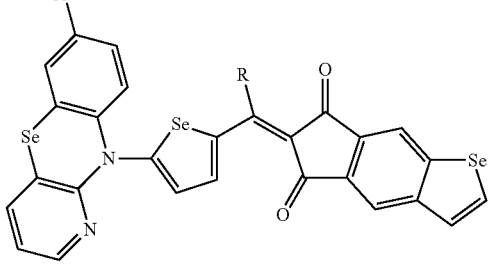
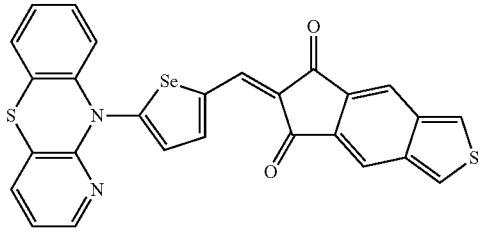
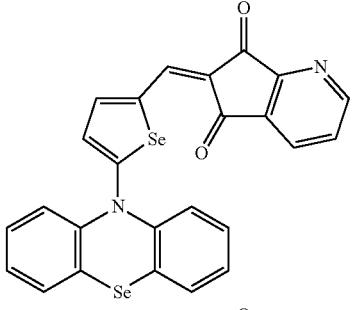
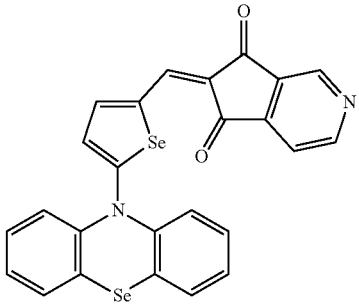
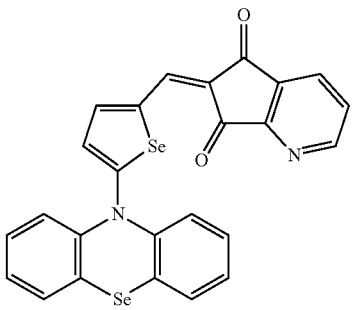

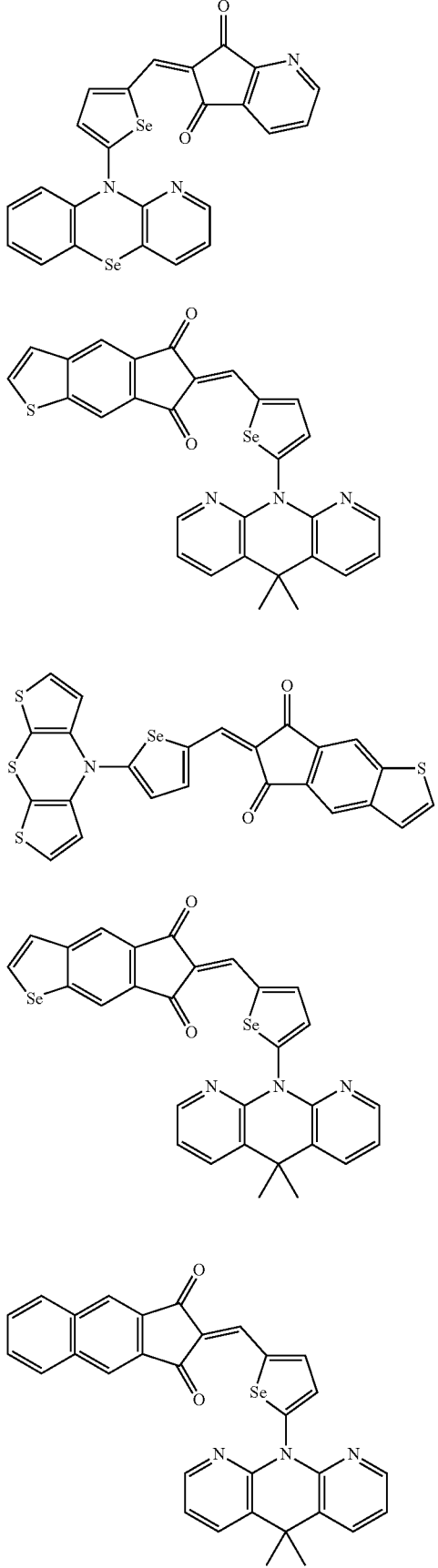
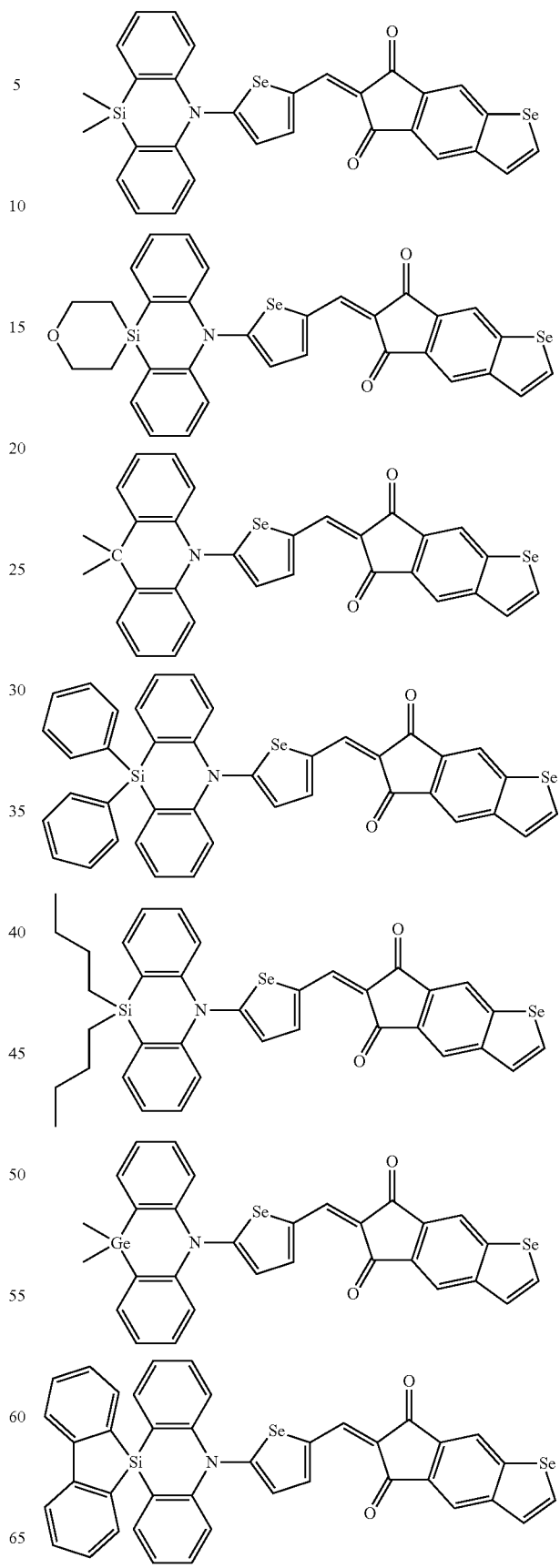

-continued
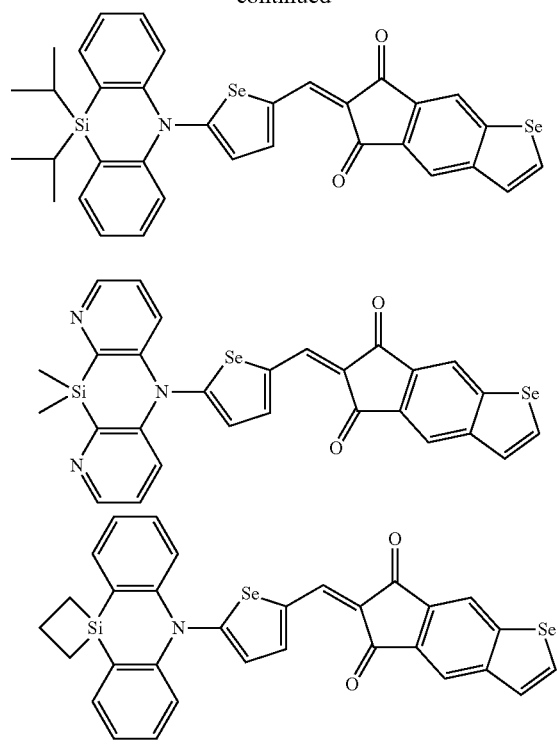
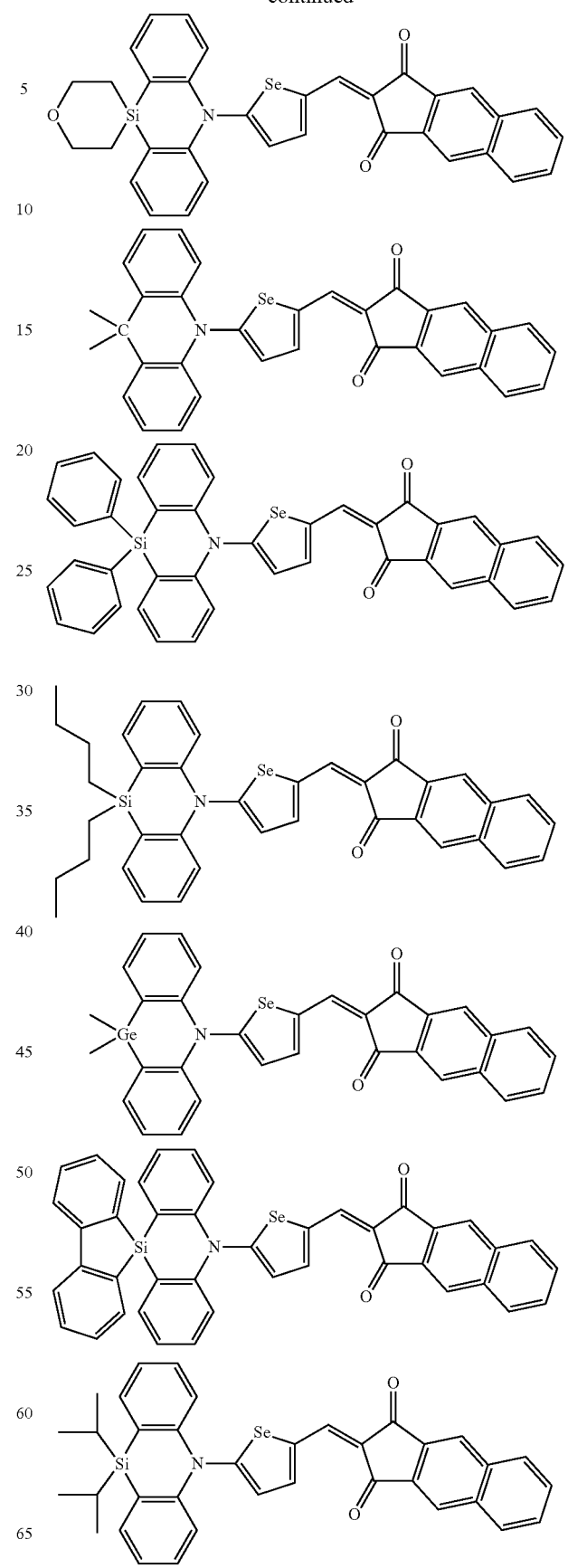

29
-continued
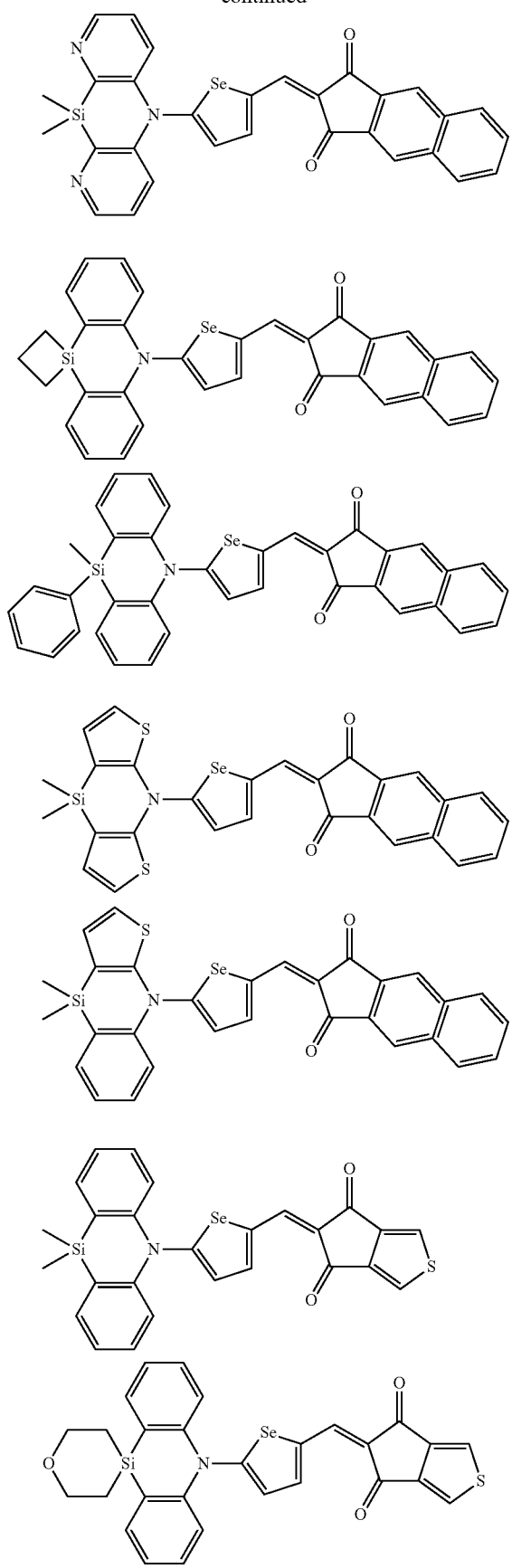
30
-continued
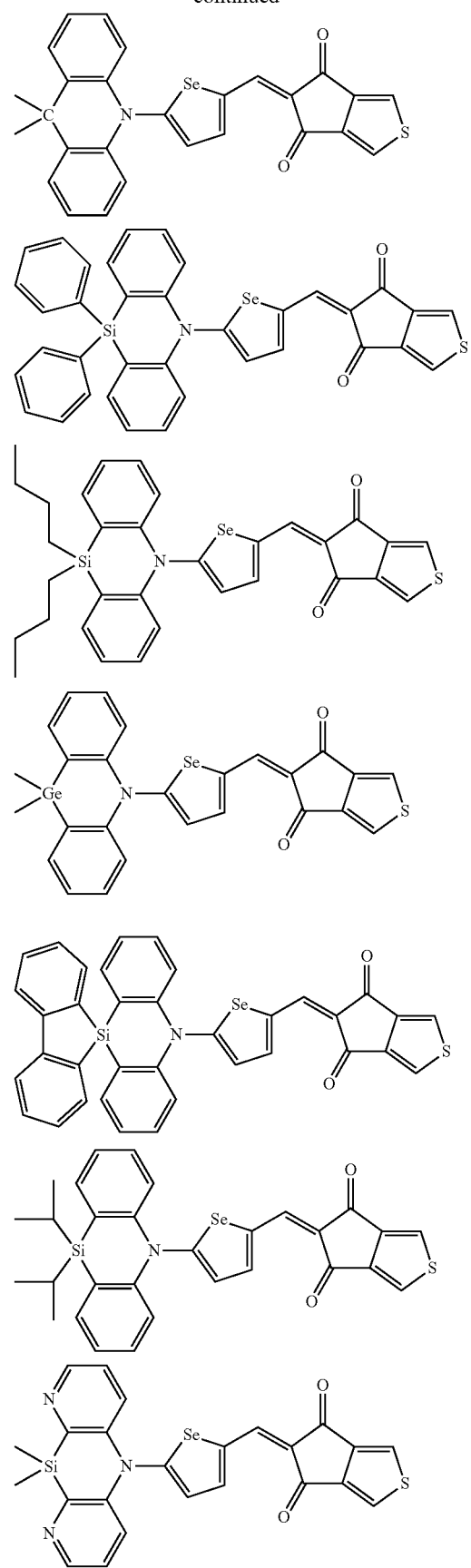

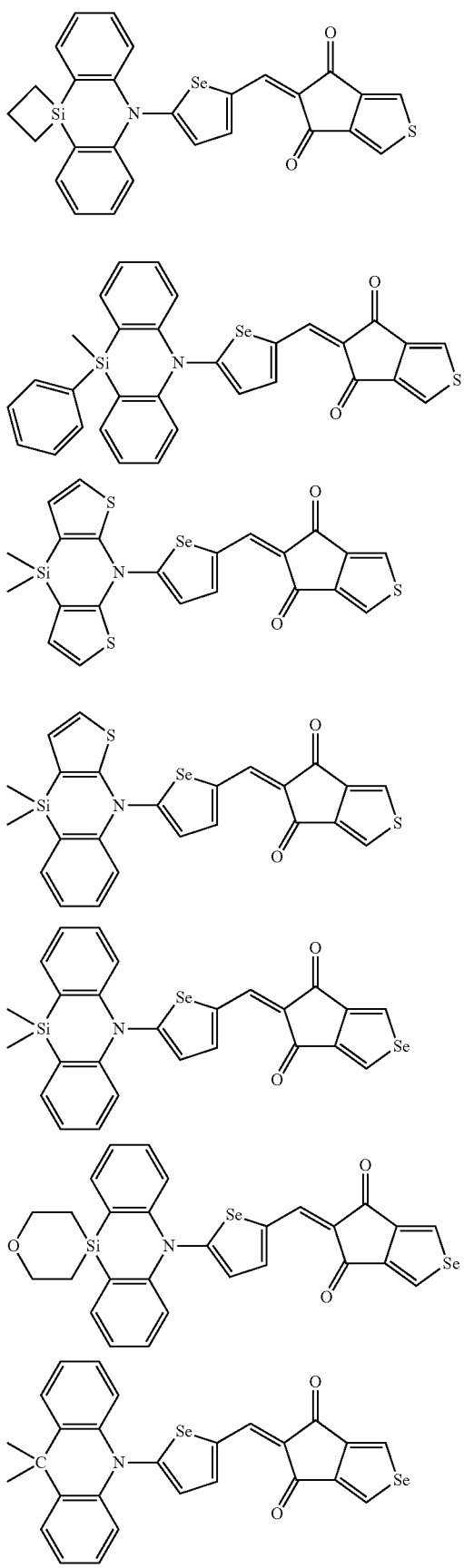
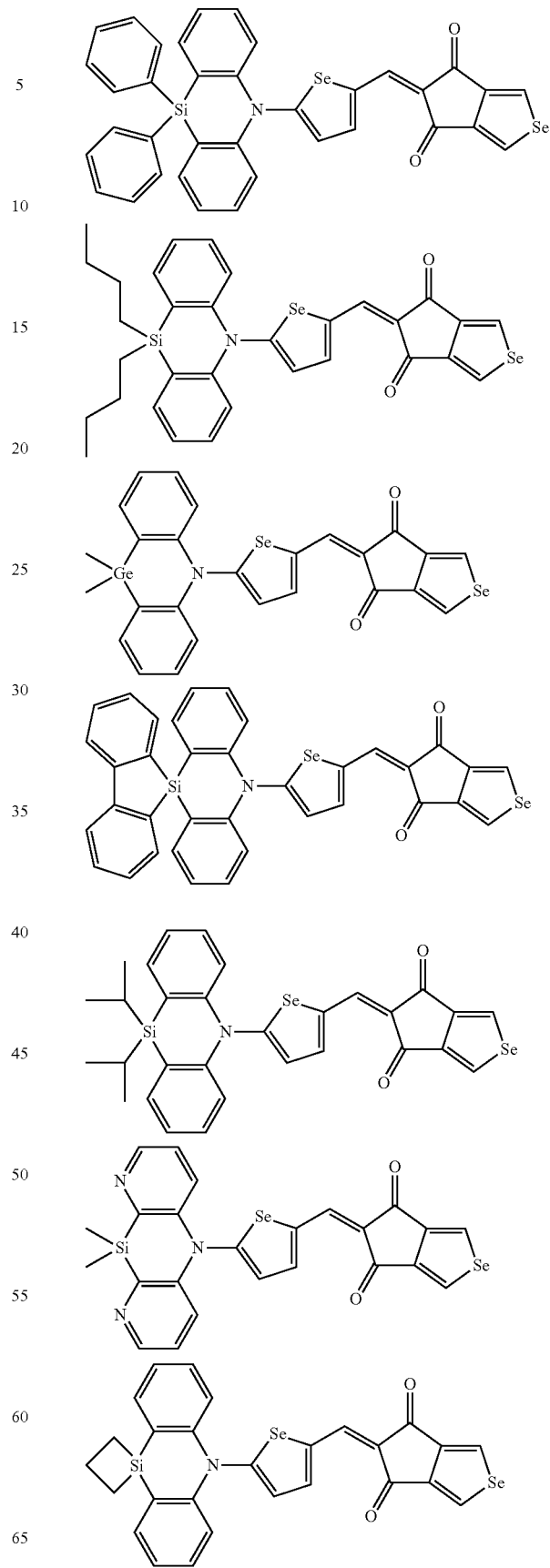

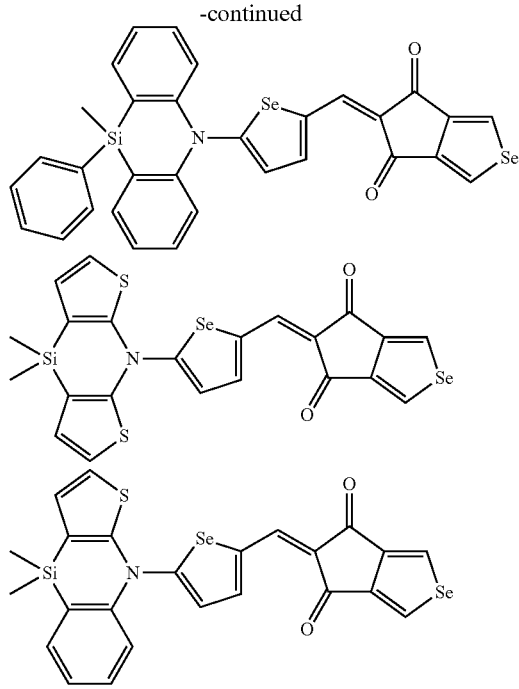
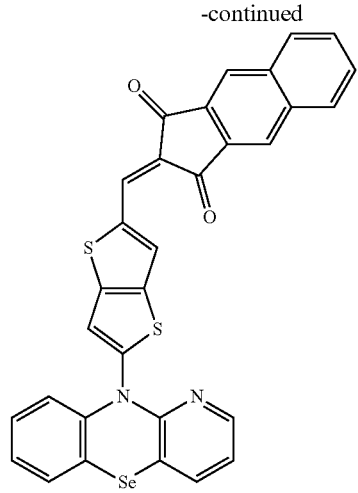
In some example embodiments, the structure may be represented by one of the groups listed in Group 3:
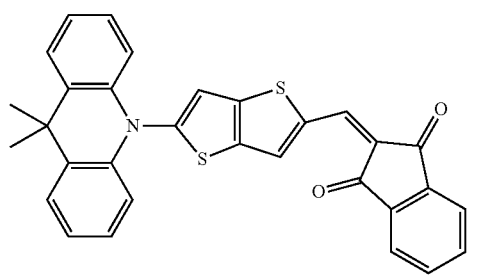
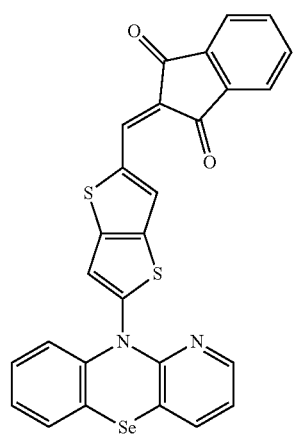
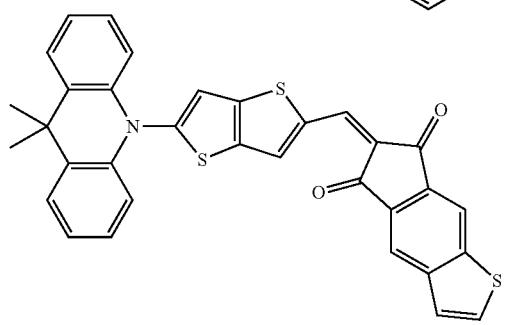
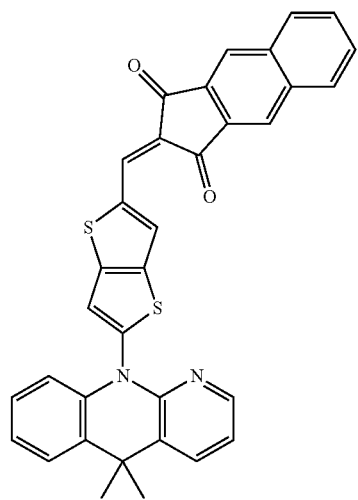

-continued
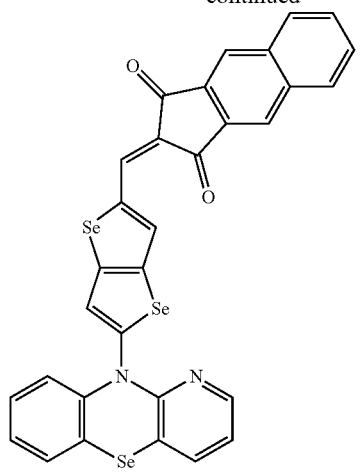
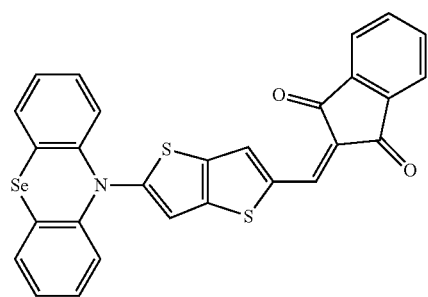
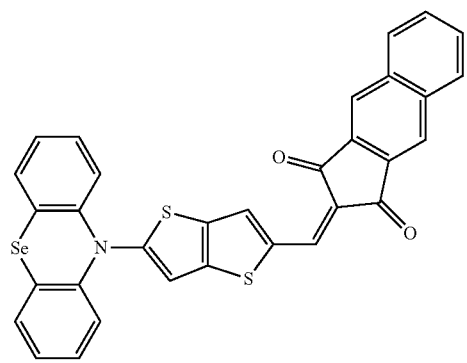
In some example embodiments, the structure may be represented by one of the groups listed in Group 4:
[Group 4]
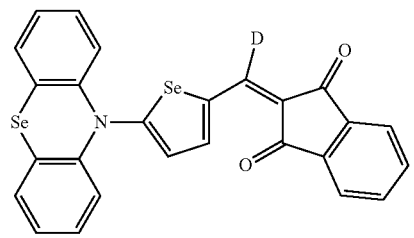
-continued
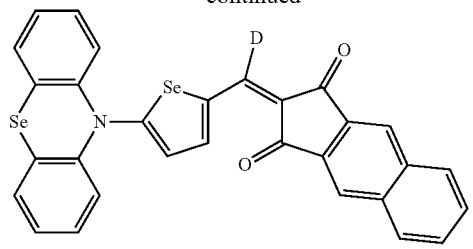
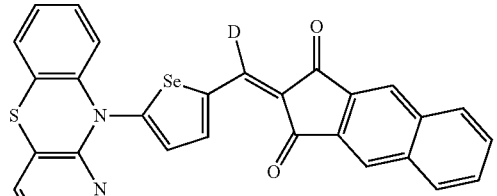
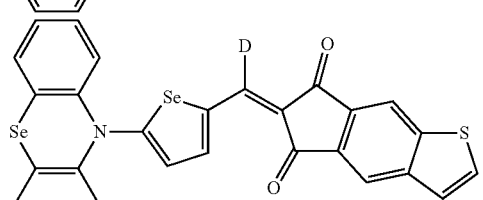
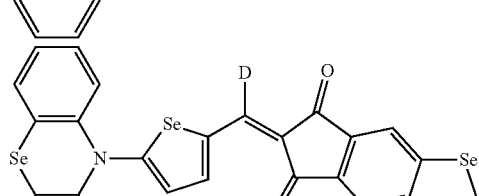
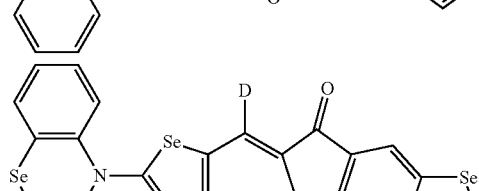
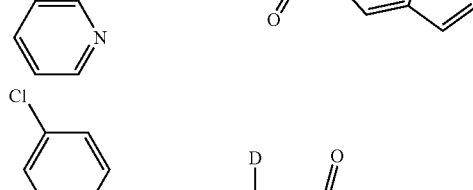
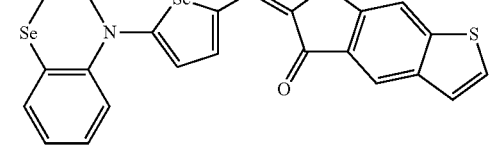
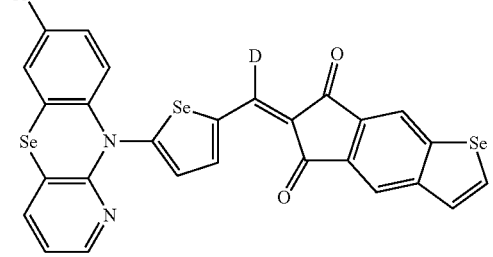

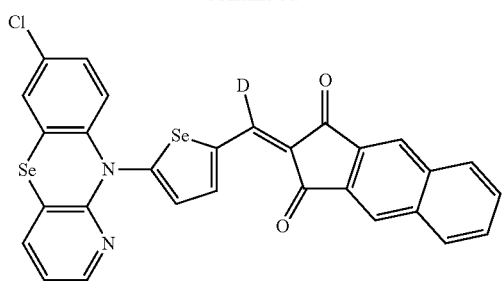
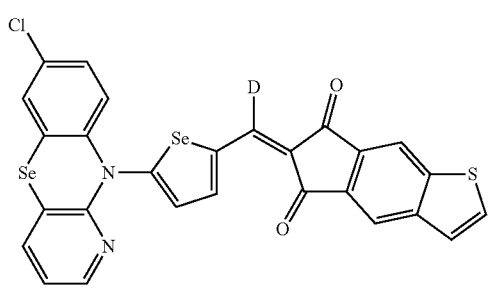
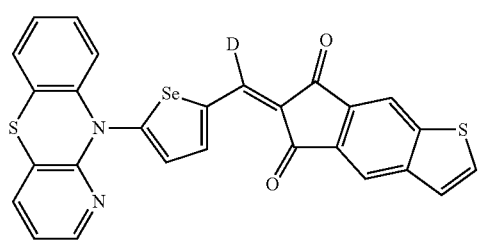
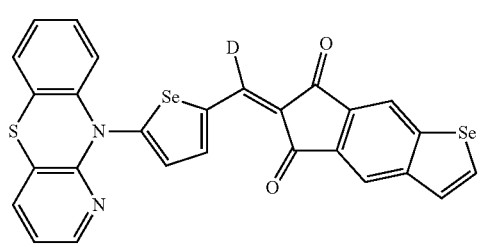
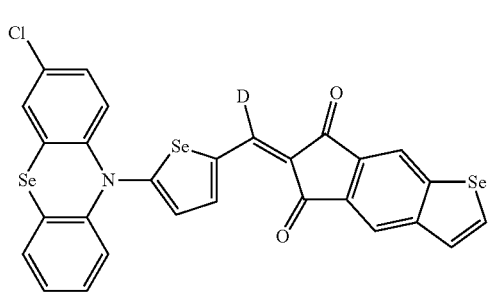
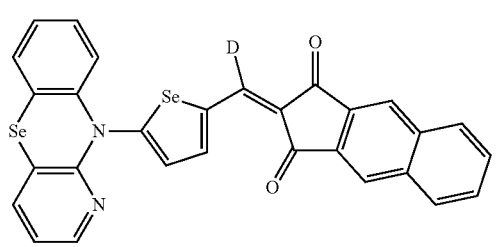
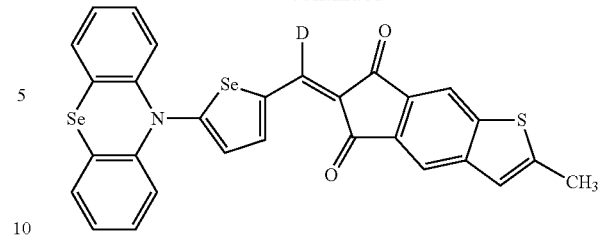
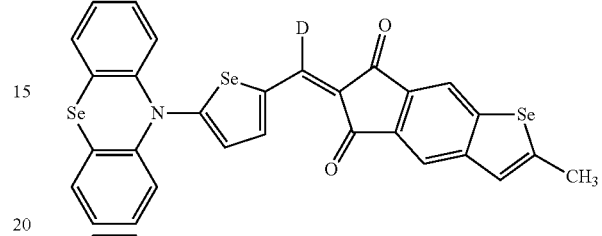
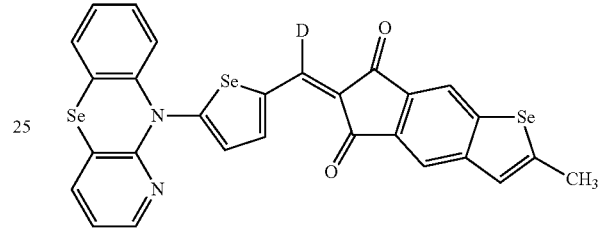
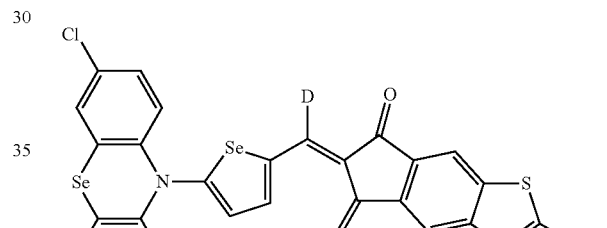
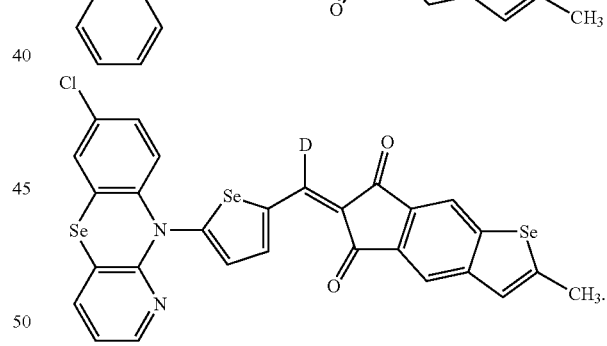
In some example embodiments, the structure may be represented by one of the groups listed in Group 5:
[Group 5]
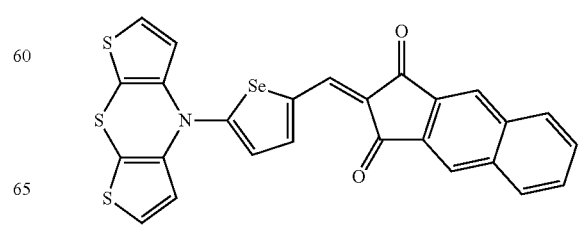

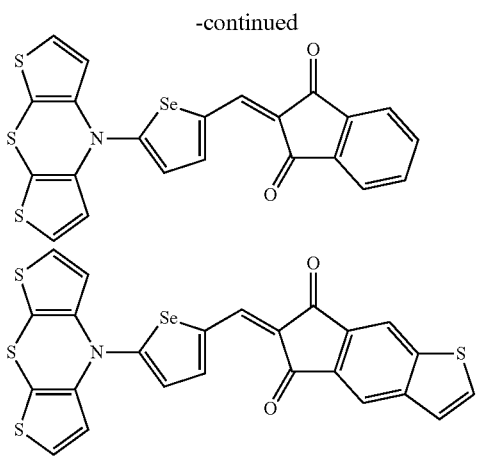

DETAILED DESCRIPTION

Figure 1:
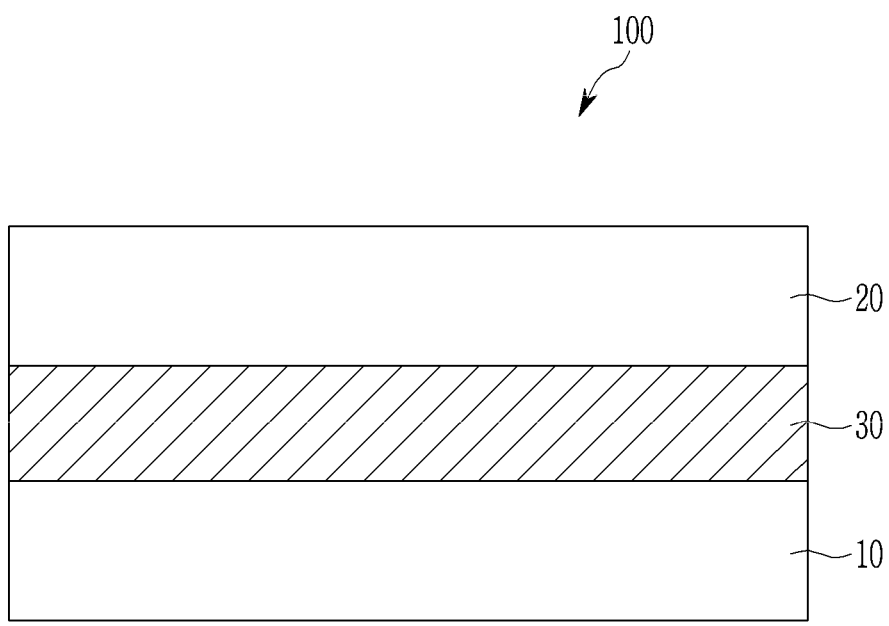
FIG. 1 is a cross-sectional view of an organic photoelectric device according to example embodiments.

Example embodiments will hereinafter be described in detail, and may be easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, when a definition is not otherwise provided, "substituted" refers to replacement of hydrogen of a compound or a group by a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when specific definition is not otherwise provided, "hetero" refers to one including 1 to 3 heteroatoms selected from N, O, S, P, and Si.

As used herein, "an alkyl group" for example refers to a methyl group, an ethyl group, a propyl group, an isopropyl group, an n-butyl group, an isobutyl group, a t-butyl group, a pentyl group, a hexyl group, and the like.

As used herein, "a cycloalkyl group" refers to a cyclopropyl group, a cyclobutyl group, a cyclopentyl group, a cyclohexyl group, and the like.

As used herein, "an aryl group" refers to a substituent including all element of the cycle having p-orbitals which form conjugation, and may be a monocyclic, polycyclic or fused polycyclic (e.g., rings sharing adjacent pairs of carbon atoms) functional group.

As used herein, when a definition is not otherwise provided, "a cyano-containing group" refers to a monovalent group such as a C1 to C30 alkyl group, a C2 to C30 alkenyl group, or a C2 to C30 alkynyl group where at least one hydrogen is replaced by a cyano group. The cyano-containing group also refers to a divalent group such as a group represented by $=CR^{x'}-(CR^xR^y)_p-CR^{y'}(CN)_2$ wherein $R^x$, $R^y$, $R^{x'}$, and $R^{y'}$ are the same or different and are independently one of hydrogen and a C1 to C10 alkyl group and p is an integer of 0 to 10 (and/or 1 to 10). Specific examples of the cyano-containing group may be a dicyanomethyl group, a dicyanovinyl group, a cyanoethynyl group, and the like.

As used herein, when a definition is not otherwise provided, "a heterocycle" refers to a cycle including at least one heteroatom, wherein the heteroatom may be one of N, O, S, P, and Si and the cycle may be an aliphatic cycle, an aromatic cycle, or a fused cycle (e.g., fused cyclic structure) thereof.

As used herein, when a definition is not otherwise provided, "a combination thereof" refers to at least two substituents bound to each other by a single bond or a C1 to C10 alkylene group, or at least two fused substituents.

As used herein, the term "5-membered aromatic ring" refers to a 5-membered cyclic group (e.g., C5 aryl group) having a conjugation structure or a 5-membered heterocyclic group (e.g., C2 to C4 heteroaryl group) having a conjugation structure. As used herein, the term "6-membered aromatic ring" refers to a 6-membered cyclic group (e.g. C6 aryl group) having a conjugation structure or a 6-membered heterocyclic group (e.g., C2 to C5 heteroaryl group) having a conjugation structure, but is not limited thereto. The aromatic ring may include the 5-membered aromatic ring or the 6-membered aromatic ring, but is not limited thereto.

Hereinafter, a compound according to an embodiment is described.

A compound according to an embodiment is represented by Chemical Formula 1.

[Chemical Formula 1]

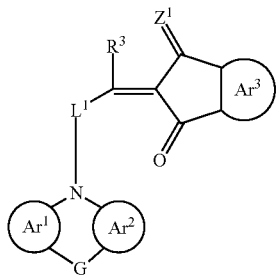

In Chemical Formula 1, $L^1$ is a substituted or unsubstituted divalent heterocycle or a substituted or unsubstituted divalent condensation heterocycle, $Ar^1$ to $Ar^3$ are the same or different and are independently one of a substituted or unsubstituted C6 to C30 arylene group, a substituted or unsubstituted C6 to C30 arene group, a substituted or unsubstituted C3 to C30 heterocyclic group, and a condensed ring of two or more of the foregoing rings, $R^3$ is one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ are independently present or linked with each other to provide a ring (e.g., fused cyclic structure), and k is one of 1 and 2, and $Z^1$ is O or CR$^b$R$^c$, wherein R$^b$ and R$^c$ are the same or different and are independently hydrogen, a substituted or unsubstituted C1 to C10 alkyl group, a cyano group, or a cyano-containing group, provided that at least one of R$^b$ and R$^c$ is a cyano group or a cyano-containing group.

The compound represented by Chemical Formula 1 is a light absorbing material that absorbs light in a predetermined wavelength region and has a structure including an electron donor moiety and an electron acceptor moiety on both sides of a linker ($L^1$—CR$^3$).

For example, $L^1$ may have for example a fused cycle (e.g., fused cyclic structure) of a substituted or unsubstituted 5-membered heterocycle or 6-membered heterocycle with at least one 5-membered heterocycle or 6-membered heterocycle.

For example, $L^1$ may be one of linking groups of Group 1.

[Group 1]

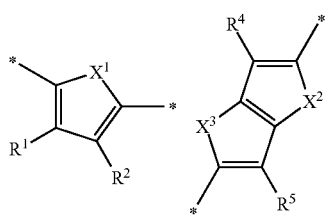

In Group 1, $X^1$ is one of —Se—, —Te—, —O—, —S(=O)—, —S(=O)$_2$—, —NR$^a$—, —SiR$^b$R$^c$—, and —GeR$^d$R$^e$—, $X^2$ and $X^3$ are the same or different and are independently one of —S—, —Se—, —Te—, —O—, —S(=O)—, —S(=O)$_2$—, —NR$^a$—, —SiR$^b$R$^c$—, and —GeR$^d$R$^e$—, $R^a$ to $R^e$ are the same or different and are independently one of hydrogen or a substituted or unsubstituted C1 to C10 alkyl group, $R^1$, $R^2$, $R^4$, and $R^5$ are the same or different and are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and

* is a linking point.

For example, $X^1$ to $X^3$ in $L^1$ may increase an intramolecular interaction with oxygen (O) of a carbonyl group of the electron acceptor moiety and thus may improve absorption intensity in a particular wavelength.

For example, $R^3$ may be hydrogen, deuterium or a substituted or unsubstituted C1 to C30 alkyl group, for example hydrogen, deuterium, or a methyl group.

The electron donor moiety of Chemical Formula 1 may be a fused cycle (e.g., fused cyclic structure) of at least three cycles and each of $Ar^1$ and $Ar^2$ may be fused with a nitrogen-containing cycle.

In Chemical Formula 1, each of $Ar^1$ and $Ar^2$ are linked by nitrogen (N) and G and thus provides an entirely one conjugation structure and improves thermal stability of the compound. Such a conjugation structure may be formed by fusing three to four 5-membered or 6-membered aromatic rings, but is not limited thereto.

For example, each of $Ar^1$ and $Ar^2$ may independently be a substituted or unsubstituted phenylene group, a substituted or unsubstituted naphthylene group, a substituted or unsubstituted anthracenylene group or a heteroarylene (or heteroarene) including at least one heteroatom selected from nitrogen (N), sulfur (S), selenium (Se), and a combination thereof. Herein, the heteroarylene group may be for example one of a pyrrolylene group, a pyrazolylene group, an imidazolylene group, an oxazolylene group, an isoxazolylene group, a thiazolylene group, an isothiazolylene group, a pyridinylene group, a pyridazinylene group, a pyrimidinylene group, a pyrazinylene group, an indolylene group, a quinolinylene group, an isoquinolinylene group, a naphthyridinylene group, a cinnolinylene group, a quinazolinylene group, a phthalazinylene group, a benzotriazinylene group, a pyridopyrazinylene group, a pyridopyrimidinylene group, a pyridopyridazinylene group, a thienylene group, a benzothienylene group, a selenophenylene group, and a benzo selenophenylene group.

For example, each of $Ar^1$ and $Ar^2$ may independently be a substituted or unsubstituted phenylene group, a substituted or unsubstituted naphthylene group, or a substituted or unsubstituted anthracenylene group.

For example, at least one of $Ar^1$ and $Ar^2$ may be a heteroarylene (or heteroarene) including at least one heteroatom selected from nitrogen (N), sulfur (S), selenium (Se), and a combination thereof.

For example, one of $Ar^1$ and $Ar^2$ may be a substituted or unsubstituted phenylene group, a substituted or unsubstituted naphthylene group or a substituted or unsubstituted anthracenylene group and the other of $Ar^1$ and $Ar^2$ may be a heteroarylene (or heteroarene) including at least one heteroatom selected from nitrogen (N), sulfur (S), selenium (Se), and a combination thereof.

For example, one of Ar¹ and Ar² may be a substituted or unsubstituted phenylene group, a substituted or unsubstituted naphthylene group, or a substituted or unsubstituted anthracenylene group and the other of Ar¹ and Ar² may be a heteroarylene (or heteroarene) including nitrogen (N).

For example, one of Ar¹ and Ar² may be a substituted or unsubstituted phenylene group, a substituted or unsubstituted naphthylene group, or a substituted or unsubstituted anthracenylene group and the other of Ar¹ and Ar² may be a heteroarylene (or heteroarene) including sulfur (S) or selenium (Se).

For example, each of Ar¹ and Ar² may independently be a heteroarylene (or heteroarene) including at least one heteroatom selected from nitrogen (N), sulfur (S), selenium (Se), and a combination thereof.

For example, each of Ar¹ and Ar² may independently be a heteroarylene (or heteroarene) including nitrogen (N).

For example, each of Ar¹ and Ar² may independently be a heteroarylene (or heteroarene) including sulfur (S) or selenium (Se).

For example, at least one of Ar¹ and Ar² may include a heteroatom selected from sulfur (S), selenium (Se), germanium (Ge), and tellurium (Te) at No. 3 and/or No. 5 with respect to G.

For example, at least one of Ar¹ and Ar² may include a heteroatom selected from nitrogen (N), sulfur (S), and selenium (Se) at No. 1 and/or No. 9 with respect to G. Accordingly, a heteroatom included in at least one of Ar¹ and Ar², X¹ to X³ in L¹, and oxygen (O) of the carbonyl group in the electron acceptor moiety may increase an intramolecular interaction and thus may improve absorption intensity in a particular wavelength.

For example, the electron donor moiety may be represented by one of Chemical Formulae A to I.

[Chemical Formula A]

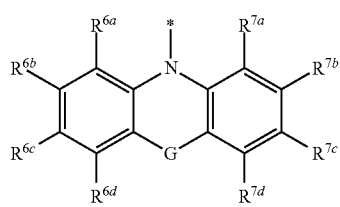

[Chemical Formula B]

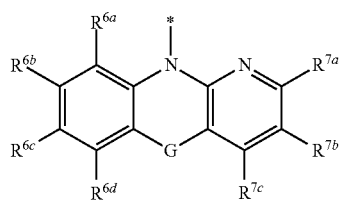

[Chemical Formula C]

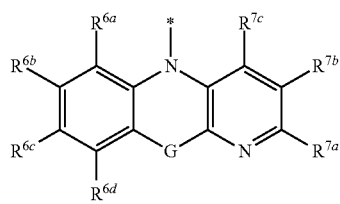

[Chemical Formula D]

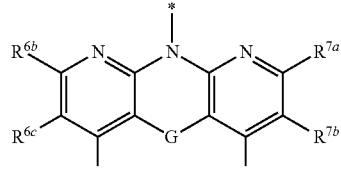

[Chemical Formula E]

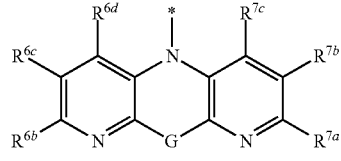

[Chemical Formula F]

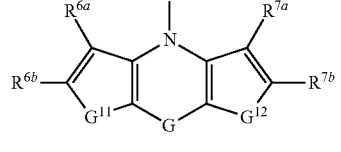

[Chemical Formula G]

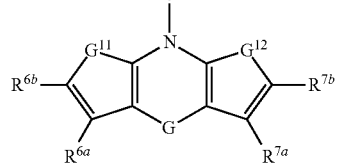

[Chemical Formula H]

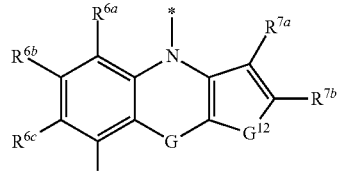

[Chemical Formula I]

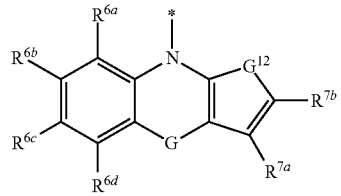

In Chemical Formulae A to I,

G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ are independently present or linked with each other to provide a ring (e.g., fused cyclic structure), and k is one of 1 and 2, G$^{11}$ and G$^{12}$ are the same or different and are independently one of —S—, —Se—, —Te—, —GeR$^x$R$^y$—, and —CR$^z$R$^w$—, wherein R$^x$, R$^y$, R$^z$, and R$^w$ are the same or different and are independently one of hydrogen, a halogen, a substituted or unsubstituted C1 to C10 alkyl group, and a substituted or unsubstituted C6 to C10 aryl group, R$^{6a}$ to R$^{6d}$ and R$^{7a}$ to R$^{7d}$ are the same or different and are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ are independently present or two adjacent groups thereof are linked with each other to provide a fused cycle (e.g., fused cyclic structure), and $R^{7a}$ to $R^{7d}$ are independently present or two adjacent groups thereof are linked with each other to provide a fused cycle (e.g., fused cyclic structure).

The compound represented by Chemical Formula 1 may be represented by one of Chemical Formulae 1-A to 1-D4 according to an electron donor moiety.

[Chemical Formula 1-A]

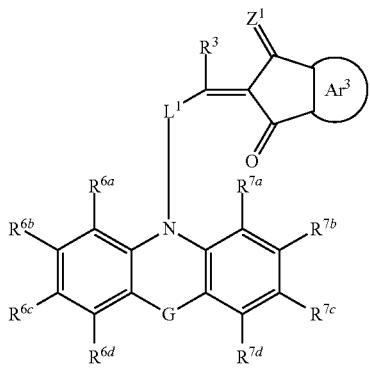

[Chemical Formula 1-B1]

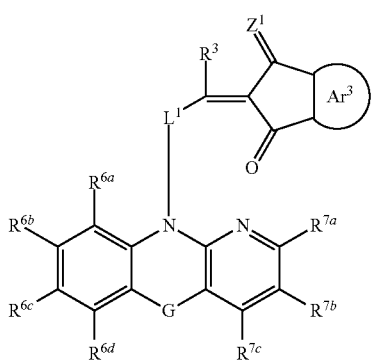

[Chemical Formula 1-B2]

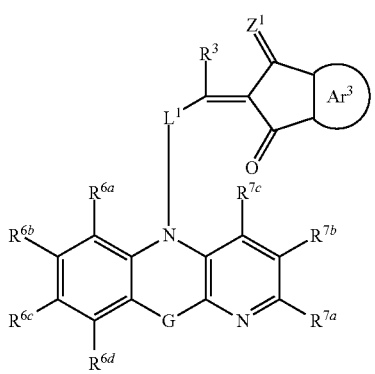

[Chemical Formula 1-C1]

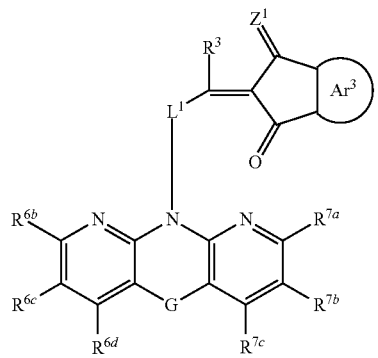

[Chemical Formula 1-C2]

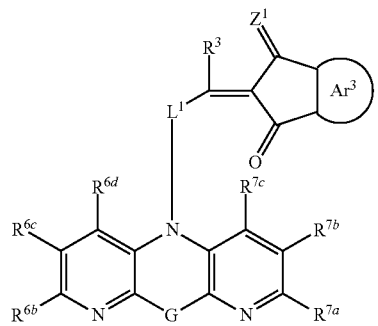

[Chemical Formula 1-D1]

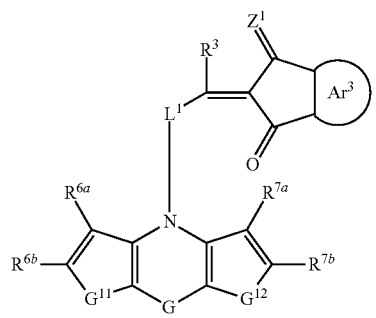

[Chemical Formula 1-D2]

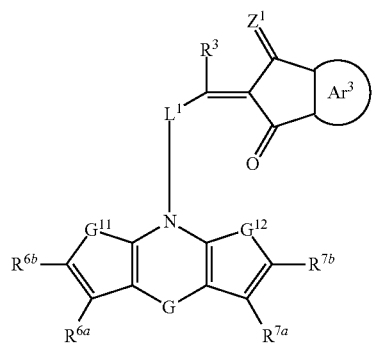

[Chemical Formula 1-D3]

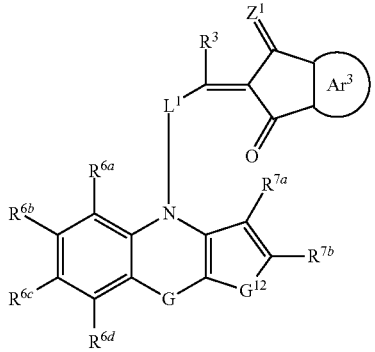

[Chemical Formula 1-D4]

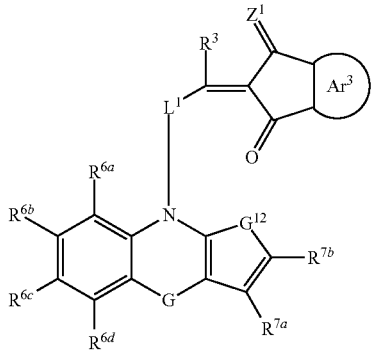

In Chemical Formulae 1-A to 1-D4, $L^1$, $Ar^3$, $R^3$, $Z^1$, G, $G^{11}$, $G^{12}$, $R^{6a}$ to $R^{6d}$, and $R^{7a}$ to $R^{7d}$ are the same as described above.

The electron acceptor moiety of Chemical Formula 1 is a cyclic group bound to a methane group and the cyclic group includes a fused cycle (e.g., fused cyclic structure) of a cyclopentyl group substituted with at least one carbonyl group (C=O) and $Ar^3$.

For example, the electron acceptor moiety of Chemical Formula 1 may be a fused cycle (e.g., fused cyclic structure) of a cyclopentyl group substituted with two carbonyl groups (C=O) and $Ar^3$.

For example, the electron acceptor moiety of Chemical Formula 1 may be a fused cycle (e.g., fused cyclic structure) of one carbonyl group (C=O), and a cyclopentyl group substituted with one cyano group or one cyano-containing group, and $Ar^3$.

For example, the electron acceptor moiety of Chemical Formula 1 may be represented by one of Chemical Formulae E-1 to E-3.

[Chemical Formula E-1]

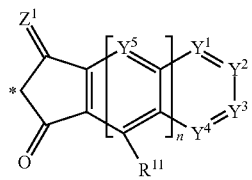

[Chemical Formula E-2]

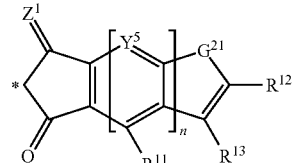

[Chemical Formula E-3]

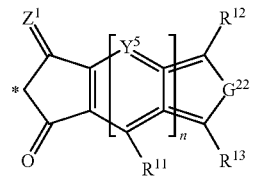

In Chemical Formulae E-1 to E-3, $Z^1$ is O or $CR^bR^c$, wherein $R^b$ and $R^c$ are the same or different and are independently hydrogen, a substituted or unsubstituted C1 to C10 alkyl group, a cyano group, or a cyano-containing group, provided that at least one of $R^b$ and $R^c$ is a cyano group or a cyano-containing group, $Y^1$ to $Y^5$ are the same or different and are independently one of N and $CR^d$, wherein $R^d$ is one of hydrogen and a substituted or unsubstituted C1 to C10 alkyl group, $R^{11}$ to $R^{13}$ are the same or different and are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), a cyano-containing group, and a combination thereof, n is 0 or 1, and $G^{21}$ and $G^{22}$ are independently one of —S—, —Se—, —GeR$^x$R$^y$—, and —Te—, wherein $R^x$ and $R^y$ are the same or different and are independently one of hydrogen, a halogen, a substituted or unsubstituted C1 to C10 alkyl group, and a substituted or unsubstituted C6 to C10 aryl group.

For example, in Chemical Formula E-1, at least one of $Y^1$ to $Y^4$ may be N.

The compound represented by Chemical Formula 1 may be represented by one of Chemical Formulae 1-E to 1-G according to an electron acceptor moiety.

[Chemical Formula 1-E]

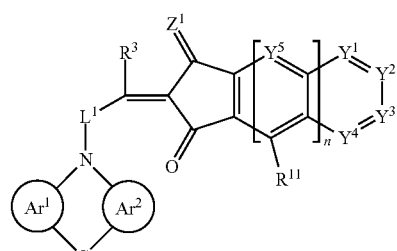

[Chemical Formula 1-F]

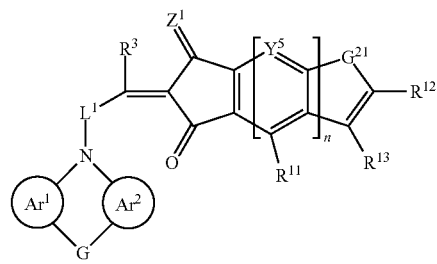

[Chemical Formula 1-G]

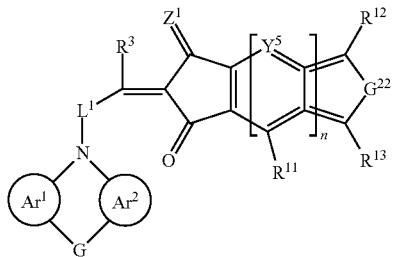

In Chemical Formulae 1-E to 1-G, $L^1$, $Ar^1$, $Ar^2$, G, $R^3$, $Z^1$, $Y^1$ to $Y^5$, $G^{21}$, $G^{22}$, $R^{11}$ to $R^{13}$ are the same as described above.

For example, in Chemical Formula 1-E, at least one of $Y^1$ to $Y^4$ may be N.

The compound represented by Chemical Formula 1 may be for example represented by one of Chemical Formulae 1-H to 1-S4 according to an electron donor moiety and an electron acceptor moiety.

[Chemical Formula 1-H]

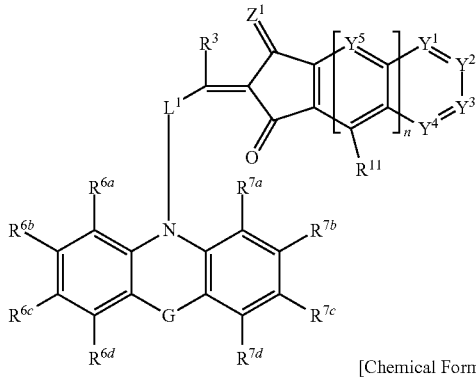

[Chemical Formula 1-I]

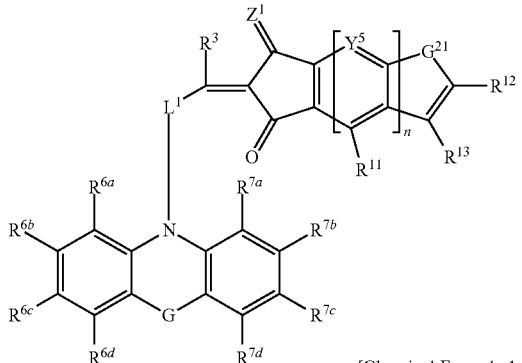

[Chemical Formula 1-J]

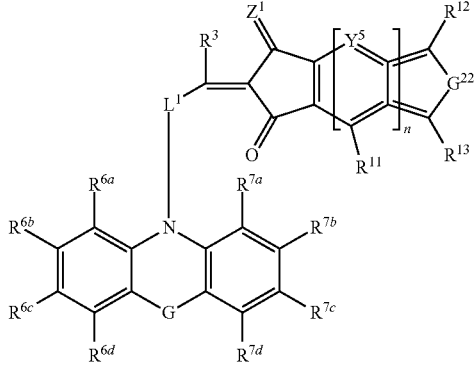

[Chemical Formula 1-K1]

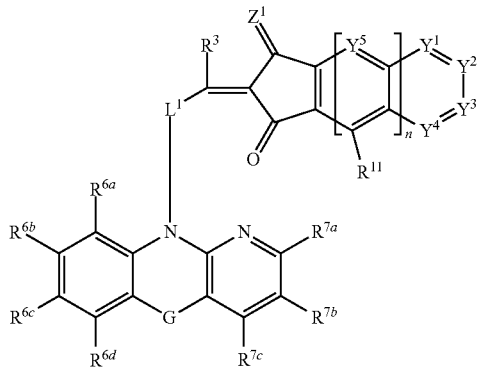

[Chemical Formula 1-L1]

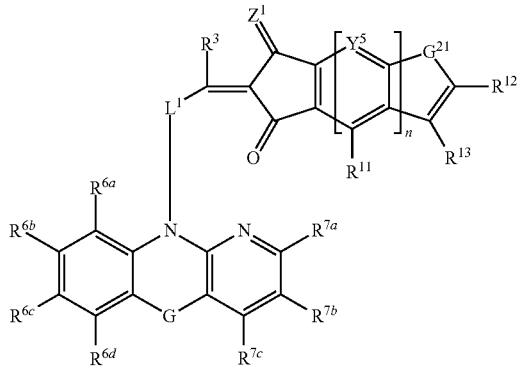

[Chemical Formula 1-M1]

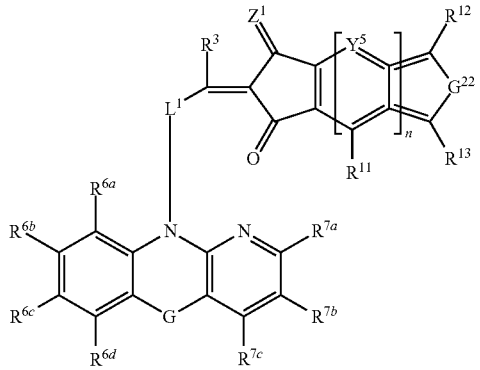

[Chemical Formula 1-K2]

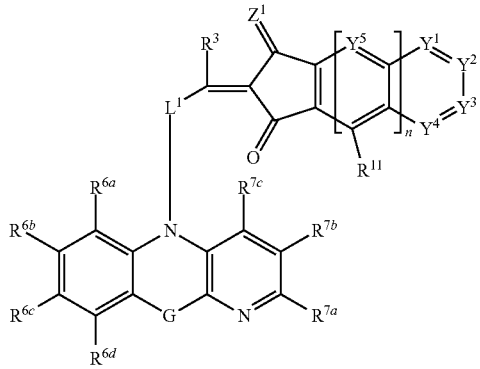

[Chemical Formula 1-L2]
[Chemical Formula 1-M2]
[Chemical Formula 1-N1]
[Chemical Formula 1-O1]
[Chemical Formula 1-P1]
[Chemical Formula 1-N2]
[Chemical Formula 1-O2]
[Chemical Formula 1-P2]
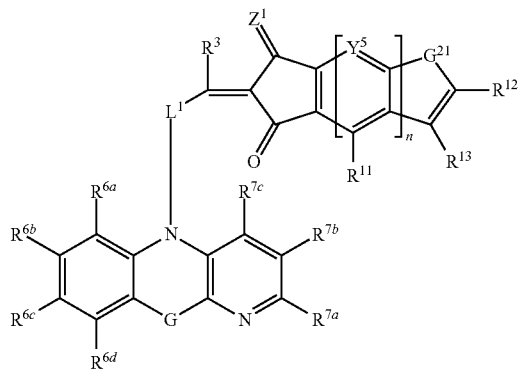
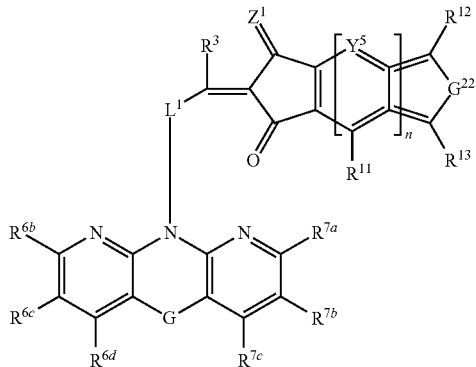

[Chemical Formula 1-Q1]
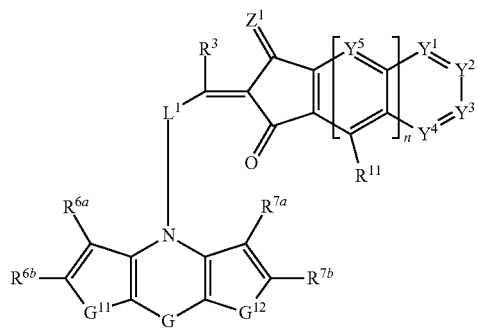
[Chemical Formula 1-R1]
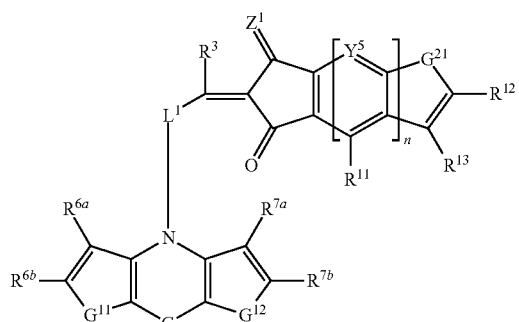
[Chemical Formula 1-S1]
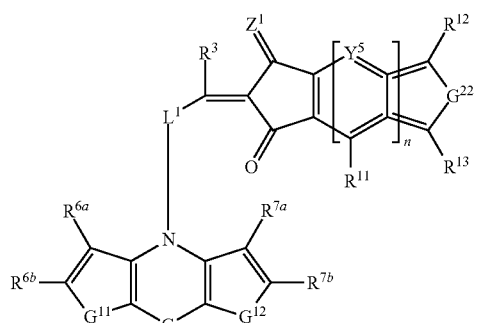
[Chemical Formula 1-Q2]
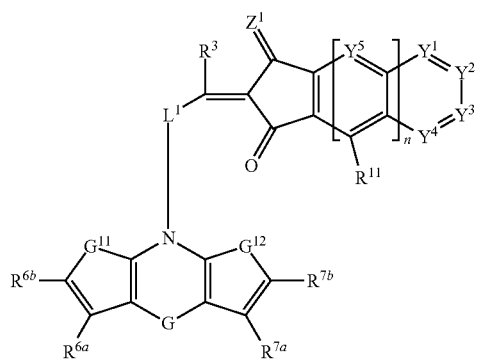
[Chemical Formula 1-R2]
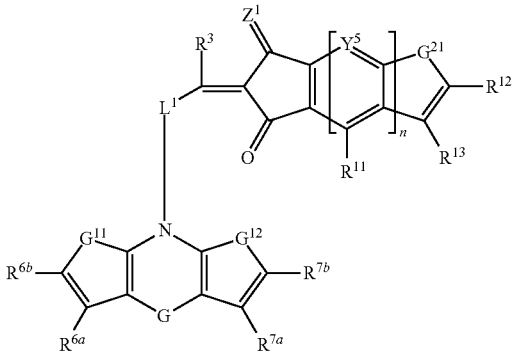
[Chemical Formula 1-S2]
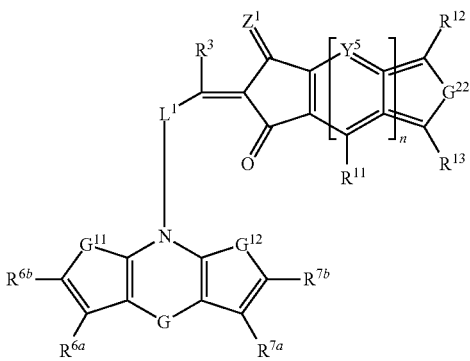
[Chemical Formula 1-Q3]
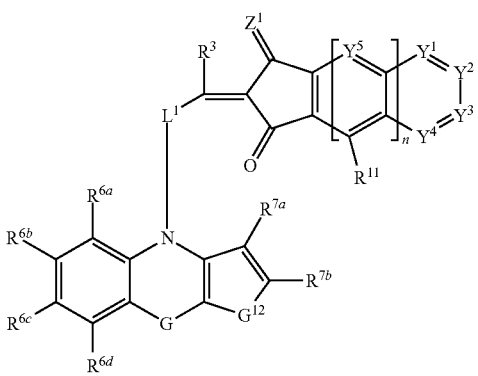
[Chemical Formula 1-R3]
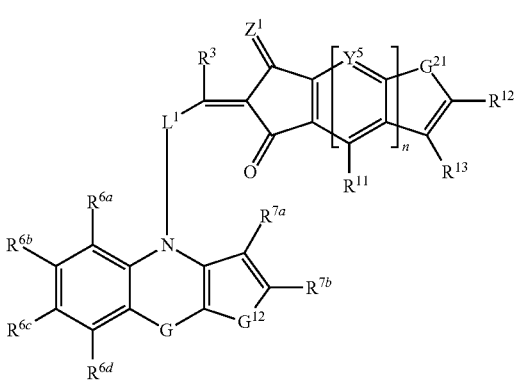

-continued

[Chemical Formula 1-S3]

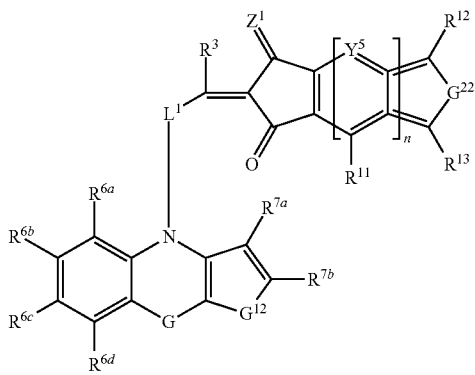

[Chemical Formula 1-Q4]

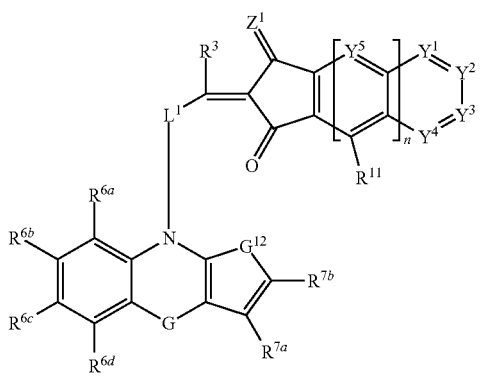

[Chemical Formula 1-R4]

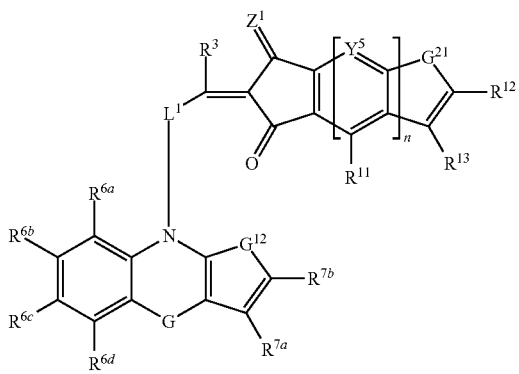

[Chemical Formula 1-S4]

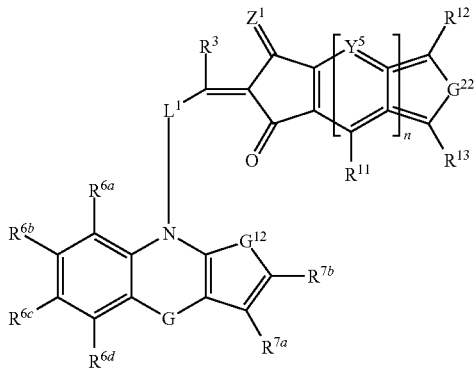

In Chemical Formulae 1-H to 1-S4, $L^1$, $R^3$, G, $G^{11}$, $G^{12}$, $R^{6a}$ to $R^{6d}$, $R^{7a}$ to $R^{7d}$, $Z^1$, $Y^1$ to $Y^5$, $R^{11}$ to $R^{13}$, n, $G^{21}$, and $G^{22}$ are the same as described above.

For example, the compound represented by Chemical Formula 1 may be represented by Chemical Formula 1-T.

[Chemical Formula 1-T]

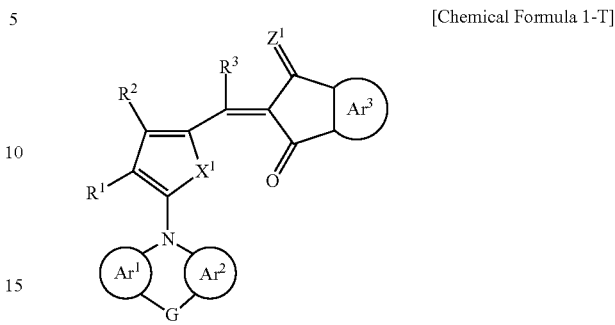

In Chemical Formula 1-T, $X^1$ is one of —Se—, —Te—, —O—, —S(=O)—, —S(=O)$_2$—, —NR$^a$—, —SiR$^b$R$^c$—, and —GeR$^d$R$^e$—, wherein R$^a$, R$^b$, R$^c$, R$^d$, and R$^e$ are the same or different and are independently one of hydrogen and a substituted or unsubstituted C1 to C10 alkyl group, $Ar^3$ is a substituted or unsubstituted C6 to C30 arylene group, a substituted or unsubstituted C6 to C30 arene group, a substituted or unsubstituted heterocyclic group including at least one hetero atom selected from S, Se, Te, Ge, N, and a combination thereof, and a condensed ring of two or more of the foregoing rings, $R^1$ to $R^3$ are the same or different and are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, each of $Ar^1$ and $Ar^2$ are the same or different and are independently one of a substituted or unsubstituted C6 to C30 arylene group, a substituted or unsubstituted C6 to C30 arene group, and a substituted or unsubstituted C3 to C30 heterocyclic group, and G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, and R$^k$ and R$^l$, R$^m$ and R$^n$, and R$^o$ and R$^p$ are independently present or linked with each other to provide a ring (e.g., fused cyclic structure), and k is one of 1 and 2.

The compound represented by Chemical Formula 1-T may be for example one of compounds of Group 2.

[Group 2]

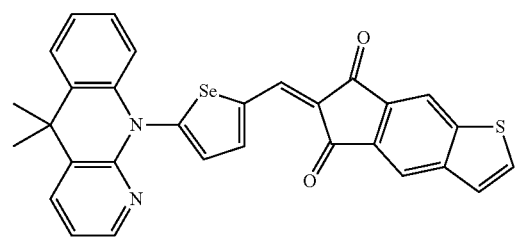

57
-continued
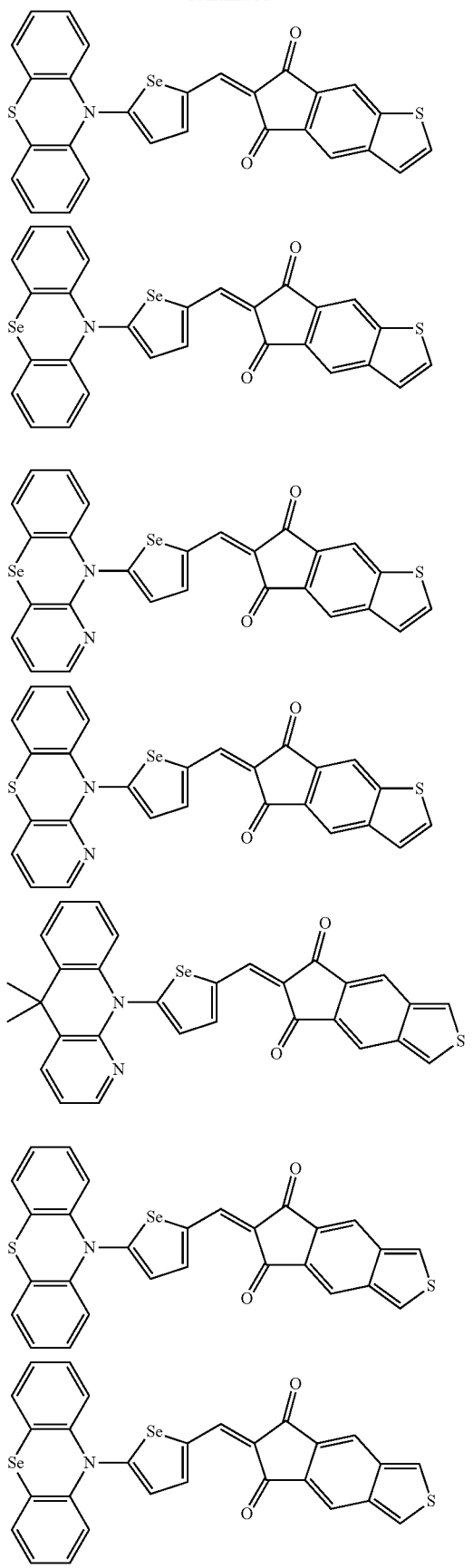
58
-continued
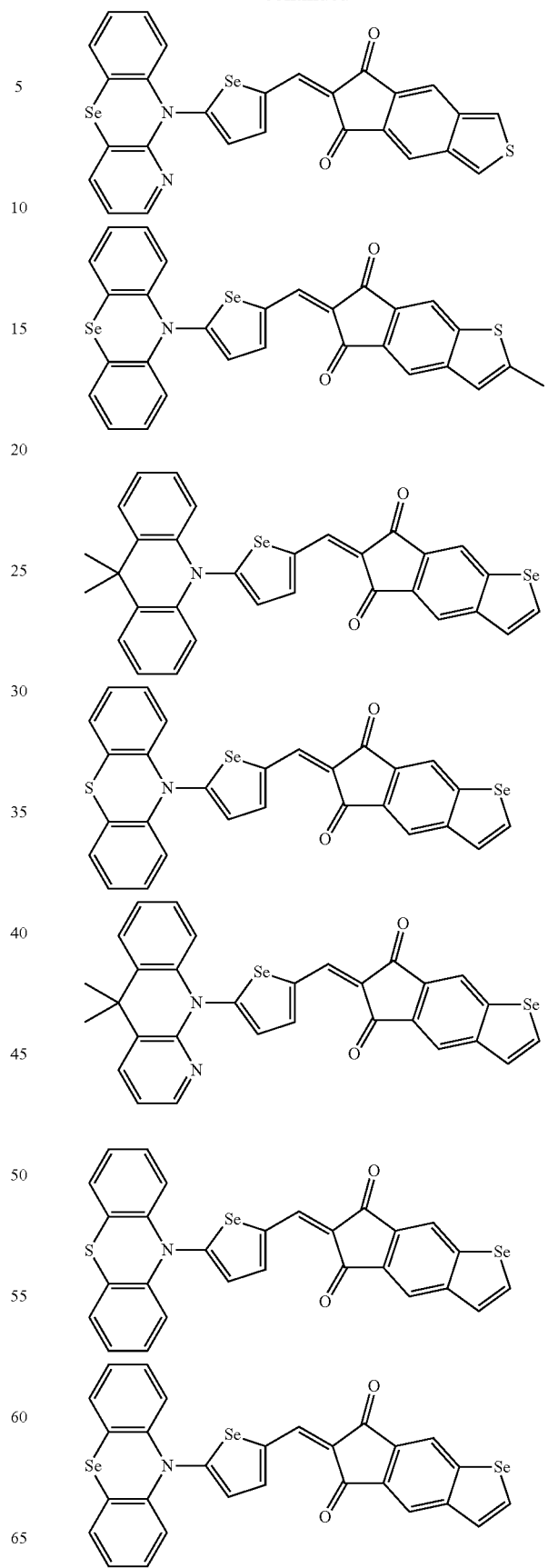

59
-continued
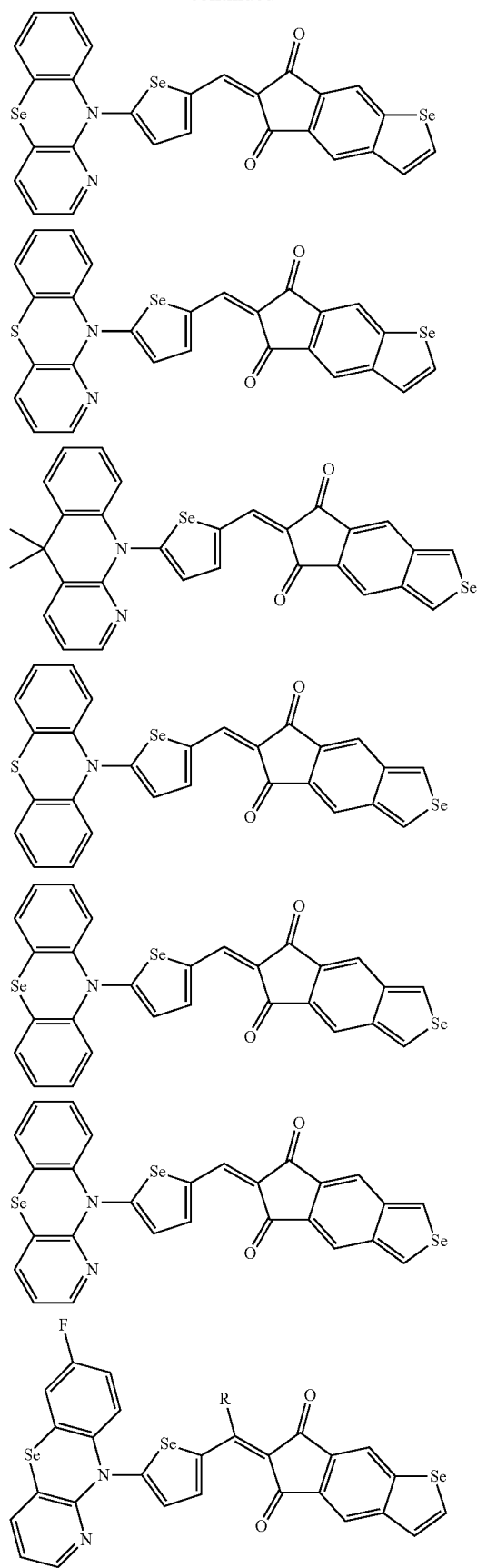
60
-continued
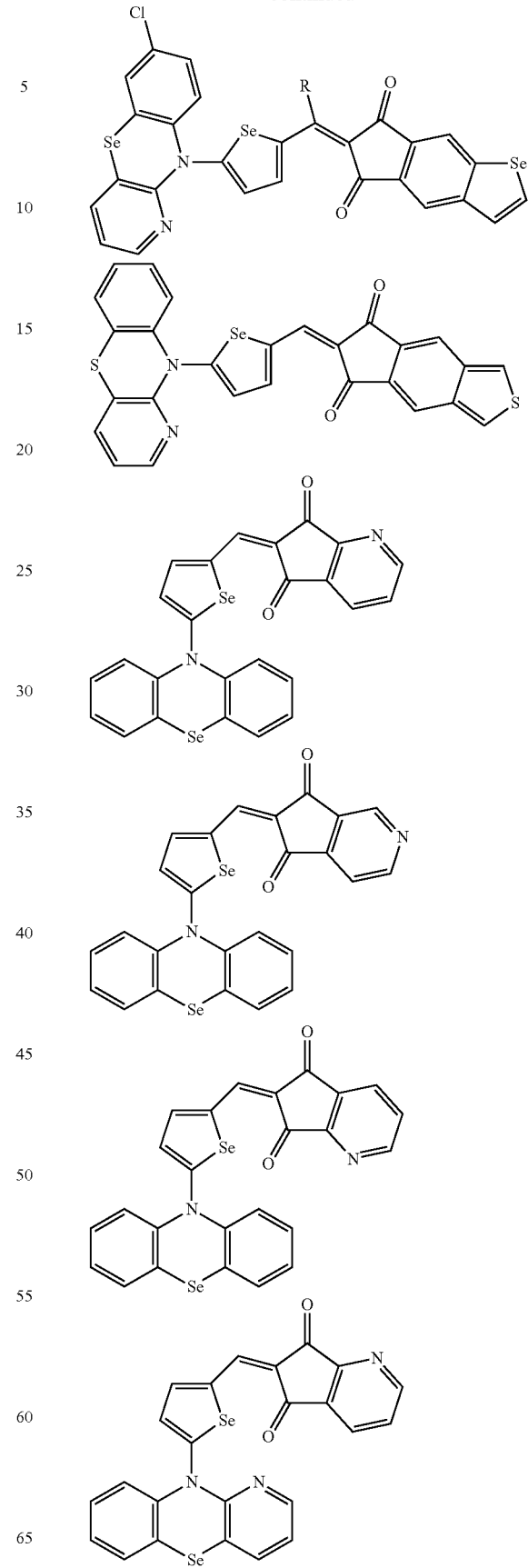

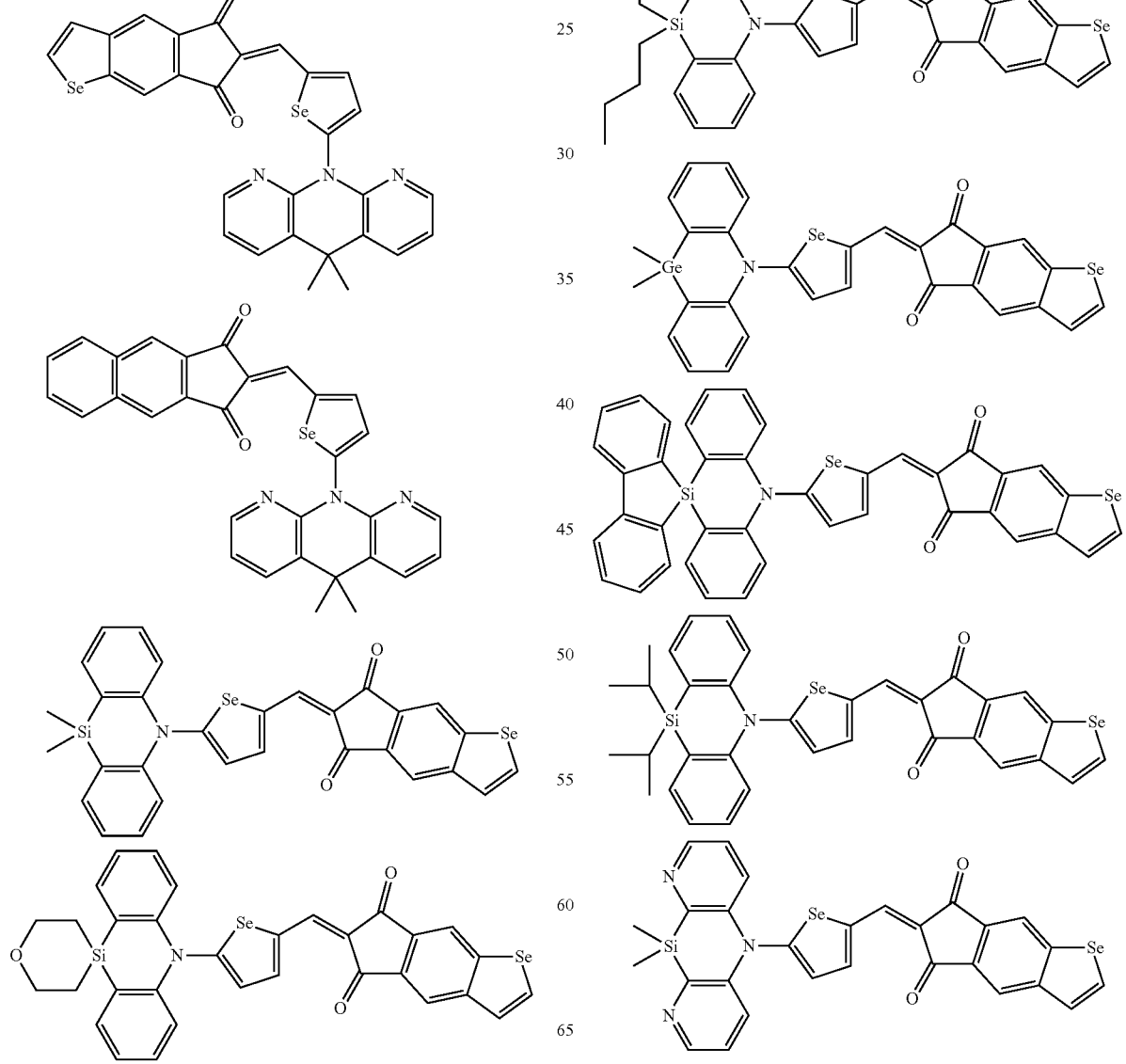

63
-continued
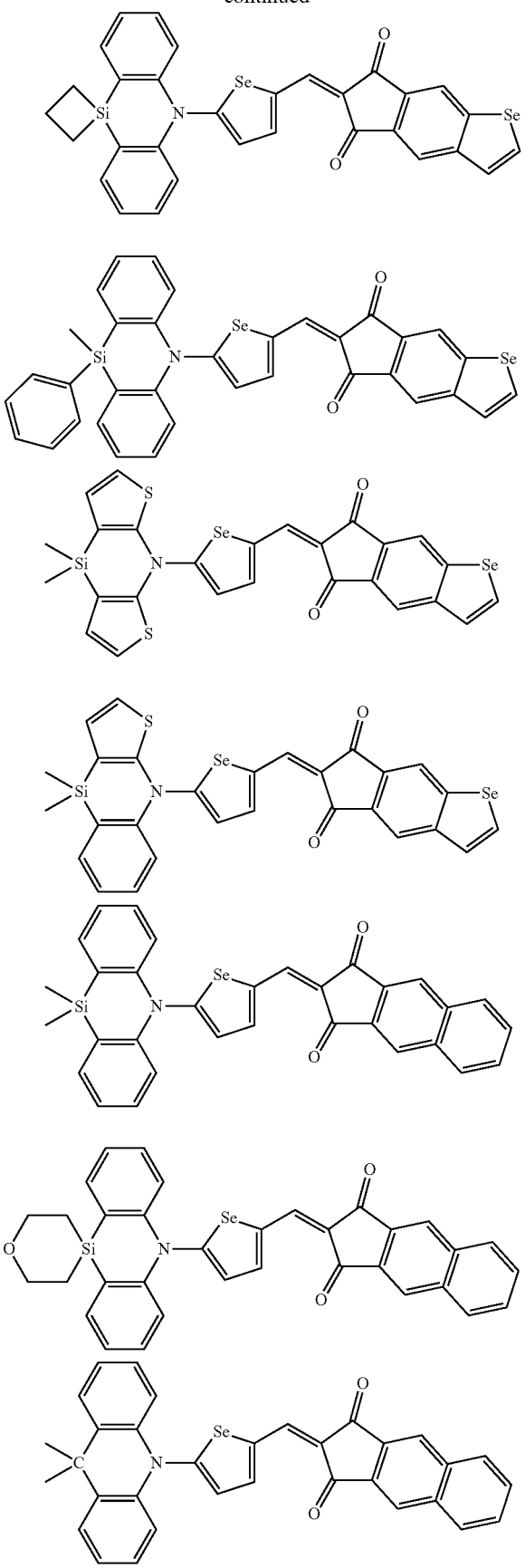
64
-continued
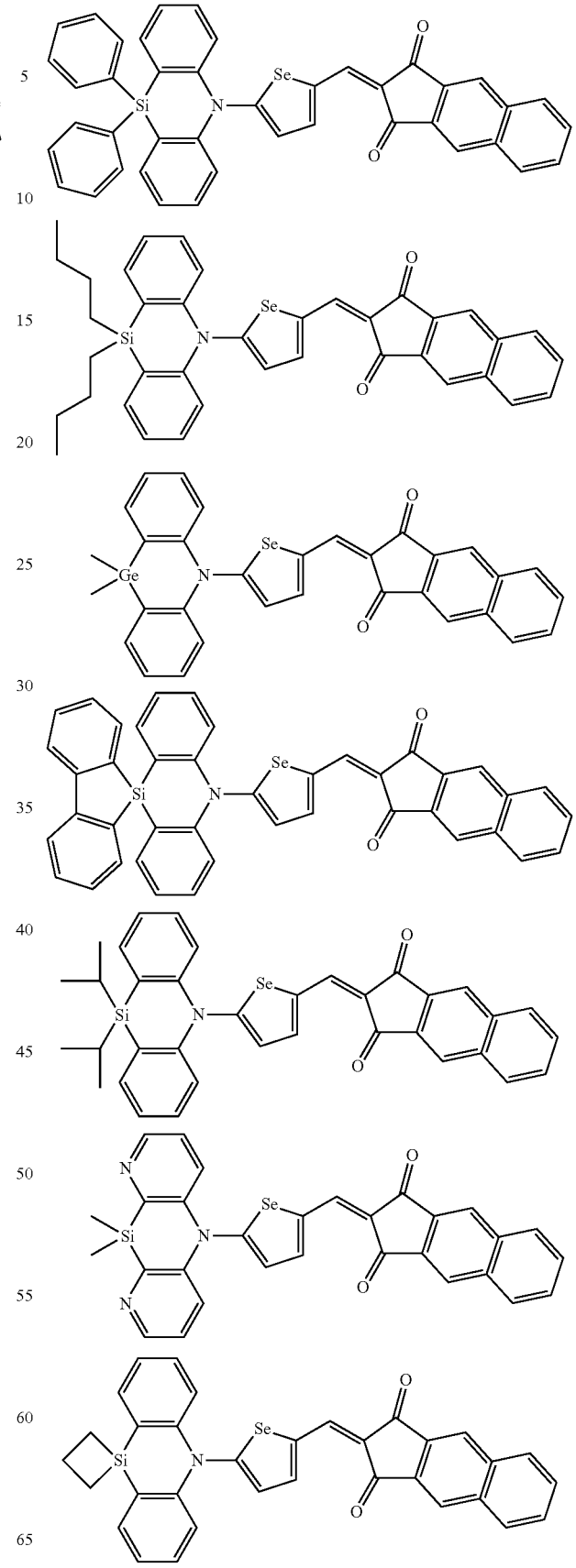

65
-continued
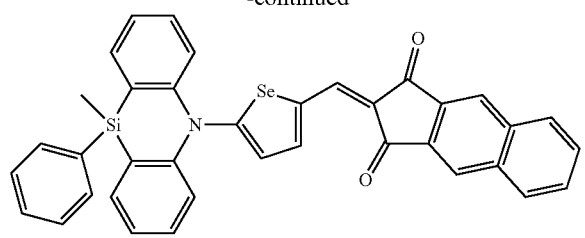
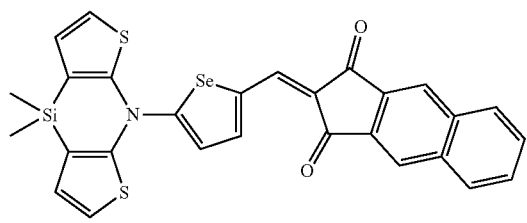
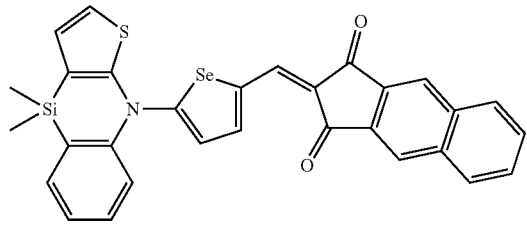
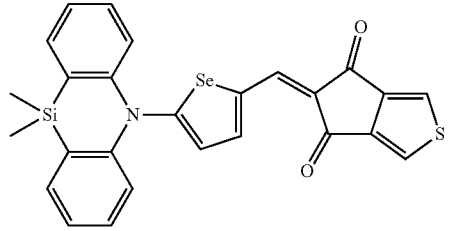
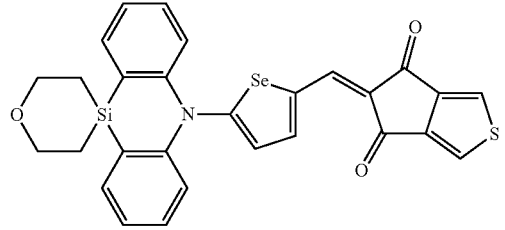
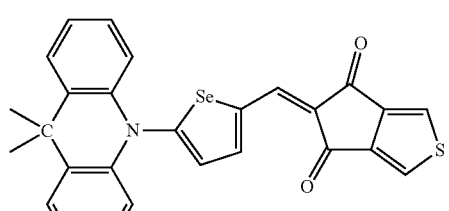
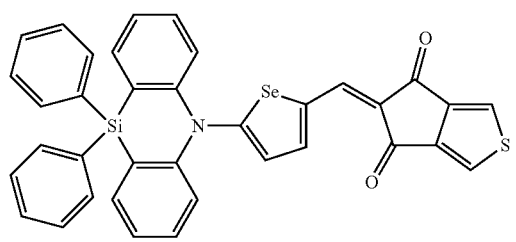
66
-continued
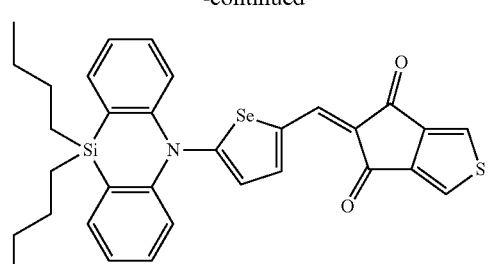
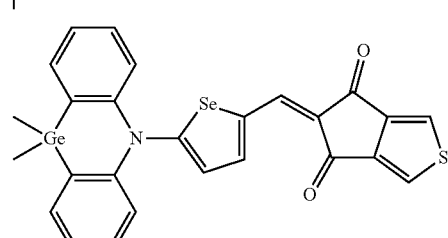
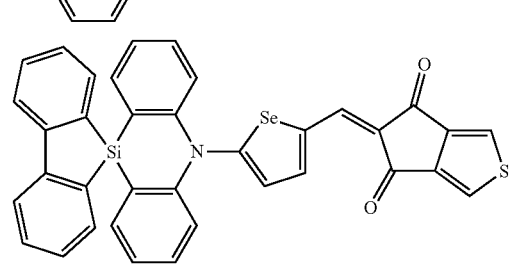
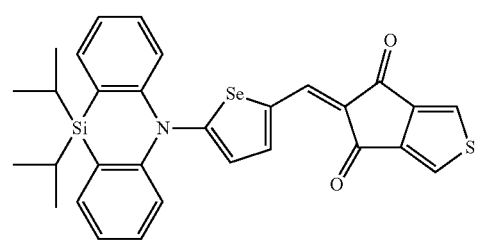
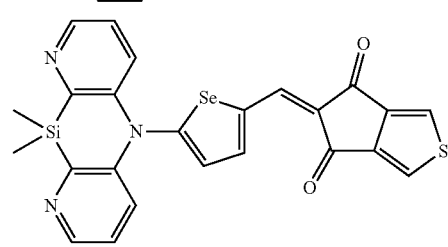
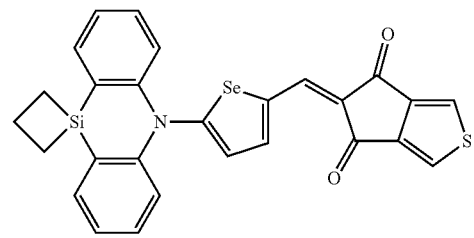
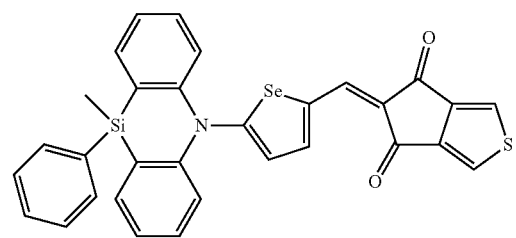

67
-continued
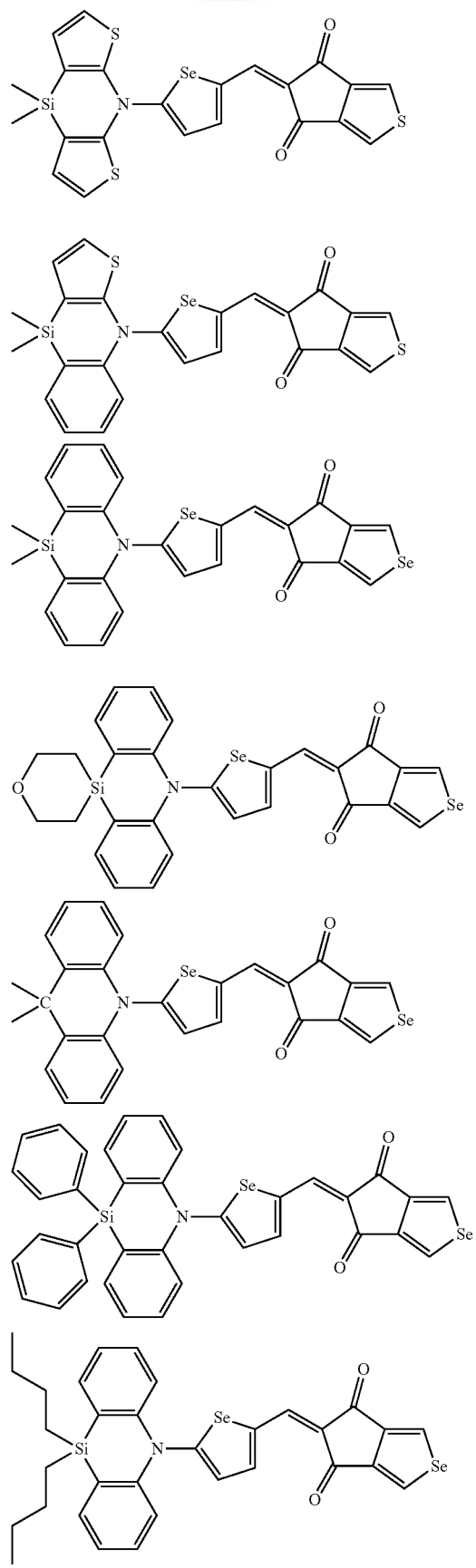
68
-continued
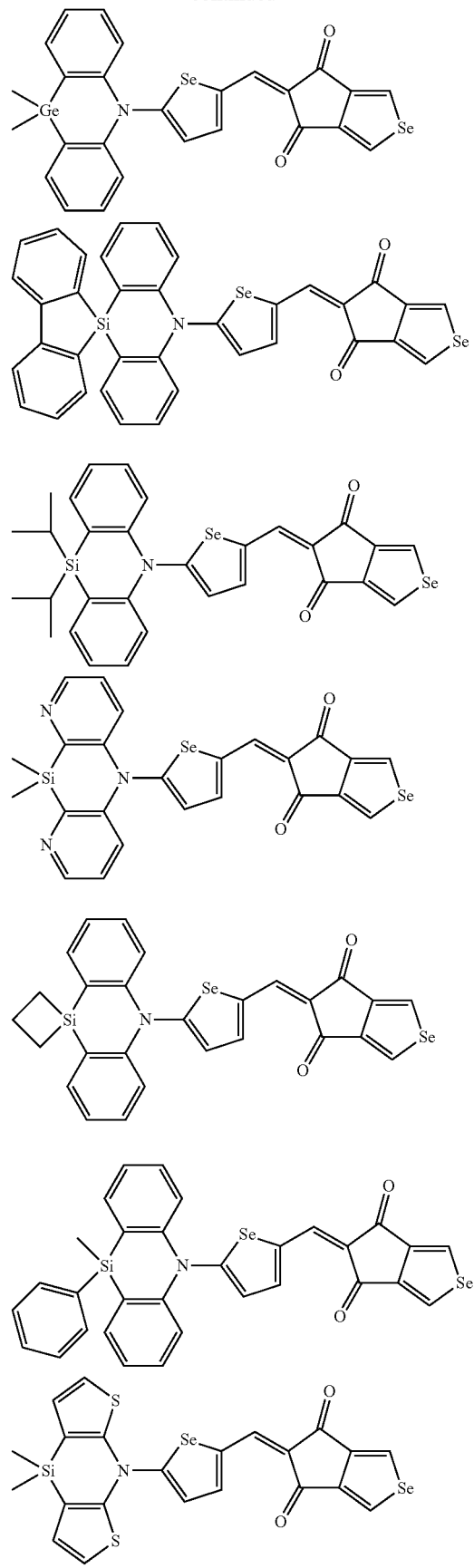

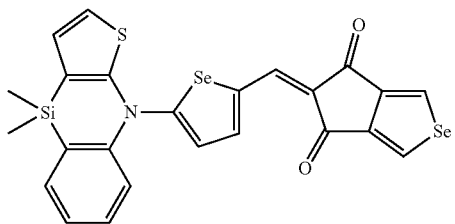

For example, the compound represented by Chemical Formula 1 may be represented by Chemical Formula 1-U.

[Chemical Formula 1-U]

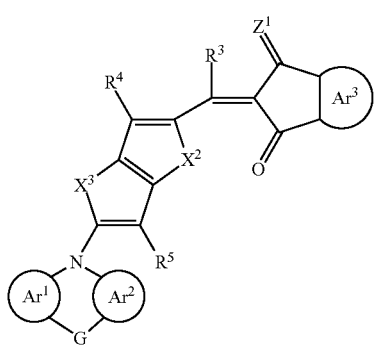

In Chemical Formula 1-U,

X² and X³ are the same or different and are independently one of —S—, —Se—, —Te—, —O—, —S(=O)—, —S(=O)₂—, —NR$^a$—, —SiR$^b$R$^c$—, and —GeR$^d$R$^e$—, wherein R$^a$, R$^b$, R$^c$, R$^d$, and R$^e$ are the same or different and are independently one of hydrogen and a substituted or unsubstituted C1 to C10 alkyl group, Ar¹ to Ar³ are the same or different and are independently one of a substituted or unsubstituted C6 to C30 arylene group, a substituted or unsubstituted C6 to C30 arene group, a substituted or unsubstituted C3 to C30 heterocyclic group, and a condensed ring of two or more of the foregoing rings, R¹ to R³ are the same or different and are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, R$^k$ and R$^l$, R$^m$ and R$^n$, and R$^o$ and R$^p$ are independently present or linked with each other to provide a ring (e.g., fused cyclic structure), and k is one of 1 and 2.

The compound represented by Chemical Formula 1-U may be for example one of compounds of Group 3.

[Group 3]

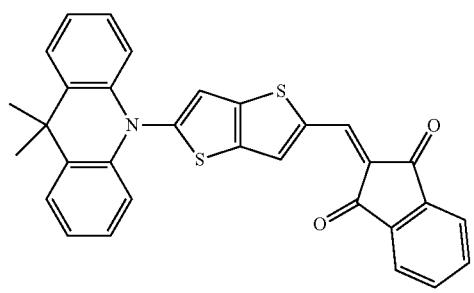

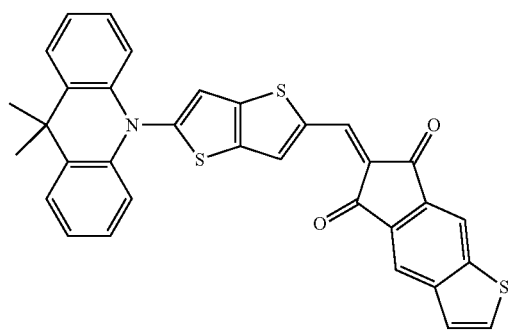

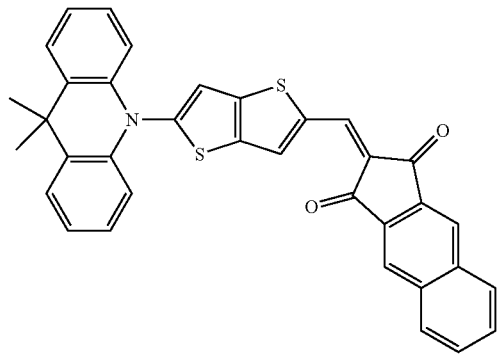

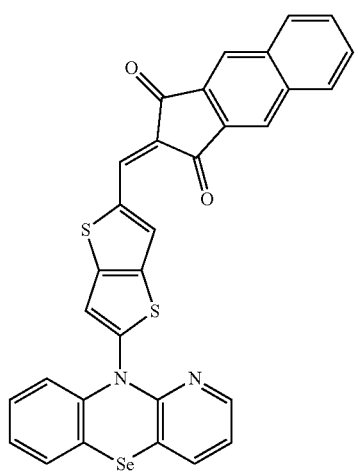

-continued

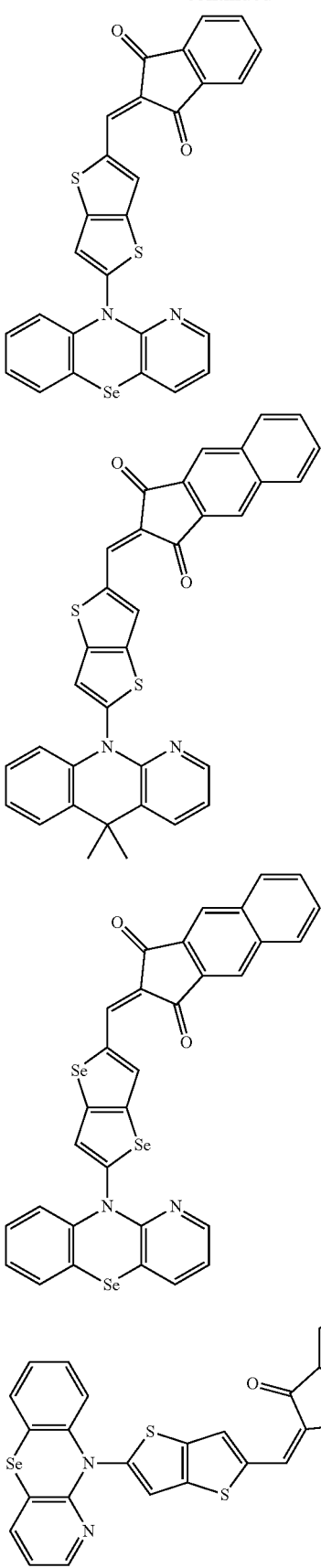

-continued

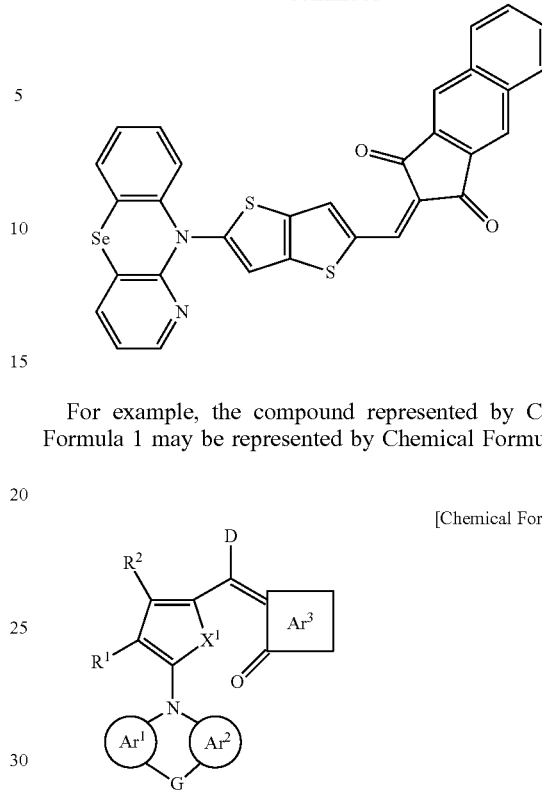

For example, the compound represented by Chemical Formula 1 may be represented by Chemical Formula 1-V.

[Chemical Formula 1-V]

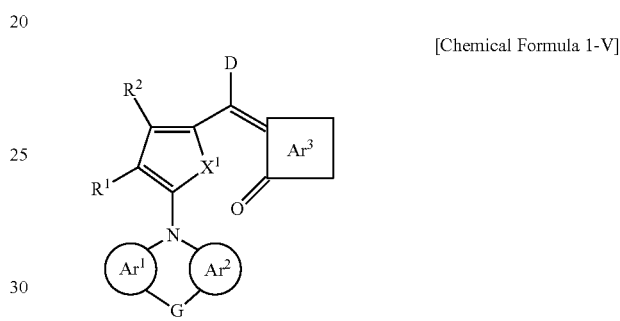

In Chemical Formula 1-V, $X^1$ is one of —Se—, —Te—, —O—, —S(=O)—, —S(=O)$_2$—, —NR$^a$—, —SiR$^b$R$^c$—, and —GeR$^d$R$^e$—, wherein R$^a$, R$^b$, R$^c$, R$^d$, and R$^e$ are the same or different and are independently one of hydrogen and a substituted or unsubstituted C1 to C10 alkyl group, D is deuterium, Ar$^1$ to Ar$^3$ are the same or different and are independently one of a substituted or unsubstituted C6 to C30 arylene group, a substituted or unsubstituted C6 to C30 arene group, a substituted or unsubstituted C3 to C30 heterocyclic group, and a condensed ring of two or more of the foregoing rings, R$^1$ and R$^2$ are the same or different and are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G is one of a single bond, —O—, —S—, —Se—, —N=, —(CR$^f$R$^g$)$_k$—, —NR$^h$—, —SiR$^i$R$^j$—, —GeR$^k$R$^l$—, and —(C(R$^m$)=C(R$^n$))—, wherein R$^f$, R$^g$, R$^h$, R$^i$, R$^j$, R$^k$, R$^l$, R$^m$, and R$^n$ are the same or different and are independently one of hydrogen, a halogen, a substituted or unsubstituted C1 to C10 alkyl group, and a substituted or unsubstituted C6 to C12 aryl group, and R$^m$ and R$^n$ are independently present or linked with each other to provide a fused cycle (e.g., fused cyclic structure) and k is 1 or 2.

For example, the compound represented by Chemical Formula 1-V may be obtained by reacting an electron donor substituted with deuterium-linker compound (1) with an electron acceptor compound as shown in Reaction Scheme A.

[Reaction Scheme A]
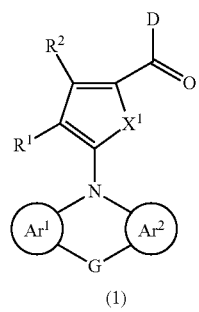
(1)
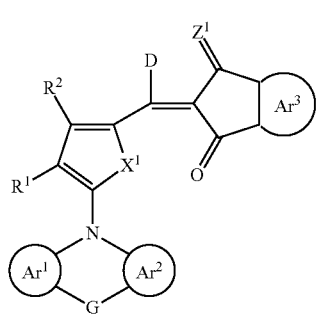
For example, the compound represented by Chemical Formula 1-V may be obtained by replacing hydrogen of a linker by deuterium as shown in Reaction Scheme B.
[Reaction Scheme B]
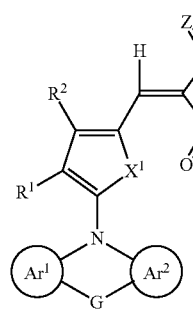
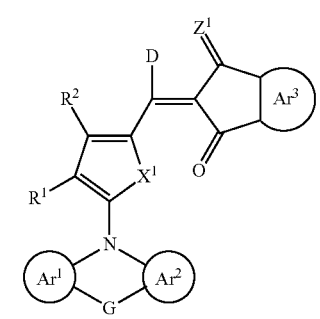
The compound represented by Chemical Formula 1-V may be for example one of compounds of Group 4.
[Group 4]
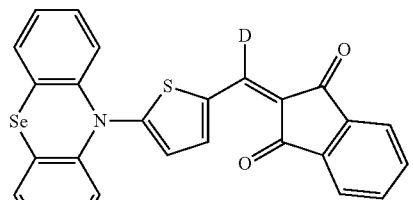
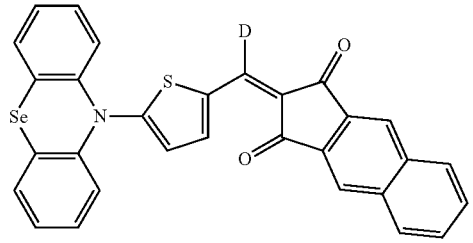
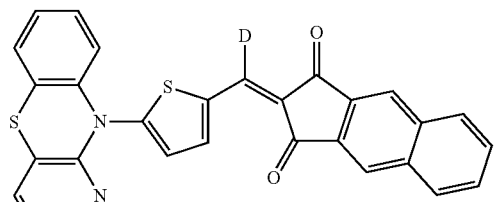
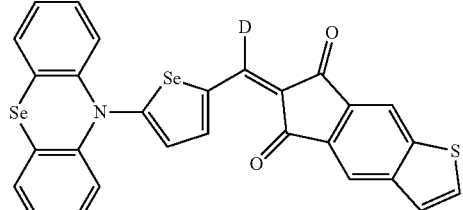
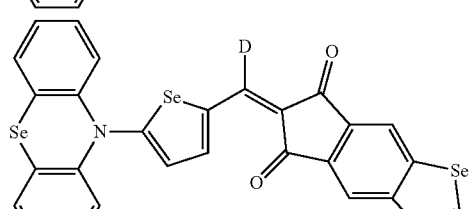
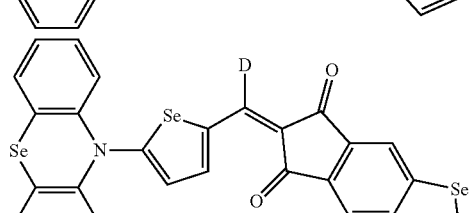
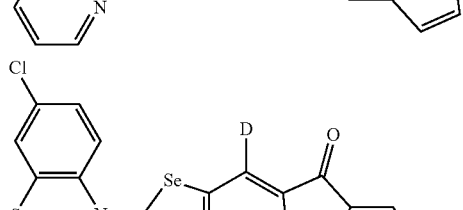

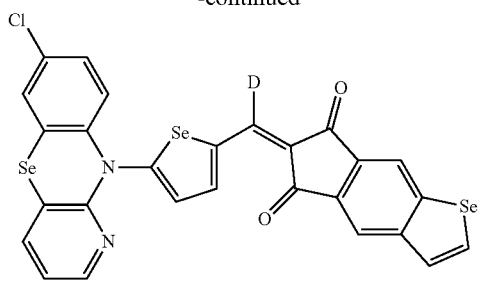
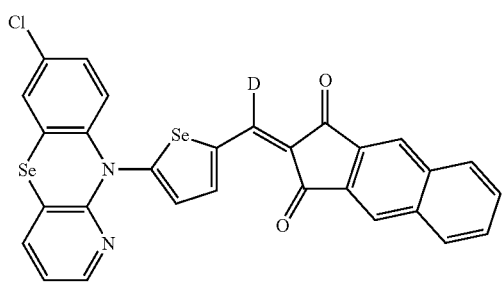
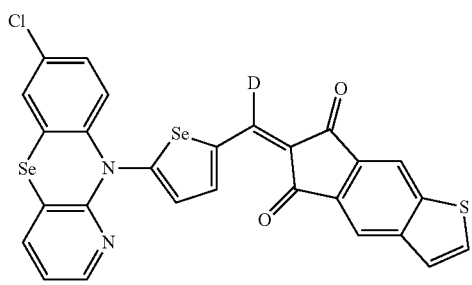
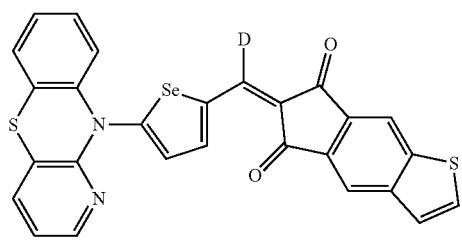
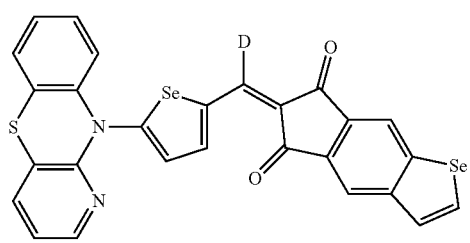
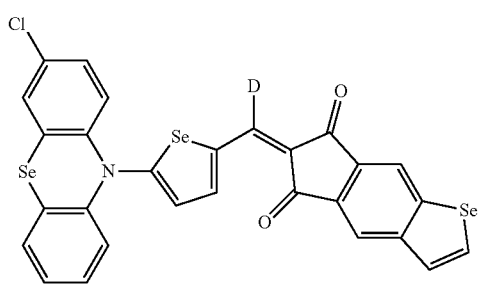
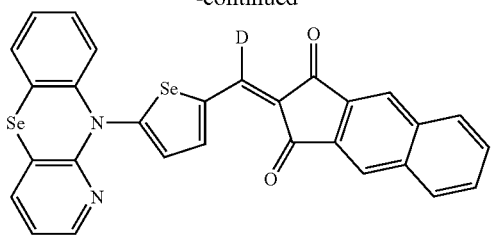
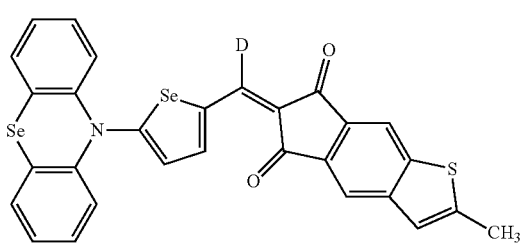
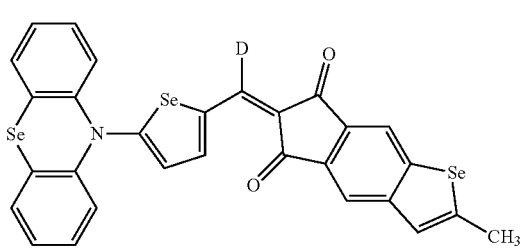
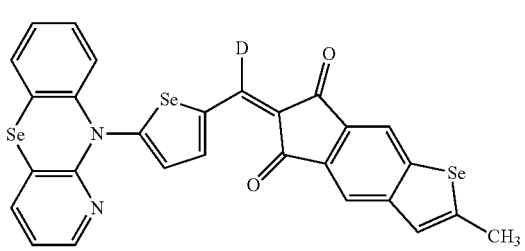
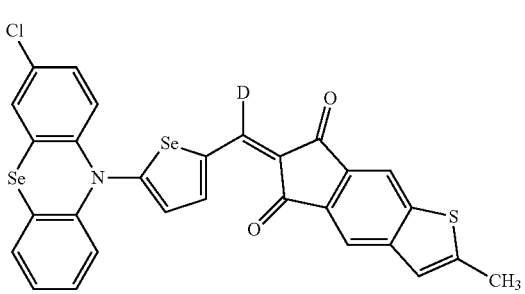
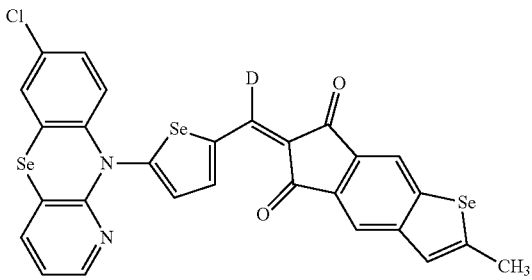 [SMILES: [2H]/C(=C1/C(=O)c2cc3cc(C)[se]c3cc2C1=O)c1ccc(N2c3ccc(Cl)cc3[Se]c3cccnc32)[se]1]
For example, the compound represented by Chemical Formula 1 may be represented by Chemical Formula 1-W.

[Chemical Formula 1-W]

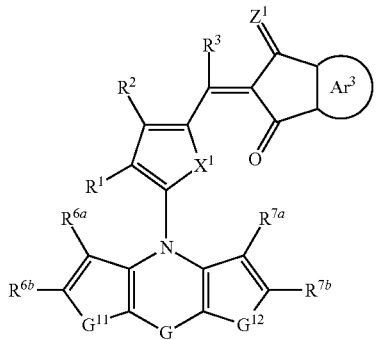

[Group 5]

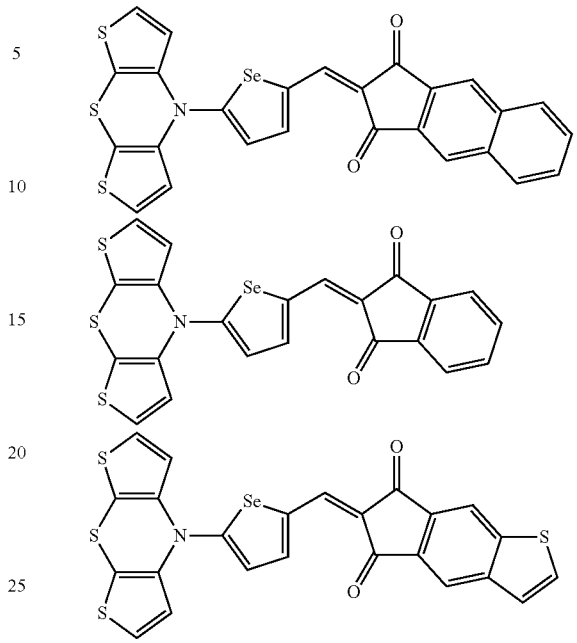

In Chemical Formula 1-W,

X$^1$ is one of —Se—, —Te—, —O—, —S(=O)—, —S(=O)$_2$—, —NR$^a$—, —SiR$^b$R$^c$—, and —GeR$^d$R$^e$—, wherein R$^a$, R$^b$, R$^c$, R$^d$, and R$^e$ are the same or different and are independently one of hydrogen and a substituted or unsubstituted C1 to C10 alkyl group, Ar$^3$ is one of a substituted or unsubstituted C6 to C30 arylene group, a substituted or unsubstituted C6 to C30 arene group, a substituted or unsubstituted C3 to C30 heterocyclic group, and a condensed ring of two or more of the foregoing rings, R$^1$ to R$^3$ are the same or different and are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and R$^i$ and R$^j$, and R$^k$ and R$^l$, R$^m$ and R$^n$, and R$^o$ and R$^p$ are independently present or linked with each other to provide a ring (e.g., fused cyclic structure), and k is one of 1 and 2.

G$^{11}$ and G$^{12}$ are the same or different and are independently one of —S—, —Se—, —Te—, —GeR$^x$R$^y$—, and —CR$^z$R$^w$—, wherein R$^x$, R$^y$, R$^z$, and R$^w$ are the same or different and are independently one of hydrogen, a halogen, a substituted or unsubstituted C1 to C10 alkyl group, and a substituted or unsubstituted C6 to C10 aryl group, R$^{6a}$ and R$^{6b}$ and R$^{7a}$ and R$^{7b}$ are the same or different and are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, R$^{6a}$ and R$^{6b}$ are independently present or linked with each other to provide a fused cycle (e.g., fused cyclic structure), and R$^{7a}$ and R$^{7b}$ are independently present or linked with each other to provide a fused cycle (e.g., fused cyclic structure).

The compound represented by Chemical Formula 1-W may be for example one of compounds of Group 5.

The compound may have a maximum absorption wavelength ($\lambda_{max}$) of greater than or equal to about 510 nm and less than or equal to about 565 nm in a thin film state. Within the range, it may have for example a maximum absorption wavelength ($\lambda_{max}$) of about 520 nm to about 560 nm, for example about 520 nm to about 565 nm. The thin film may be a thin film obtained by deposition under a vacuum condition.

The compound may have a full width at half maximum (FWHM) of about 50 nm to about 120 nm in a thin film state. Herein, the FWHM is a width of a wavelength corresponding to half of a maximum absorption point. When the full width at half maximum (FWHM) is small, wavelength selectivity is increased by selectively absorbing light in a narrow wavelength region. When the FWHM is within the range, selectivity in a green wavelength region may be increased. The thin film may be a thin film obtained by deposition under a vacuum condition.

The compound has a relatively high melting point (Tm) and thus may be effectively formed into a thin film by a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. From this view, the compound may have a higher melting point than the deposition temperature and for example when a melting point of the compound is Tm and a deposition temperature is Ts, the melting point may satisfies Tm−Ts≥10° C.

Illustrated in more detail, the compound is a donor-acceptor material including both an electron donor moiety and an electron acceptor moiety, and in general, the donor-acceptor material has sufficient charge transfer characteristics but weak thermal characteristics and thus may be easily thermally decomposed during deposition. This compound having weak thermal characteristics is thermally decomposed during deposition and thus may not only deteriorate performance of a device but also the performance of the device again when exposed to a relatively high temperature (about 160° C.) in a subsequent process such as a micro lens array (MLA) and resultantly, cause a morphology change of a thin film.

The compound has a structure capable of improving thermal characteristics despite a donor-acceptor material and thus may increase thermal stability. Accordingly, when the compound is applied to a device, charge transfer characteristics and thermal properties may be simultaneously satisfied.

The compound may be for example applied to a device as a p-type semiconductor or an n-type semiconductor. For example, the compound may be used as a p-type semiconductor. For example, the compound may be used with fullerene or a fullerene derivative. Because an LUMO energy level of the fullerene is about 4.2 eV, the compound may have a higher energy level than about 4.2 eV. A HOMO energy level of the compound may be about 5.0 eV to about 5.8 eV and an LUMO energy level of the compound may be about 2.7 eV to about 3.9 eV, and an energy bandgap of the compound may be about 1.9 eV to about 2.3 eV. The compound having a HOMO level, an LUMO level, and an energy bandgap within the ranges may be used as a p-type or n-type semiconductor effectively absorbing light in a green wavelength region, and thus has high external quantum efficiency (EQE) and resultantly improves photoelectric conversion efficiency.

For example, the compound may have a molecular weight of about 300 to about 1500 g/mol. Within the range, it may be stably deposited. However, the compound may be formed into a film by a solution process in addition to the deposition method.

The compound may be formed into a thin film which may be applied to various devices and electronic devices.

For example, the compound may be applied to a photoelectric device.

Hereinafter, a photoelectric device according to an example embodiment is described with reference to drawings.

FIG. 1 is a cross-sectional view showing a photoelectric device according to an example embodiment.

Referring to FIG. 1, a photoelectric device 100 according to an example embodiment includes a first electrode 10 and a second electrode 20, and an organic layer between the first electrode 10 and the second electrode 20. The organic layer includes an active layer 30.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of for example an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound which may be for example used as a p-type semiconductor or an n-type semiconductor. For example, the compound may be used as a p-type semiconductor.

The compound is a compound selectively absorbing light in a green wavelength region, and the active layer 30 including the compound may have a maximum absorption wavelength ($\lambda_{max}$) in a wavelength region of about 500 nm to about 600 nm, specifically about 520 nm to about 565 nm.

The active layer 30 may exhibit a light absorption curve having a relatively narrow full width at half maximum (FWHM) of about 50 nm to about 120 nm, for example about 50 nm to about 100 nm. Accordingly, the active layer 30 has high selectivity for light in a green wavelength region.

For example, the active layer 30 may include fullerene or fullerene derivative as an n-type semiconductor and the compound. The active layer 30 may include the compound and fullerene or the fullerene derivative in a volume ratio of about 0.9:1 to about 1.1:1, for example 1:1 and may have an absorption coefficient of greater than or equal to about $5.5 \times 10^4$ cm$^{-1}$, for example about $5.8 \times 10^4$ cm$^{-1}$ to about $2 \times 10^5$ cm$^{-1}$ or about $7.0 \times 10^4$ cm$^{-1}$ to about $2 \times 10^5$ cm$^{-1}$.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as an alkyl group, an aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

For example, the active layer 30 may include sub-phthalocyanine or a sub-phthalocyanine derivative, thiophene or a thiophene derivative, or a combination thereof as an n-type semiconductor.

The sub-phthalocyanine or the sub-phthalocyanine derivative may be represented by Chemical Formula X.

[Chemical Formula X]

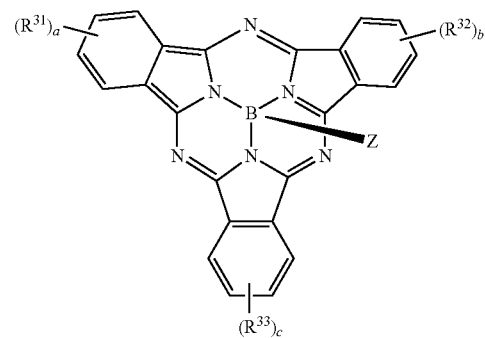

In Chemical Formula X, $R^{31}$ to $R^{33}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, and a combination thereof, a, b, and c are an integer ranging from 1 to 3, and Z is a monovalent substituent.

For example, Z may be a halogen or a halogen-containing group, for example F, Cl, a F-containing group, or a Cl-containing group.

The halogen may refer to F, Cl, Br, or I, and the halogen-containing group may refer to an alkyl group where at least one of hydrogen is replaced by F, Cl, Br, or I.

The thiophene derivative may be for example represented by Chemical Formula Y or Chemical Formula Z, but is not limited thereto.

[Chemical Formula Y]

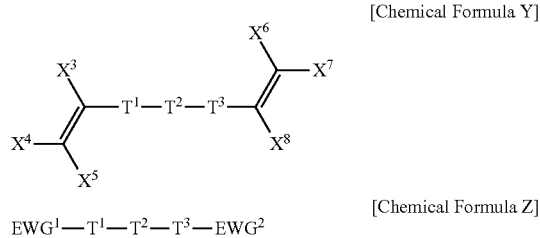

[Chemical Formula Z]

$EWG^1-T^1-T^2-T^3-EWG^2$

In Chemical Formulae Y and Z, each of $T^1$, $T^2$, and $T^3$ is aromatic rings including substituted or unsubstituted thiophene moieties, each of $T^1$, $T^2$, and $T^3$ are independently present or are fused to each other, each of $X^3$ to $X^8$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ are independently an electron withdrawing group.

For example, in Chemical Formula Y, at least one of $X^3$ to $X^8$ is an electron withdrawing group, for example a cyano group or a cyano-containing group.

The active layer 30 may further include a second p-type semiconductor compound selectively absorbing green light. The p-type semiconductor compound may be a compound represented by Chemical Formula W, but is not limited thereto.

[Chemical Formula W]

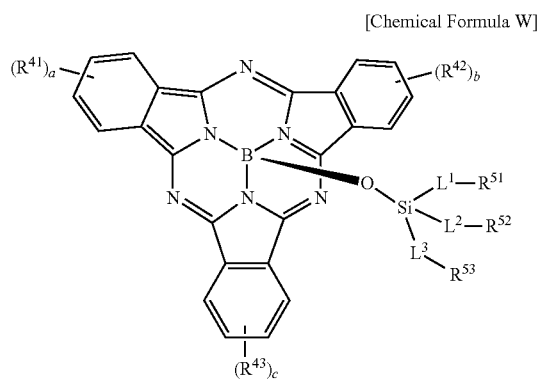

In Chemical Formula W, each of $R^{41}$ to $R^{43}$ are independently one of hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C6 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or adjacent two groups of $R^{41}$ to $R^{43}$ are optionally fused to each other to provide a ring, each of $L^1$ to $L^3$ are independently a single bond, a substituted or unsubstituted C1 to C30 alkylene group, a substituted or unsubstituted C6 to C30 arylene group, a substituted or unsubstituted C6 to C30 arene group, divalent substituted or unsubstituted C3 to C30 heterocyclic group, or a combination thereof, each of $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and each of a to c are independently an integer ranging from 0 to 4 (and/or 1 to 4).

The second p-type semiconductor compound selectively absorbing green light may be included in an amount of about 500 to about 1500 parts by weight based on 100 parts by weight of the compound.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the p-type semiconductor and the n-type semiconductor in a thickness ratio (or volume ratio) of about 1:100 to about 100:1. Within the range, they may be included in a thickness ratio (or volume ratio) ranging from about 1:50 to about 50:1 within the range, specifically, about 1:10 to about 10:1, and more specifically, about 1:1. When they have a composition ratio within the range, an exciton may be effectively produced and a pn junction may be effectively formed.

The p-type layer may include the compound and the n-type layer may include the n-type semiconductor.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency. In the photoelectric device 100, when light enters from the first electrode 10 and/or second electrode 20 and the active layer 30 absorbs light in a predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the organic photoelectric device.

Hereinafter, a photoelectric device according to another example embodiment is described with reference to FIG. 2.

Figure 2:
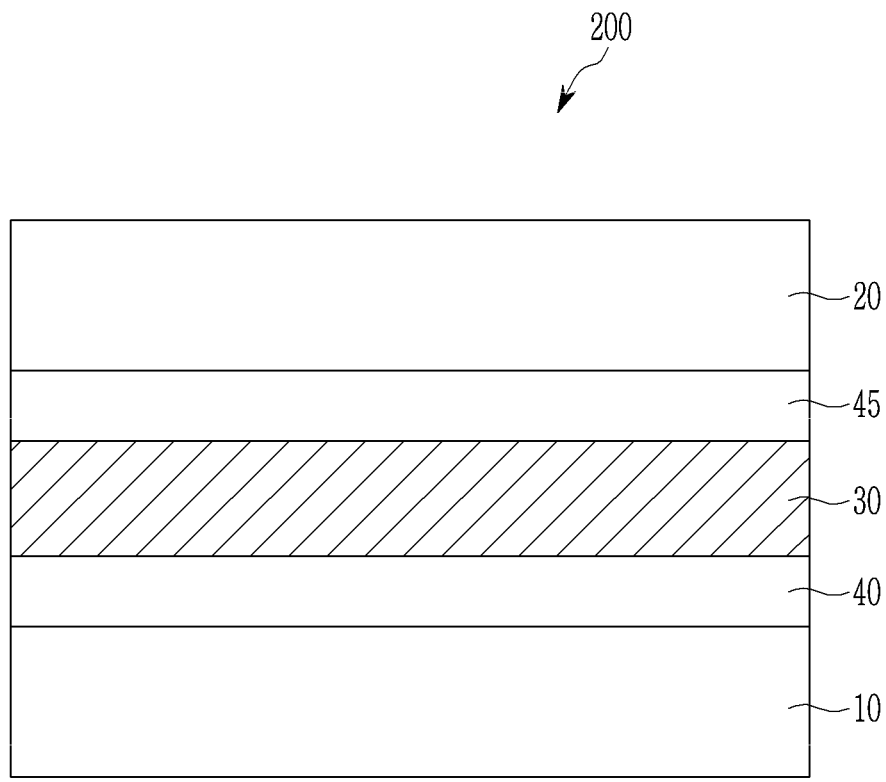
FIG. 2 is a cross-sectional view of an organic photoelectric device according to example embodiments.

FIG. 2 is a cross-sectional view showing an organic photoelectric device according to example embodiments.

Referring to FIG. 2, a photoelectric device 100 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
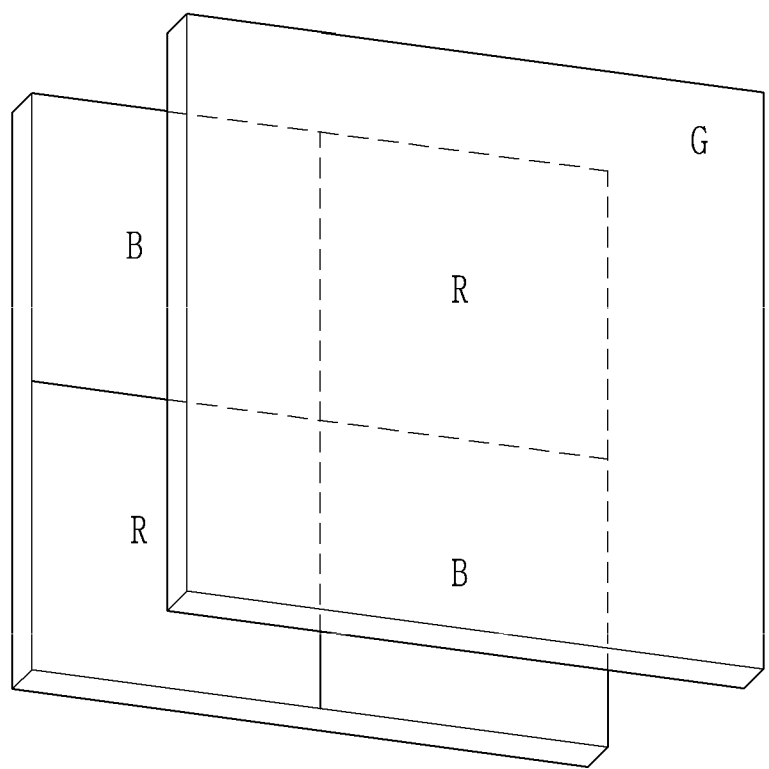
FIG. 3 is schematic top plan view showing an organic CMOS image sensor according to example embodiments.
Figure 4:
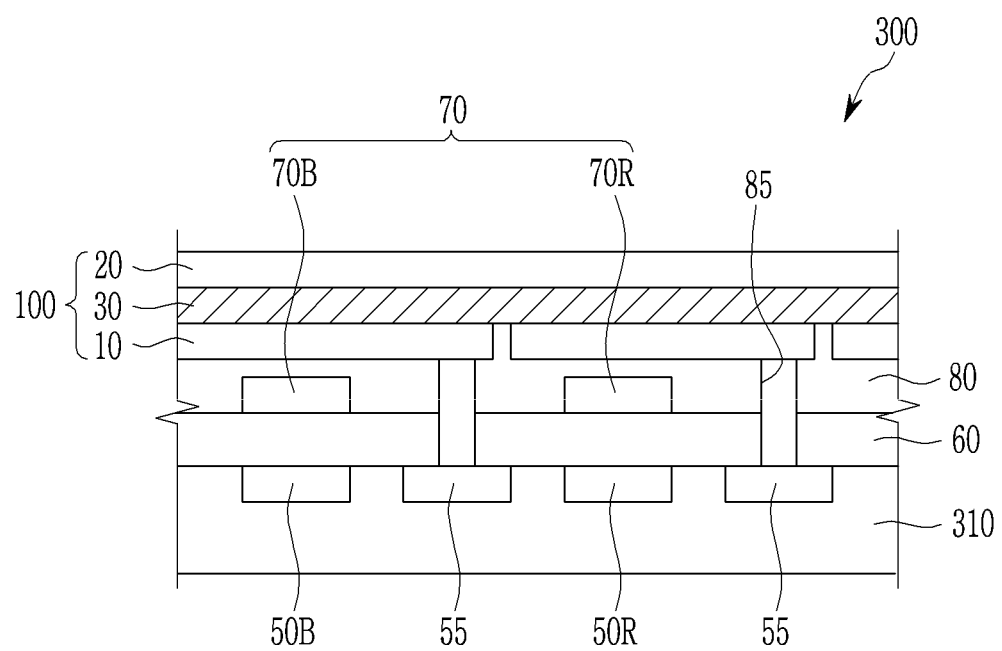
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and the organic photoelectric device 100.

The semiconductor substrate 310 may be a silicon substrate, and is integrated with the photo-sensing device 50R and 50B, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B overlapping with the photo-sensing device 50B and selectively transmitting blue light in a blue pixel and a red filter 70R overlapping with the photo-sensing device 50R and selectively transmitting red light in a red pixel. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 may eliminate a step caused by the color filter layer 70 and smoothen the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

As described above, the compound may be used as a p-type or n-type semiconductor compound, degradation of the compound in a deposition process and/or subsequent processes is inhibited, and thereby stable light absorption characteristics, electric characteristic and thermal properties may be realized. Thereby, green wavelength selectivity may be maintained, crosstalk caused by unnecessary absorption of other light except a green wavelength region may be decreased and sensitivity may be increased.

Figure 5:
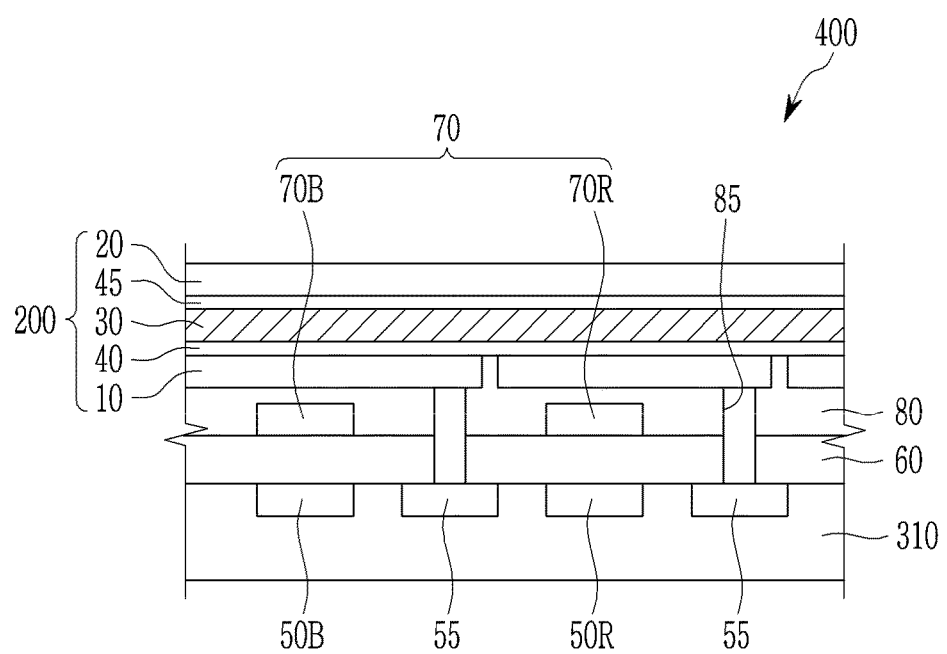
FIG. 5 is a schematic cross-sectional view showing an organic CMOS image sensor according to another example embodiment.

In FIG. 4, the organic photoelectric device 100 of FIG. 1 is included, but it is not limited thereto, and thus the organic photoelectric device 200 of FIG. 2 may be applied in the same manner. FIG. 5 is a cross-sectional view of an organic CMOS image sensor 400 including the organic photoelectric device 200 in FIG. 2.

Figure 6:
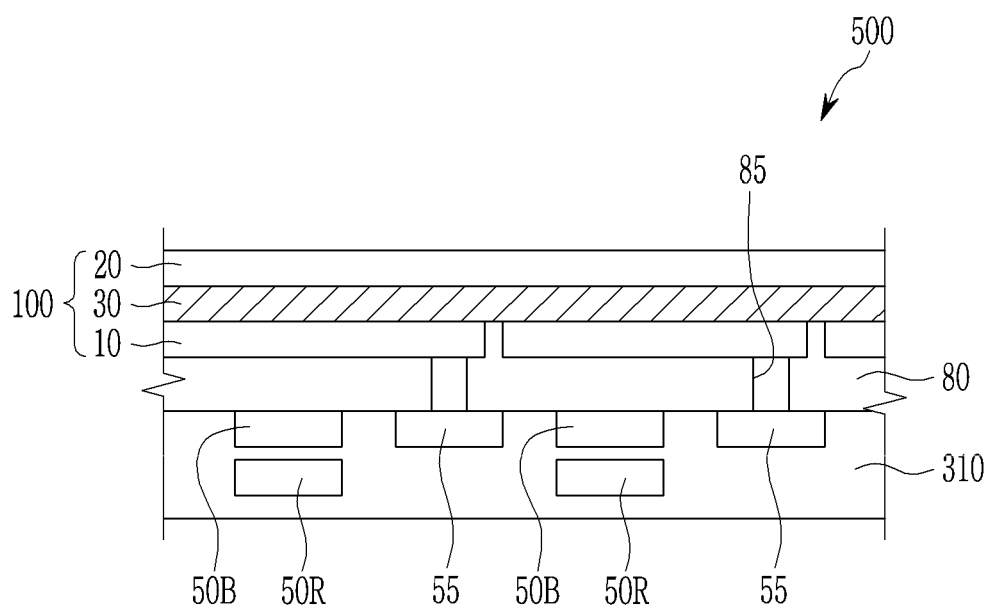
FIG. 6 is a schematic cross-sectional view showing an organic CMOS image sensor according to another example embodiments.

FIG. 6 is a cross-sectional view showing the organic CMOS image sensor according to another example embodiment.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption of light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
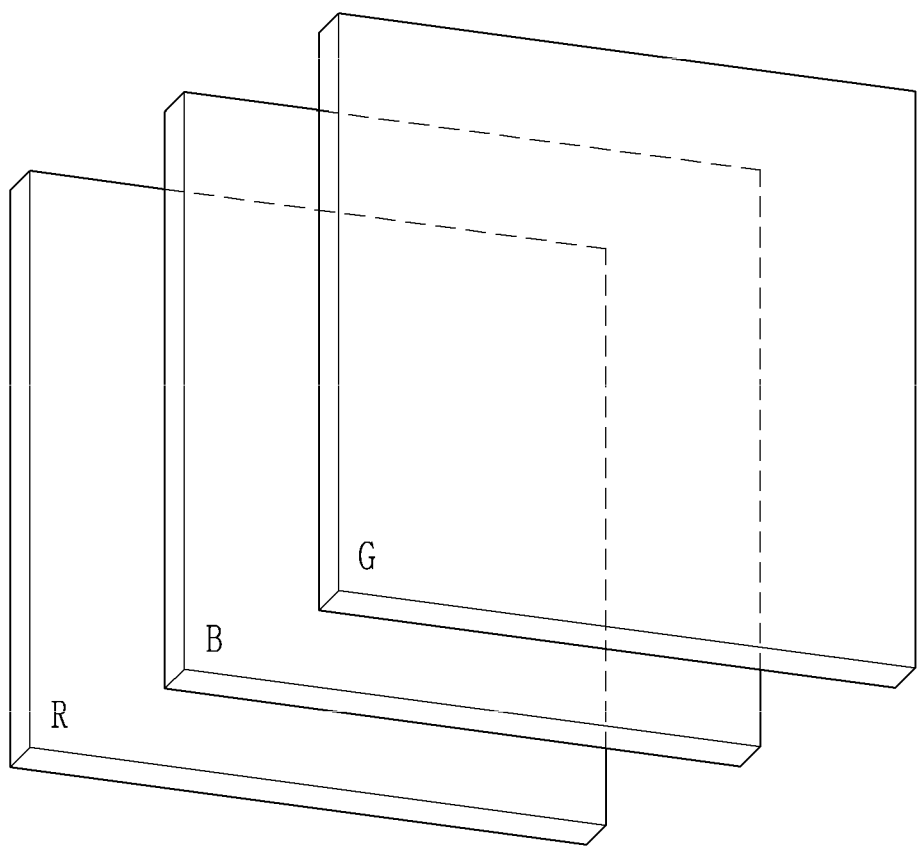
FIG. 7 is a schematic view showing an organic CMOS image sensor according to another example embodiments.

FIG. 7 is a schematic view showing an organic CMOS image sensor according to another example embodiment.

Referring to FIG. 7, the organic CMOS image sensor according to the present embodiment includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device (R), the green photoelectric device (G), and the blue photoelectric device (B) are sequentially stacked, but the stack order may be changed without limitation.

The green photoelectric device (G) may be the photoelectric device 100, the blue photoelectric device (B) may include electrodes facing each other and an active layer disposed therebetween and including an organic material selectively absorbing light in a blue wavelength region, and the red photoelectric device (R) may include electrodes facing each other and an active layer disposed therebetween and including an organic material selectively absorbing light in a red wavelength region.

As described above, the photoelectric device (G) selectively absorbing and/or sensing light in a green wavelength region, the photoelectric device (B) selectively absorbing and/or sensing light in a red wavelength region, and the photoelectric device (R) selectively absorbing and/or sensing light in a blue wavelength region are stacked, and thereby a size of an image sensor may be decreased, sensitivity may be increased, and crosstalk may be reduced.

The image sensor has absorbance in a desirable wavelength region and thus may improve sensitivity (YSNR10) and color reproducibility ($\Delta E^*ab$) while having a stack structure.

Herein, YSNR10 is a value indicating sensitivity of an image sensor and is measured in a method described in Juha Alakarhu's "Image Sensors and Image Quality in Mobile Phones" in an outline collection of 2007 International Image Sensor Workshop (Ogunquit Me., USA) wherein a minimum intensity of illumination at a ratio of a signal and a noise being about 10 is expressed as lux. Accordingly, as a value of YSNR10 is smaller, sensitivity becomes higher.

The color reproducibility ($\Delta E^*ab$) is a value indicating a certain difference from a standard color of an X-Rite chart, and $\Delta E^*ab$ is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2} \qquad \text{[Equation 1]}$$

In Equation 1, $\Delta L^*$ denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high color reproducibility at high sensitivity, it is necessary that ΔE*ab≤3 at YSNR10≤100 lux, and at least one of the compounds represented by Chemical Formulae 1 to 4 may realize sensitivity of YSNR10≤100 lux and color reproducibility of ΔE*ab≤3.

The image sensor may be applied to various electronic devices, for example, a mobile phone, a digital camera, and the like but is not limited thereto.

Hereinafter, the embodiments are illustrated in more detail with reference to examples. However, these examples are non-limiting examples, and inventive concepts are not limited thereto.

SYNTHESIS EXAMPLES

Synthesis Example 1

[Chemical Formula A-1]

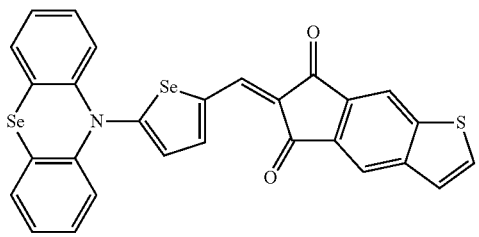

[Reaction Scheme A-1]

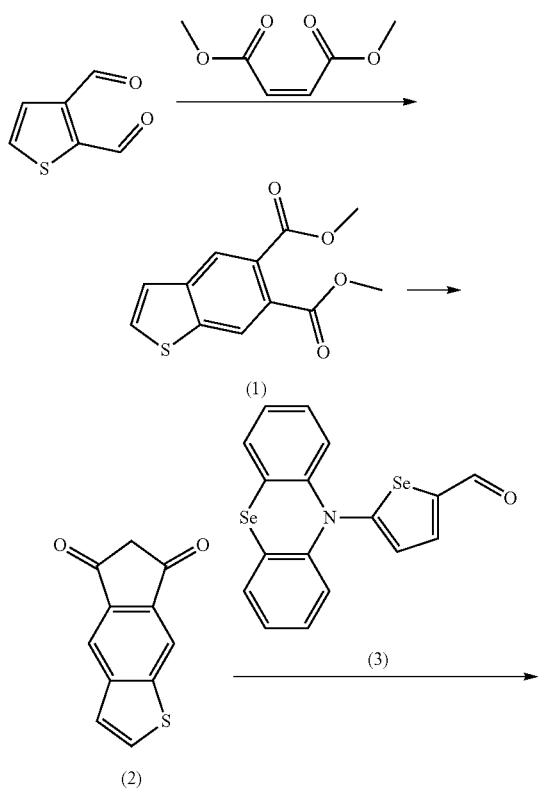

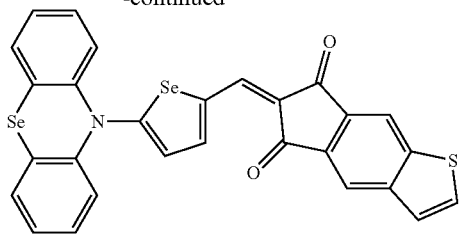

A-1

(1-i) Synthesis of Compound (1)

9.74 g (48.2 mmol) of tributylphosphine and 0.49 g (3.2 mmol) of 1,8-diazabicycloundec-7-ene are dissolved in 10 mL of dry methylene chloride (MC), and the solution is slowly injected at 0° C. into 40 mL of dry MC in which 4.5 g (32.1 mmol) of 2,3-thiophene dicarboxaldehyde and 4.86 g (33.7 mmol) of dimethyl maleate are dissolved. A product therefrom is separated and purified through silica gel column chromatography (an eluting solvent: MC) to obtain 5.2 g of dimethyl benzo[b]thiophene-5,6-dicarboxylate (a yield of 65%).

(1-ii) Synthesis of Compound (2)

1.66 g (41.6 mmol) of 60% NaH in mineral oil and 4.58 g (51.9 mmol) of ethyl acetate are sufficiently stirred in N-methyl-2-pyrrolidone, 3.0533 g (1.027 mmol) of Compound (1) is slowly added thereto, and the mixture is stirred at 75° C. for 6 hours. A precipitate therein is dissolved again in 50 mL of water, 10 mL of sulfuric acid is added, and the mixture is boiled for 10 minutes. Lastly, a precipitate therein is separated through a filter to obtain 0.23 g of 5H-indeno [5,6-b]thiophene-5,7(6H)-dione (a yield of 5%).

(1-iii) Synthesis of Compound (3)

2.2 ml of phosphoryl chloride is dripped into 6.8 ml of N,N-dimethyl formamide at −15° C. for 2 hours, and the mixture is stirred for 2 hours at room temperature (24° C.). The resultant is slowly added in a dropwise fashion to a mixture of 180 ml of dichloromethane and 6.84 g of 10-(selenophen-2-yl)-10H-phenoselenazine at −15° C., and the obtained mixture is stirred at room temperature for 30 minutes and concentrated under a reduced pressure. Subsequently, 100 ml of water is added thereto until pH becomes 14, a sodium hydroxide aqueous solution is added thereto, and the obtained mixture is stirred at room temperature (24° C.) for 2 hours. An organic layer extracted with ethyl acetate is washed with a sodium chloride aqueous solution and dried by adding anhydrous magnesium sulfate thereto. A product therefrom is separated and purified through silica gel column chromatography (hexane:dichloromethane=a volume ratio of 3:2) to obtain 5.16 g of 5-(10H-phenoselenazin-10-yl) selenophene-2-carbaldehyde (Compound (3)) (a yield=70%).

(1-iii) Synthesis of Compound Represented by Chemical Formula A-1

Figure 8:
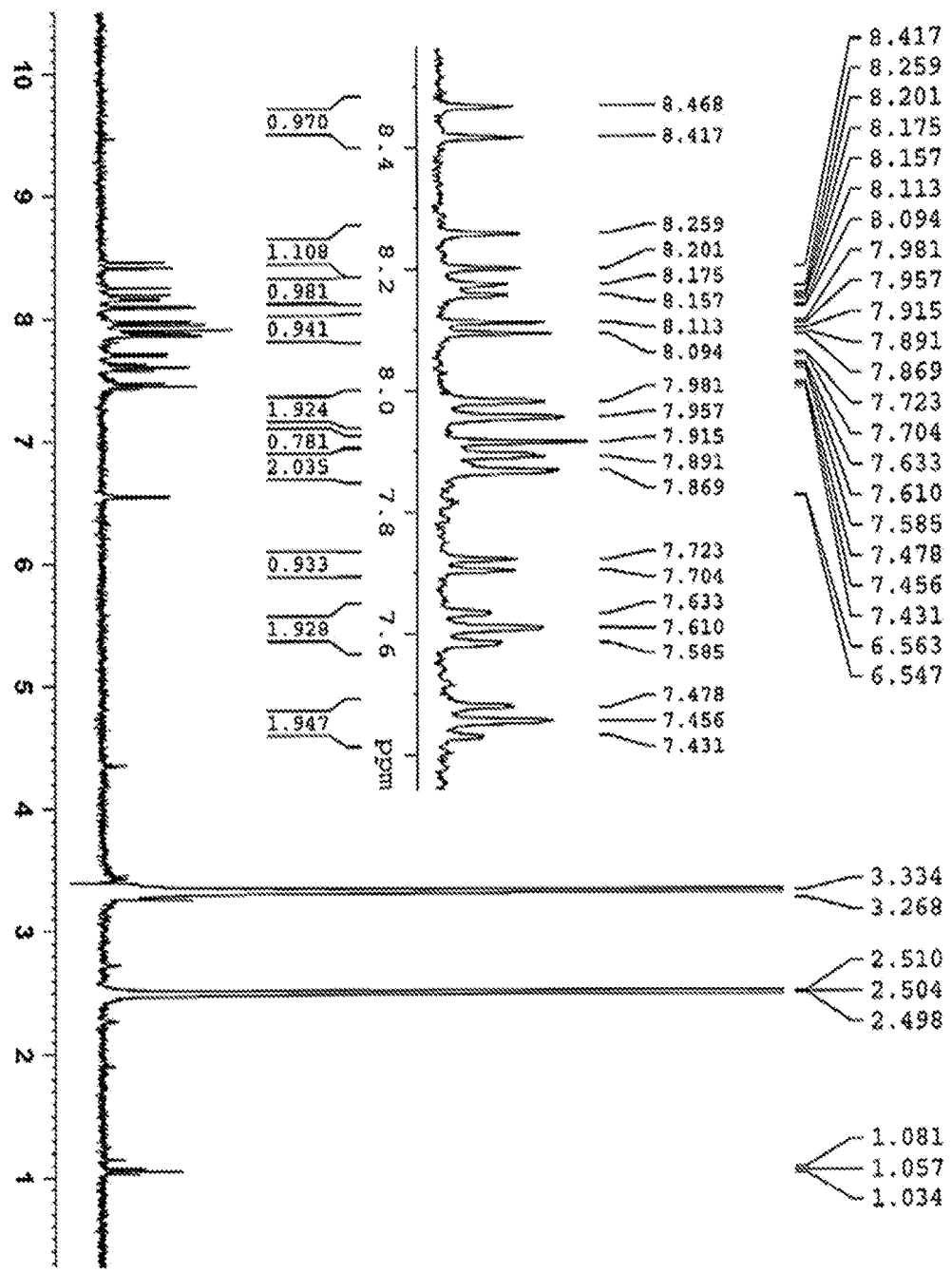
FIG. 8 shows $^1$H NMR data of the compound represented by Chemical Formula A-1 according to Synthesis Example 1.

0.31 g (0.77 mmol) of 5-(10H-phenoselenazin-10-yl)selenophene-2-carbaldehyde (Compound (3)) is suspended in ethanol, 0.19 g (0.94 mmol) of Compound (2) is added thereto, the obtained mixture is reacted at 50° C. for 2 hours to obtain 0.16 g of a compound represented by Chemical Formula A-1 (a yield of 90%). The obtained compound is sublimated and purified up to purity of 99.9%. $^{1}$H NMR data of the compound represented by Chemical Formula A-1 are shown in FIG. 8.

Synthesis Example 2

[Chemical Formula A-2]

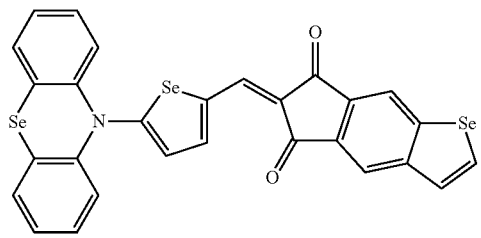

[Reaction Scheme A-2]

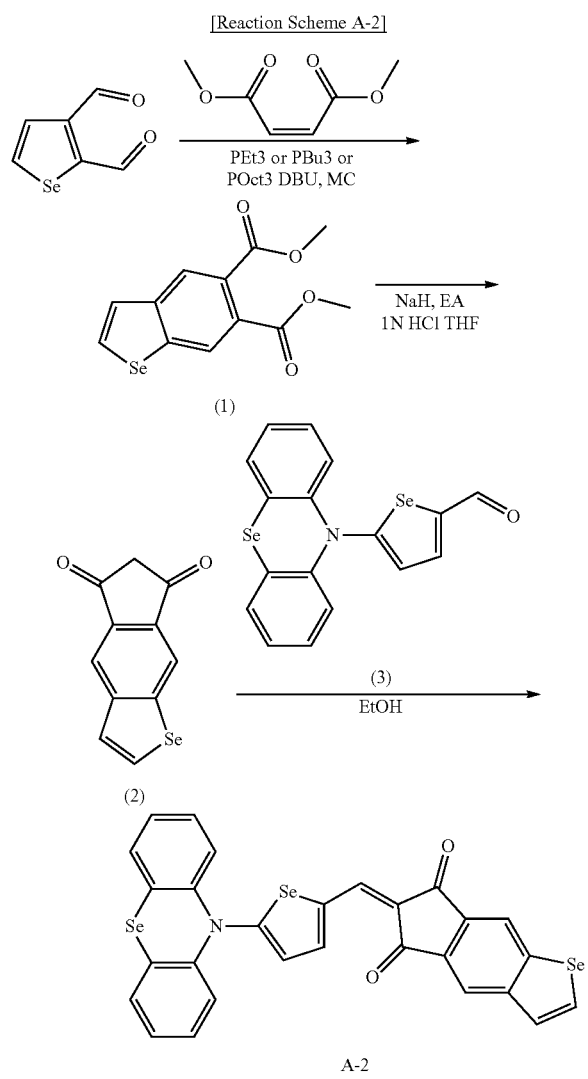

1. 2-Iodoselenophene 2-iodoselenophene is synthesized in a method described in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

2. 10H-phenoselenazine 10H-phenoselenazine is purchased from Medigen Inc. (purity of greater than or equal to 98%)
Reference: Preparation and Some Reactions of Phenoxazine and Phenoselenazine, Paulette Müller, N. P. Buu-Höl and R. RIPS, J. Org. Chem., 1959, 24 1, pp 37-39 t

3. Synthesis of 10-(selenophen-2-yl)-10H-phenoselenazine 13.6 g (52.8 mmol) of 2-iodoselenophene and 10.0 g (40.6 mmol) of 10H-phenoselenazine is refluxed in 100 ml of anhydrous toluene under presence of 5 mol % of Pd(dba)$_2$, 5 mol % of P(t-Bu)$_3$, and 4.29 g (44.7 mmol) of NaOtBu at 120° C. for 12 hours and cooled down to room temperature. Subsequently, a product obtained therefrom is separated and purified through silica gel column chromatography (toluene: hexane=a volume ratio of 1:4) to obtain 6.89 g of 10-(selenophen-2-yl)-10H-phenoselenazine (a yield of 45.2%).

4. Synthesis of 5-(10H-phenoselenazin-10-yl)selenophene-2-carbaldehyde 2.2 ml of phosphoryl chloride is added to 6.8 ml of N,N-dimethyl formamide in a dropwise fashion at −15° C. and stirred at room temperature (24° C.) for 2 hours. The resultant is slowly added in a dropwise fashion to a mixture of 180 ml of dichloromethane and 6.84 g of 10-(selenophen-2-yl)-10H-phenoselenazine at −15° C., and the obtained mixture is stirred at room temperature for 30 minutes and concentrated under a reduced pressure. 100 ml of water is added thereto, and a sodium hydroxide aqueous solution is added thereto until its pH becomes 14, and the obtained mixture is stirred at room temperature (24° C.) for 2 hours. An organic layer extracted with ethyl acetate is washed with a sodium chloride aqueous solution and dried by adding anhydrous magnesium sulfate thereto. A product obtained therefrom is separated and purified through silica gel column chromatography (hexane:dichloromethane=a volume ratio of 3:2) to obtain 5.16 g of 5-(10H-phenoselenazin-10-yl)selenophene-2-carbaldehyde (Compound (3)) (a yield of 70%).

5. Synthesis of Compound A-2

2.5 g (6.20 mmol) of 5-(10H-phenoselenazin-10-yl)selenophene-2-carbaldehyde and 2.00 g (8.06 mmol) of 5H-indeno[5,6-b]thiophene-5,7(6H)-dione are put in a 250 ml round flask, 80 ml of ethanol is added thereto, and the mixture is stirred at 60° C. for 4 hours. Subsequently, the resultant is cooled down to room temperature, 150 ml of n-hexane is added thereto, and the obtained mixture is stirred for 30 minutes. Next, a resultant therefrom is washed with n-hexane to obtain a crude product. Subsequently, the crude product is moved into a 2 L triangular flask, 450 ml of chloroform is added thereto, and the obtained mixture is heated at 70° C. stirred to dissolve the product. Then, 700 ml of n-hexane is slowly added thereto drop by drop, and the obtained mixture is cooled down to room temperature and filtered to obtain a product. The precipitation and purification are repeated up to purity of 99.9%. When the purification is complete, a product therefrom is vacuum-dried at 150° C. for 2 hours to remove residual hexane to obtain 3.02 g of (Z)-6-((5-(10H-phenoselenazin-10-yl)selenophen-2-yl)methylene)-5H-indeno[5,6-b]selenophene-5,7(6H)-dione (Compound A-2). Or, the product may be baked during the sublimation purification at 150° C. for greater than or equal to 2 hours. A yield is 83%.

Figure 9:
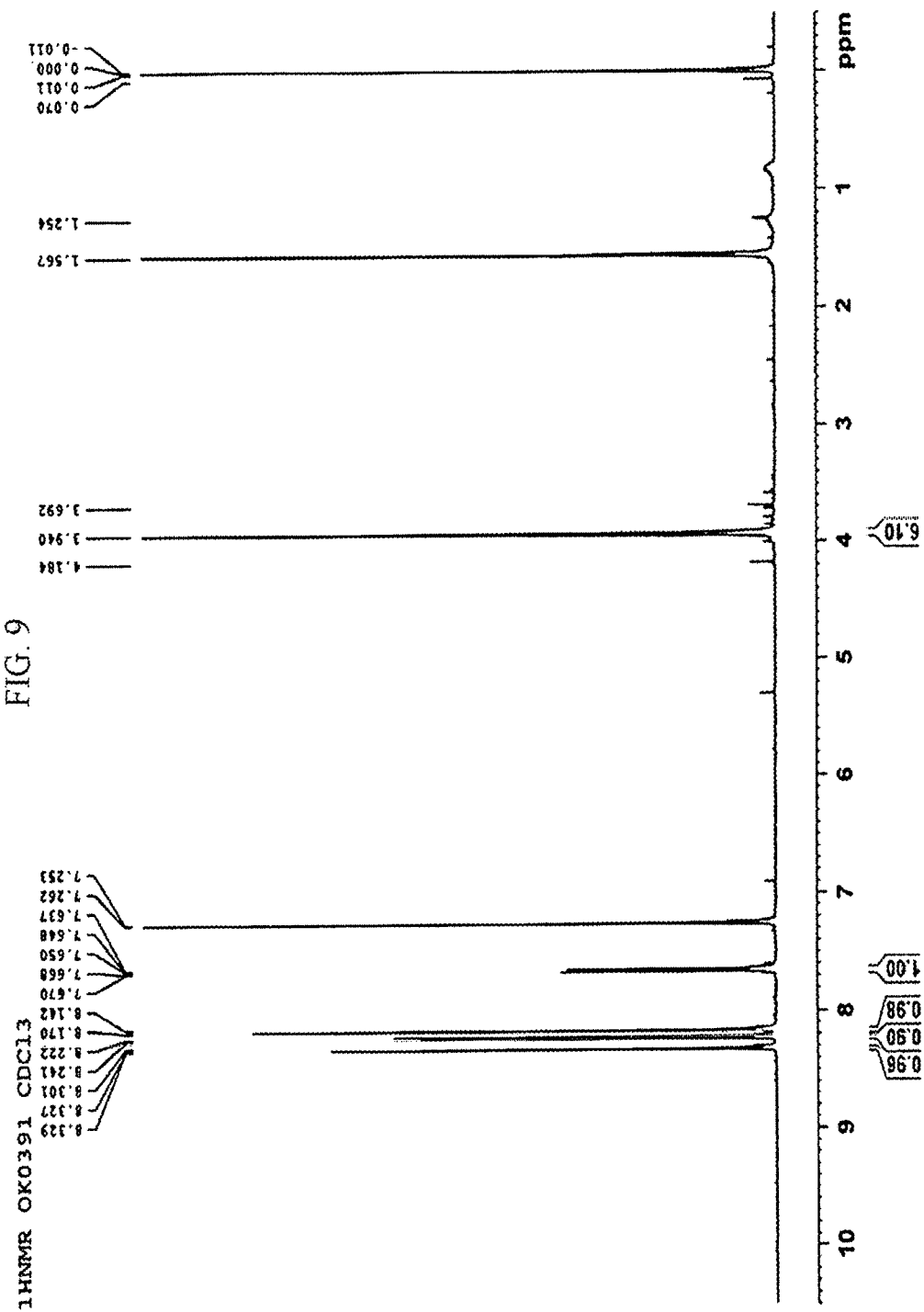
FIGS. 9 to 12 show NMR data of compounds obtained in Synthesis Examples.

¹H NMR data of the compound represented by Chemical Formula A-2 are shown in FIG. 9.

Synthesis Example 3

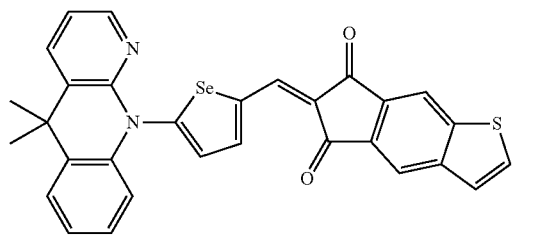

[Chemical Formula A-3]

1. 2-Iodoselenophene 2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

2. 5,5-dimethyl-5,10-dihydrobenzo[b][1,8]naphthyridine 5,5-dimethyl-5,10-dihydrobenzo[b][1,8]naphthyridine is purchased from Uniplus (greater than or equal to 98% of purity).

Reference: Preparation and Some Reactions of Phenoxazine and Phenoselenazine, Paulette Müller, N. P. Buu-Höi, and R. RIPS, J. Org. Chem., 1959, 24(1), pp 37-39 t

3. 5,5-dimethyl-10-(selenophen-2-yl)-5,10-dihydrobenzo[b][1,8]naphthyridine 5,5-dimethyl-10-(selenophen-2-yl)-5,10-dihydrobenzo[b][1,8]naphthyridine is obtained by using 2-iodineselenophene and 5,5-dimethyl-5,10-dihydrobenzo[b][1,8]naphthyridine.

4. 5-(5,5-dimethylbenzo[b][1,8]naphthyridin-10(5H)-yl)selenophene-2-carbaldehyde 2.2 ml of phosphoryl chloride is added to 6.8 ml of N,N-dimethyl formamide in a dropwise fashion at −15° C., and the mixture is stirred at room temperature (24° C.) for 2 hours. The obtained resultant is slowly added in a dropwise fashion to a mixture of 180 ml of dichloromethane and 6.84 g of 10-(selenophen-2-yl)-10H-phenoselenazine at −15° C., and the obtained mixture is stirred at room temperature for 30 minutes and concentrated under a reduced pressure. 100 ml of water is added thereto, a sodium hydroxide an aqueous solution is added thereto until pH becomes 14, and the obtained mixture is stirred at room temperature (24° C.) for 2 hours. An organic layer extracted with ethyl acetate is washed with a sodium chloride aqueous solution and dried by adding anhydrous magnesium sulfate thereto. A product obtained therefrom is separated and purified through silica gel column chromatography (hexane:dichloromethane=a volume ratio of 3:2) to obtain 5.16 g of 5-(5,5-dimethylbenzo[b][1,8]naphthyridin-10(5H)-yl)selenophene-2-carbaldehyde (a yield of 70%).

5. Synthesis of (Z)-6-((5-(5,5-dimethylbenzo[b][1,8]naphthyridin-10(5H)-yl)selenophen-2-yl)methylene)-5H-indeno[5,6-b]thiophene-5,7(6H)-dione 2.5 g (6.20 mmol) of 5-(10H-phenoselenazin-10-yl)selenophene-2-carbaldehyde and 1.60 g (8.06 mmol) of 5H-indeno[5,6-b]thiophene-5,7(6H)-dione are put in a 250 ml round flask, 80 ml of ethanol is added thereto, and the mixture is stirred at 60° C. for 4 hours. Subsequently, a resultant therefrom is cooled down to room temperature, 150 ml of n-hexane is added thereto, and the mixture is stirred for 30 minutes. Subsequently, the obtained resultant is filtered with n-hexane to obtain a crude product. The crude product is moved into a 2 L triangular flask and then, dissolved in 450 ml of chloroform while heated and stirred at 70° C. Subsequently, the solution is cooled down to room temperature, while 700 ml of n-hexane is slowly added thereto drop by drop. The obtained resultant is washed to obtain a product. The precipitation and purification are repeated up to purity of 99.9%. When the purification is complete, a product therefrom is vacuum-dried at 150° C. for 2 hours to remove residual hexane and obtain 3.02 g of Compound A-3. Or the product may be baked at 150° C. for greater than or equal to 2 hours during the sublimation and purification. A yield is 83%.

Figure 10:
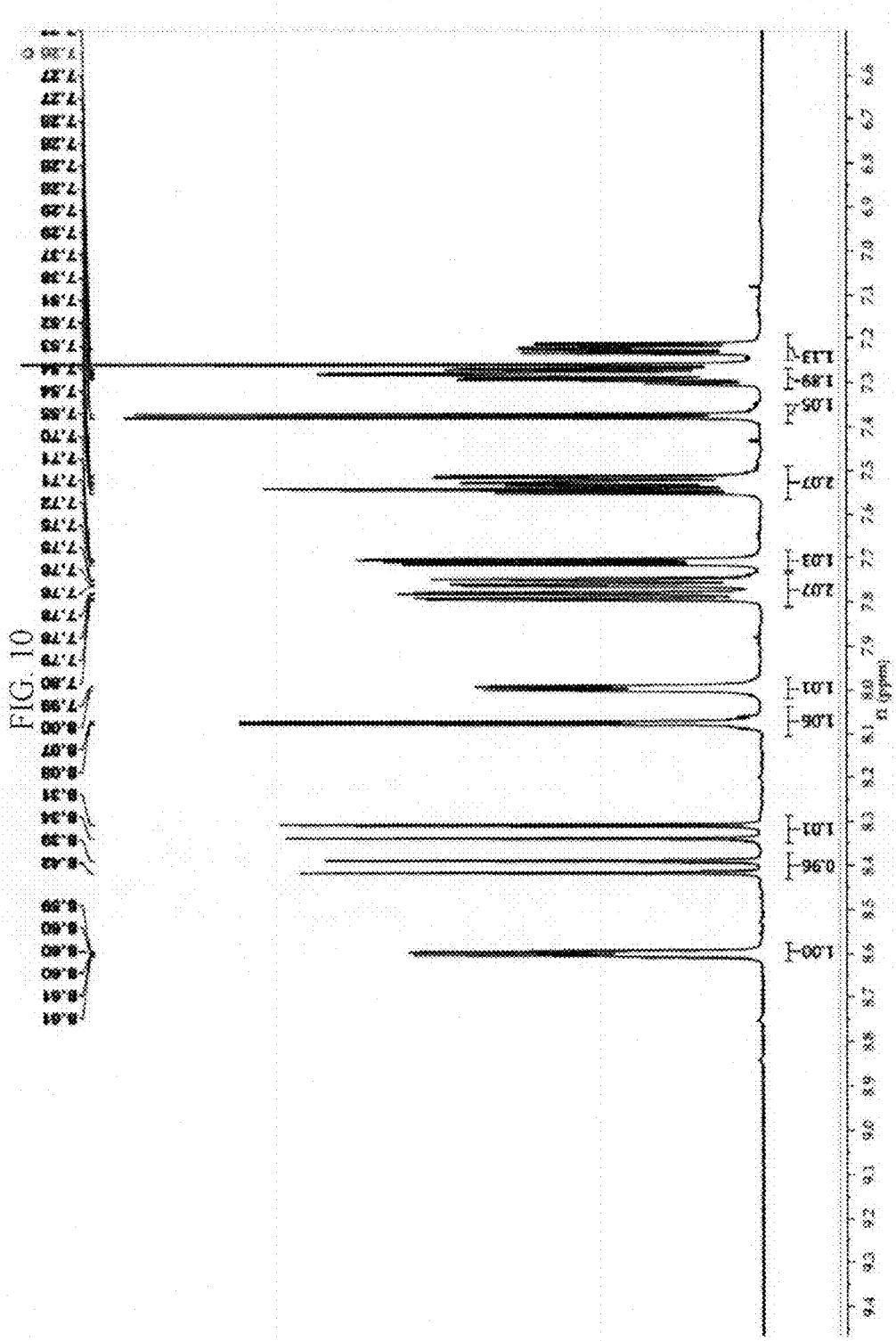

¹H NMR data of a compound represented by Chemical Formula A-3 are shown in FIG. 10.

Synthesis Example 4

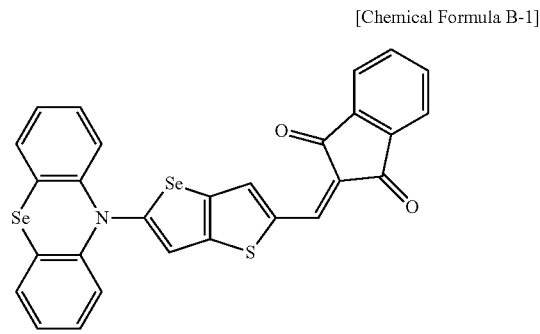 [SMILES: O=C1C(=Cc2cc3[se]c(N4c5ccccc5[Se]c5ccccc54)cc3s2)C(=O)c2ccccc21]

[Chemical Formula B-1]

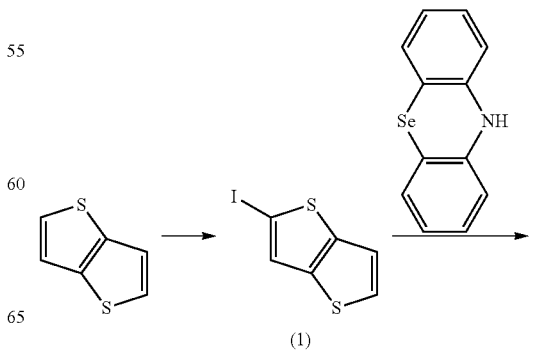

[Reaction Scheme B-1]

(1)

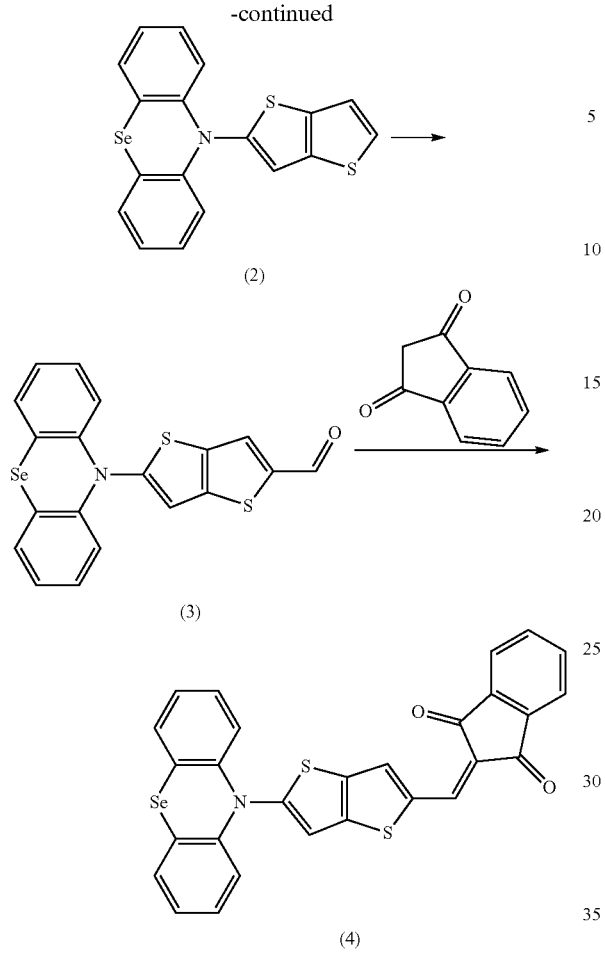

(1-i) Synthesis of Compound (1)

2-iodothieno[3,2-b]thiophene (Compound (1)) is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(1-ii) Synthesis of Compound (2)

13.6 g (52.8 mmol) of Compound (1) and 10.0 g (40.6 mmol) of 10H-phenoselenazine are heated and refluxed in 100 ml of anhydrous toluene under presence of 5 mol % of Pd(dba)$_2$, 5 mol % of P(tBu)$_3$, and 4.29 g (44.7 mmol) of NaOtBu for 2 hours. A product therefrom is separated and purified through silica gel column chromatography (toluene:hexane=a volume ratio of 1:4) to obtain 6.89 g of Compound (2) (a yield of 45.2%).

(1-iii) Synthesis of Compound (3)

2.2 ml of phosphoryl chloride is added to 6.8 ml of N,N-dimethyl formamide in a dropwise fashion at −15° C., and the mixture is stirred at room temperature (24° C.) for 2 hours. The obtained resultant is slowly added in a dropwise fashion to a mixture of 180 ml of dichloromethane and 6.84 g of Compound (2) at −15° C., and the obtained mixture is stirred at room temperature for 30 minutes and concentrated under a reduced pressure. 100 ml of water is added thereto, a sodium hydroxide aqueous solution is added thereto until pH becomes 14, and the obtained mixture is stirred at room temperature (24° C.) for 2 hours. An organic layer is extracted with ethyl acetate, washed with a sodium chloride aqueous solution, and dried by anhydrous magnesium sulfate thereto. A product obtained therefrom is separated and purified through silica gel column chromatography (hexane:dichloromethane=a volume ratio of 3:2) to obtain 5.16 g of Compound (3) (a yield=70.4%).

(1-iv) Synthesis of Compound Represented by Chemical Formula B-1

2.00 g (4.96 mmol) of Compound (3) is suspended in ethanol, 1.46 g (7.44 mmol) of 1H-cyclopenta[b]naphthalene-1,3(2H)-dione is added thereto, the obtained mixture is reacted at 50° C. for 2 hours to obtain 2.62 g of Compound 4 represented by Chemical Formula B-1 (a yield=90%). The obtained compound is purified through sublimation up to purity of 99.9%.

Figure 11:
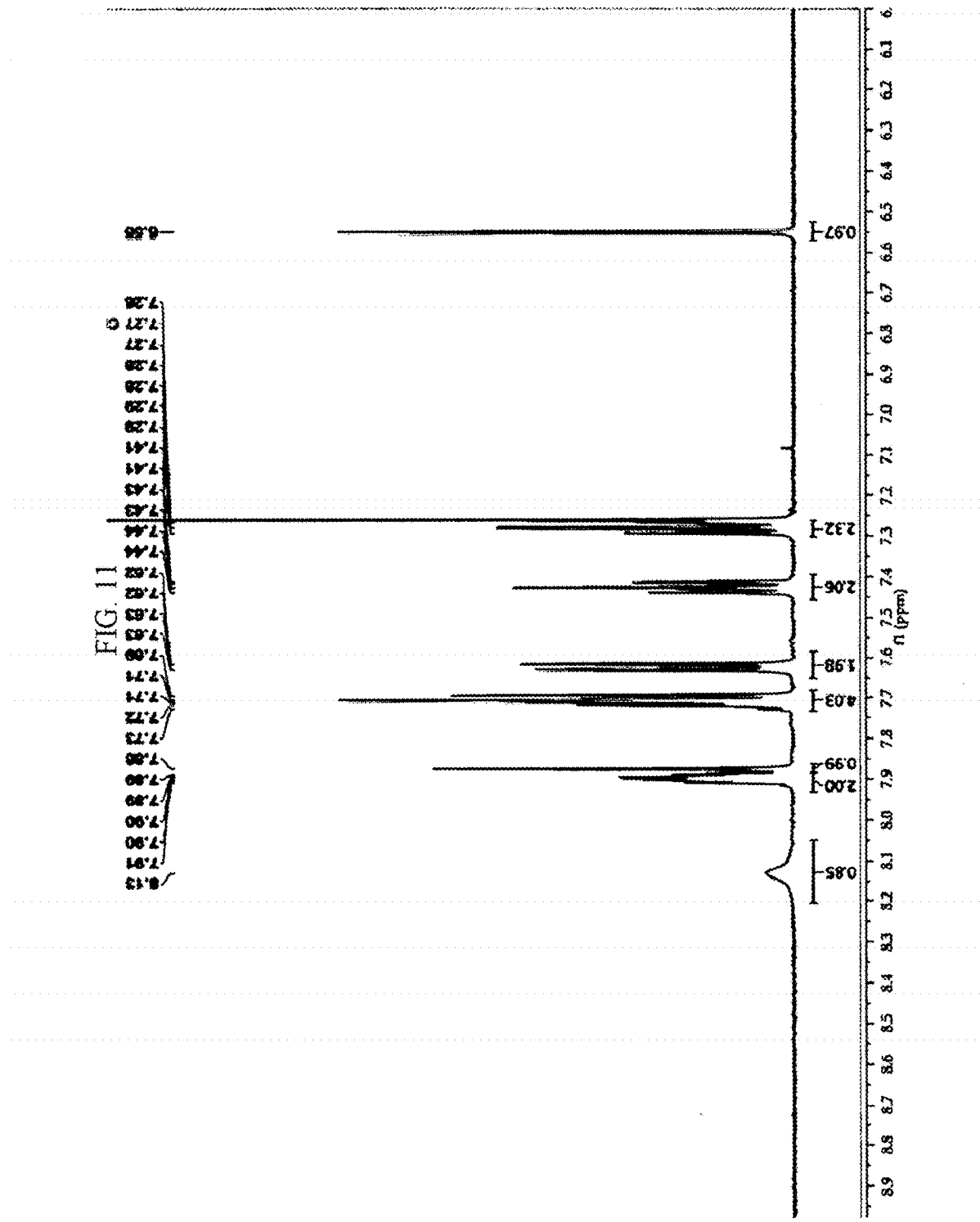

$^1$H NMR data of the compound represented by Chemical Formula B-1 are shown in FIG. 11.

Synthesis Example 5

[Chemical Formula C-1]

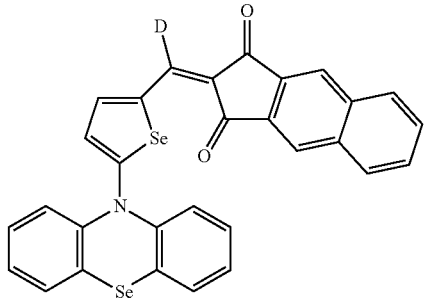

[Reaction Scheme C-1]

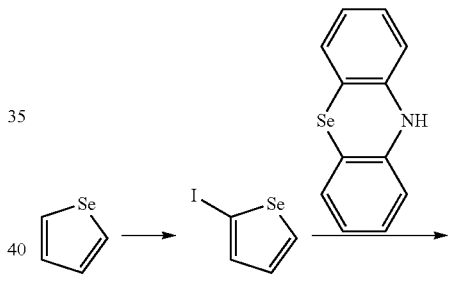

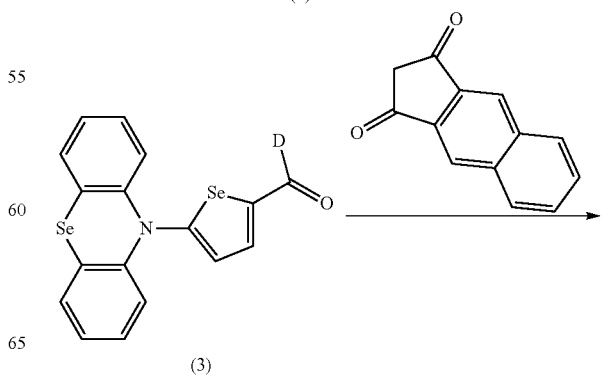

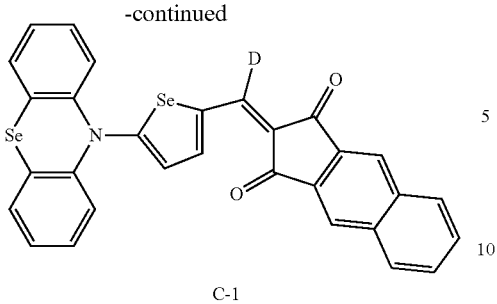

C-1

(1-i) Synthesis of Compound (1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(1-ii) Synthesis of Compound (2)

13.6 g (52.8 mmol) of 2-iodoselenophene and 10.0 g (40.6 mmol) of 10H-phenoselenazine are heated and refluxed in 100 ml of anhydrous toluene under presence of 5 mol % of Pd(dba)$_2$, 5 mol % of P(tBu)3, and 4.29 g (44.7 mmol) of NaOtBu for 2 hours. A product therefrom is separated and purified through silica gel column chromatography (toluene:hexane=a volume ratio of 1:4) to obtain 6.89 g of 10-(selenophen-2-yl)-10H-phenoselenazine (a yield of 45.2%).

(1-iii) Synthesis of Compound (3)

2.2 ml of phosphoryl chloride is added in a dropwise fashion to 6.8 ml of N,N-dimethyl formamide-d7(N,N-dimethylformamide-d7) at −15° C., and the mixture is stirred at room temperature (24° C.) for 2 hours. The obtained resultant is added in a dropwise fashion to a mixture of 180 ml of dichloromethane and 6.84 g of Compound (2) at −15° C., and the obtained mixture is slowly stirred at room temperature for 30 minutes and concentrated under a reduced pressure. 100 ml of water is added thereto, a sodium hydroxide aqueous solution is added thereto until pH becomes 14, and the obtained mixture is stirred at room temperature (24° C.) for 2 hours. An organic layer is extracted with ethyl acetate, is washed with a sodium chloride aqueous solution, and dried by adding anhydrous magnesium sulfate thereto. A product therefrom is separated and purified through silica gel column chromatography (hexane:dichloromethane=a volume ratio of 3:2) to obtain 5.16 g of Compound (3) (a yield of 66%).

(1-iv) Synthesis of Compound C-1

2.00 g (4.96 mmol) of Compound (3) is suspended in ethanol, 1.46 g (7.44 mmol) of 1H-cyclopenta[b]naphthalene-1,3(2H)-dione is added thereto, and the obtained mixture is reacted at 50° C. for 2 hours to obtain 2.62 g of a compound represented by Chemical Formula C-1 (a yield=66%). The obtained compound is purified through sublimation up to purity of 99.9%.

Figure 12:
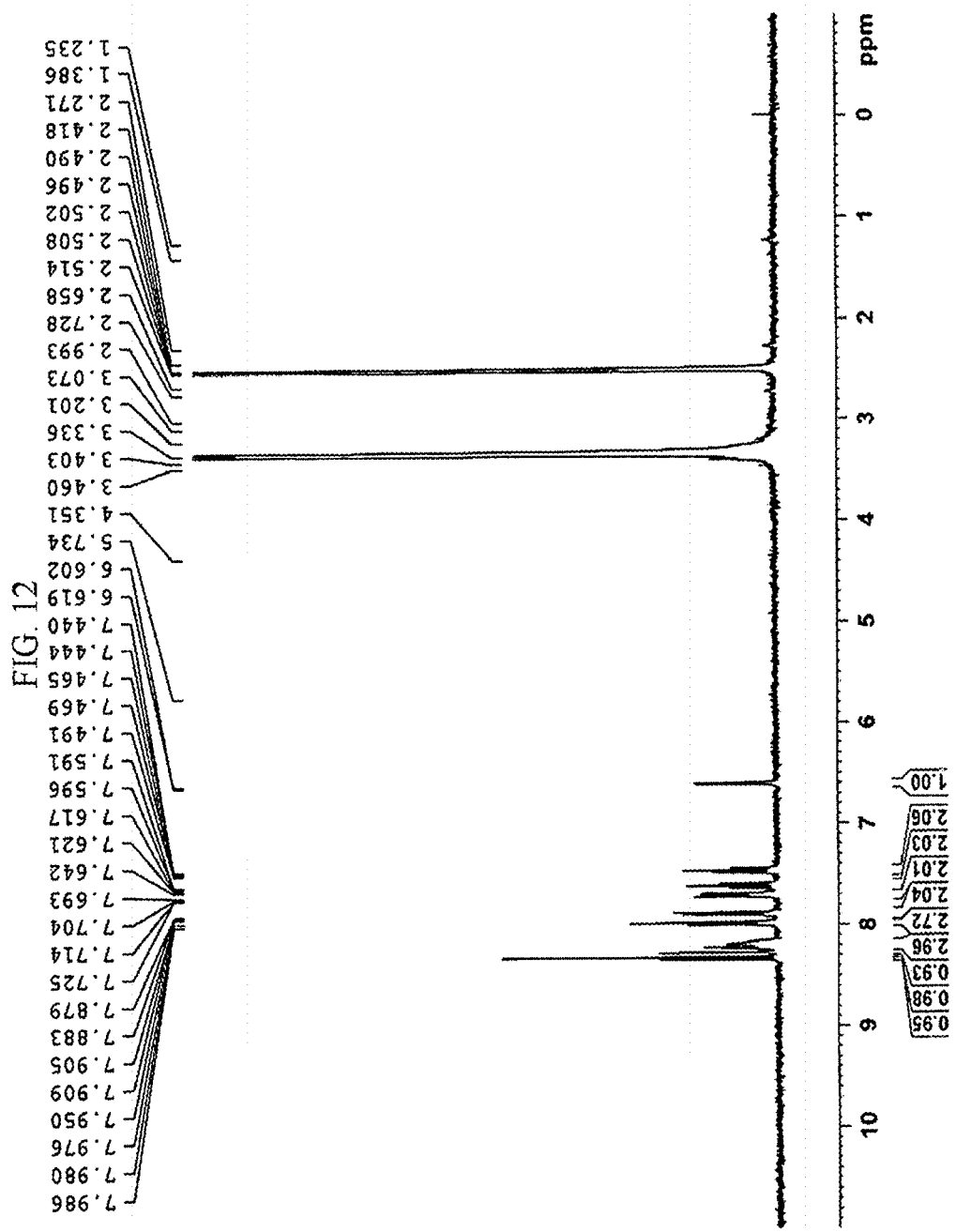

$^1$H NMR data of the compound represented by Chemical Formula C-1 are shown in FIG. 12.

$^1$H NMR ppm (DMSO) 8.33-8.27 (m)-3H, 8.24-8.16 (m)-3H, 7.98 (m)-2H, 7.88 (m)-2H, 7.71 (m)2H, 7.61 (t)-2H, 7.45 (t)-2H, 6.61 (d)-1H Synthesis Example 6

[Chemical Formula C-2]

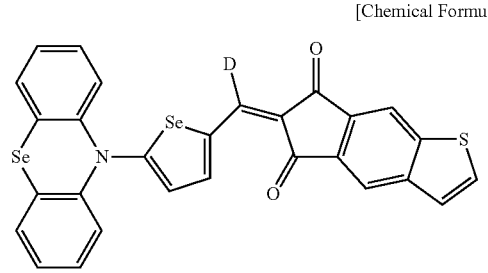

A compound is synthesized according to the same method as Synthesis Example 1 except for using N,N-dimethylformamide-d7 instead of N,N-dimethyl formamide.

Synthesis Example 7

[Chemical Formula D-1]

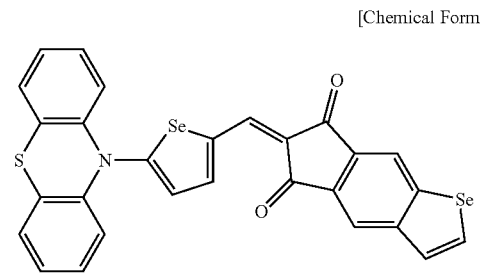

[Reaction Scheme D-1]

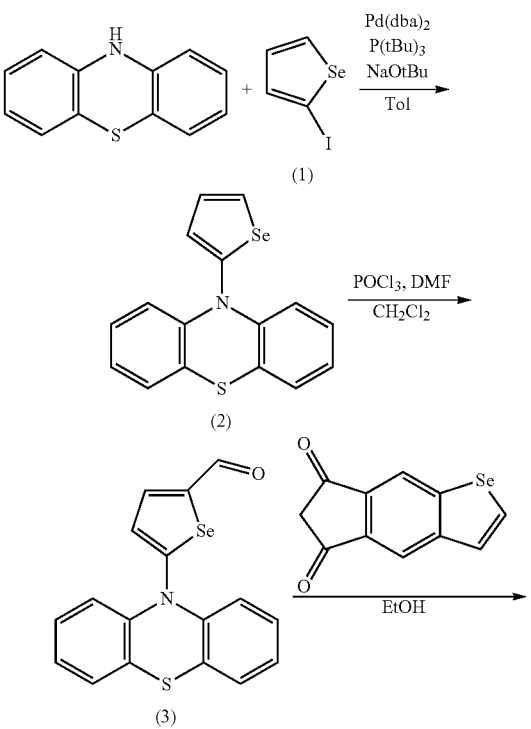

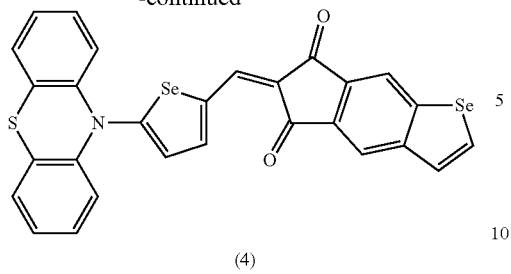

(4)

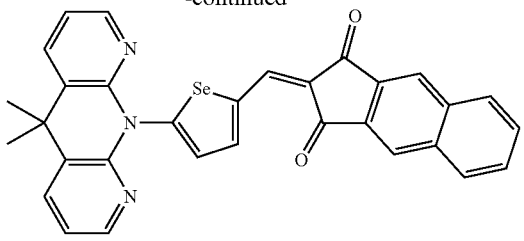

(4)

A compound represented by Chemical Formula D-1 is synthesized according to the same method as Synthesis Example 2 except for using 10H-phenothiazine instead of 10H-phenoselenazine.

Synthesis Example 8

A compound represented by Chemical Formula D-2 is synthesized according to the same method as Synthesis Example 5 except for using 5,5-dimethyl-5,10-dihydro-pyrido[2,3-b][1,8]naphthyridine instead of 2-iodoselenophene and using N,N-dimethyl formamide instead of N,N-dimethyl formamide-d7.

Synthesis Example 9

[Chemical Formula D-2]

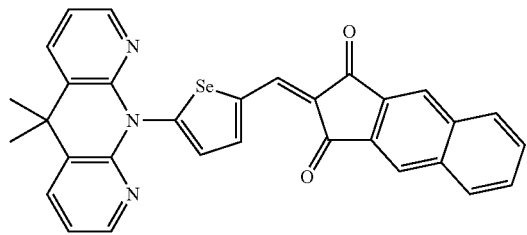

[Chemical Formula D-3]

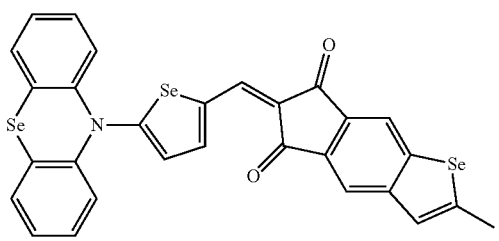

[Reaction Scheme D-2]

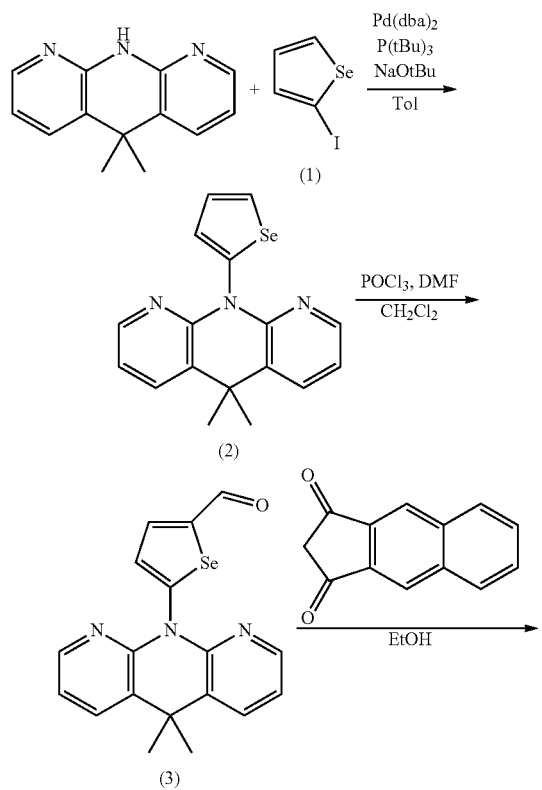

[Reaction Scheme D-3]

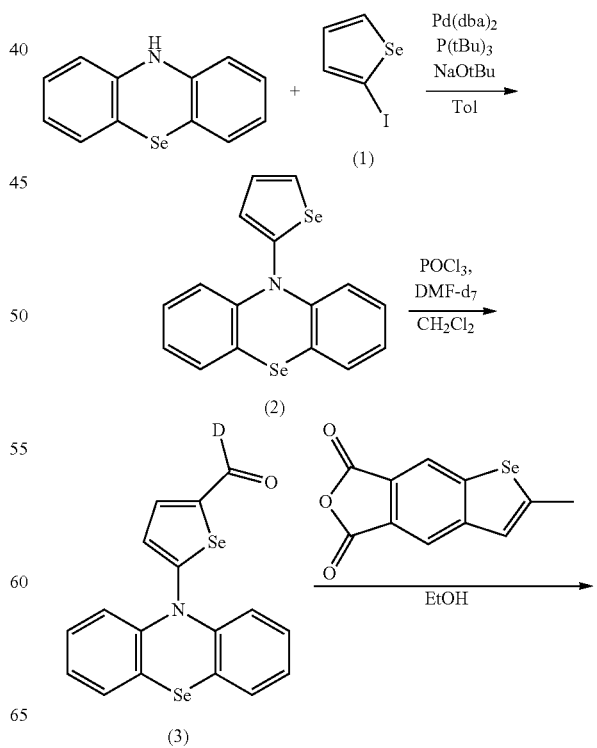

99
-continued
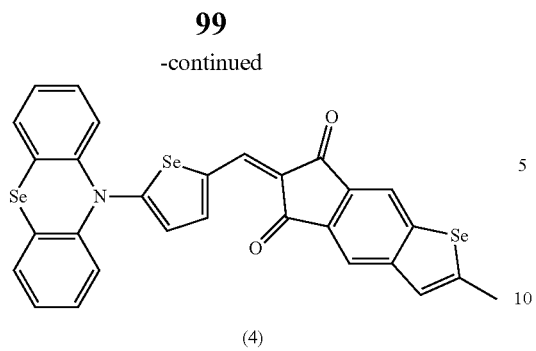
(4)
Synthesis Example 10
[Chemical Formula D-4]
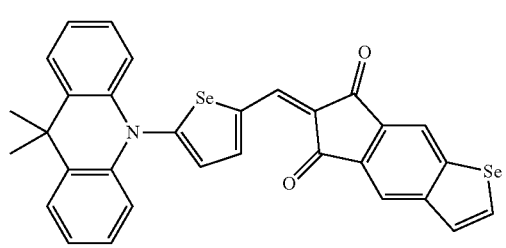
[Reaction Scheme D-4]
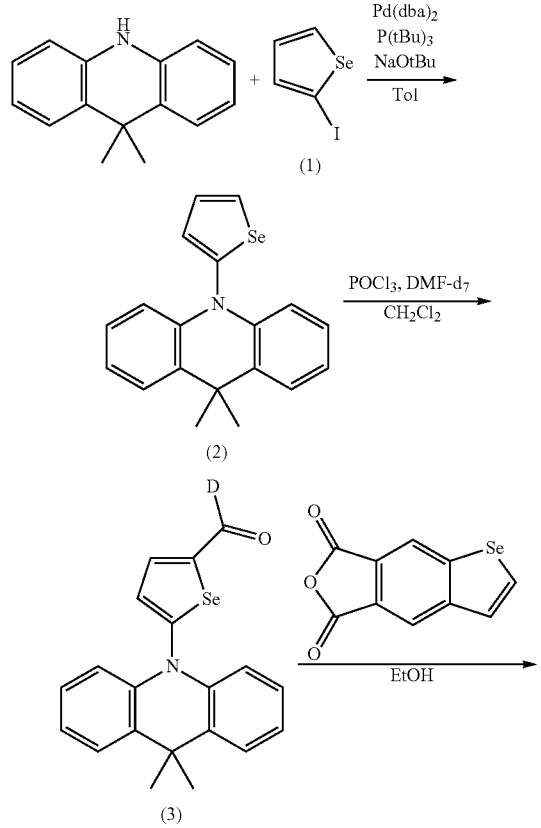
100
-continued
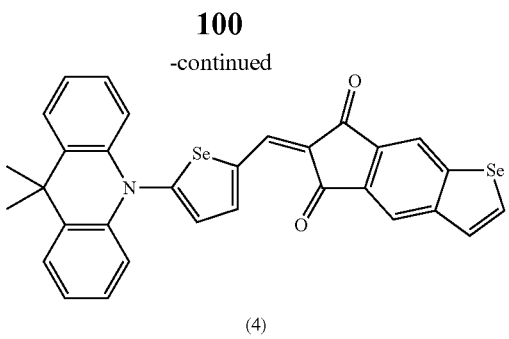
(4)
Synthesis Example 11
[Chemical Formula D-5]
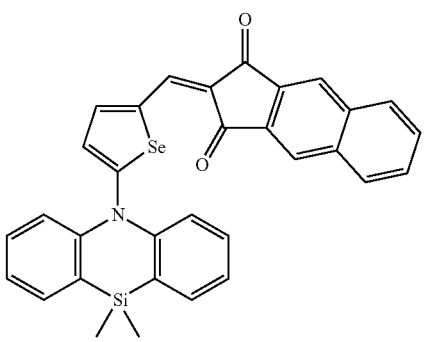
[Reaction Scheme D-5]
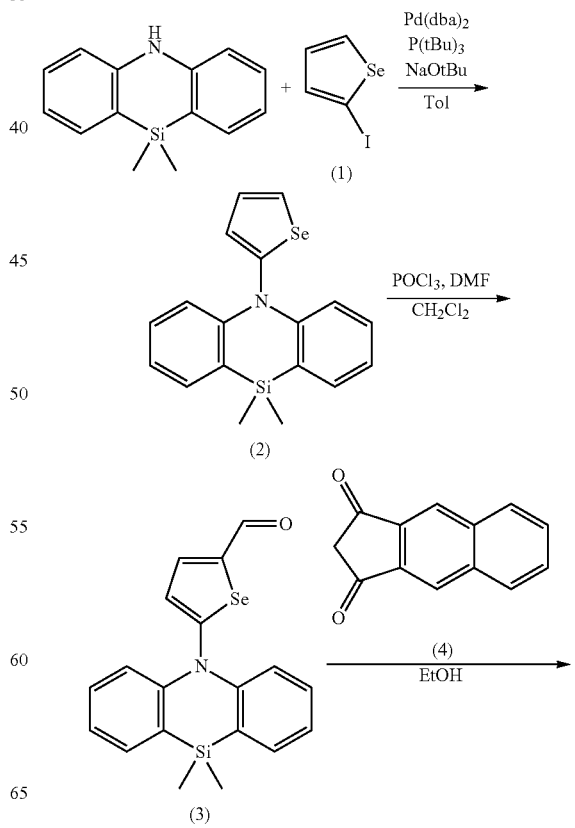

-continued

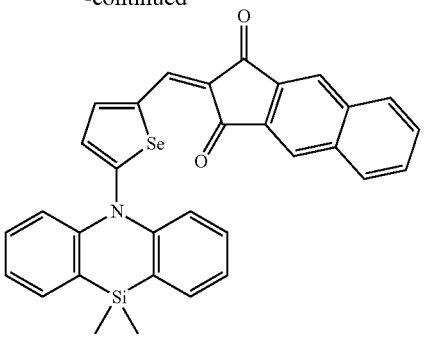

(1-i) Synthesis of 10,10-dimethyl-5,10-dihydrodibenzo[b,e][1,4]azasiline 10,10-dimethyl-5,10-dihydrodibenzo[b,e][1,4]azasiline is synthesized in a method described in Y. Kitamoto, T. Namikawa, T. Suzuki, Y. Miyata, H. Kita, T. Sato, S. Oi. Tetrahedron Letters 57 (2016) 4914-4917.

(1-ii) Synthesis of Compound (1)

42.6 g (167.89 mmol) of $I_2$ is added in anhydrous diethyl ether at a $N_2$ atmosphere. Then, 20.0 g (152.62 mmol) of selenophene is put in 1 L 3-neck round bottom flask equipped with 250 ml dropping funnel and thermometer at a $N_2$ atmosphere and dissolved in 400 ml of anhydrous diethyl ether. Then, n-butyllithium (2.5M in diethylether) is put in the dropping funnel and slowly added thereto. The addition rate is controlled to maintain temperature of lower than or equal to 30° C. Then, the inside wall of the dropping funnel is washed using anhydrous diethyl ether and then the mixture is stirred at 50° C. for 30 minutes. Then, $I_2$ dissolved in anhydrous diethyl ether is moved into the dropping funnel and is slowly added at −78° C. and stirred at a room temperature for 12 hours. Then, the mixture is extracted with 400 ml of distilled water and a water layer is extracted with 200 ml of ethyl ether twice. Then, an organic layer is washed with $NaHSO_3$ aqueous solution and remaining $I_2$ is quenched. Then, water in the organic layer is dried using magnesium sulfate and diethyl ether is removed in rotary evaporator to obtain 37.3 g of Compound (1) (a yield=95%).

(1-iii) Synthesis of Compound (2)

90 ml of anhydrous toluene is added in 250 ml 3-neck round bottom flask equipped with a reflux condenser at a $N_2$ atmosphere. Then, toluene is degassed by substituting with vacuum and $N_2$ atmosphere three times. Then, 1.17 g (2.03 mmol) of $Pd(dba)_2$ and 2.0 ml (2.03 mmol) of $t-Bu_3P$ (1.0M in toluene) are added thereto and the mixture is stirred. Then, 9.15 g (40.6 mmol) of 10,10-dimethyl-5,10-dihydrodibenzo[b,e][1,4]azasiline, 13.6 g (52.8 mmol) of 2-Iodoselenophene and 4.29 g (44.7 mmol) of NaOtBu are added thereto and the mixture are refluxed at 100° C. for 5 hours. Then, the obtained mixture is cooled down to room temperature, filtered in Celite, and toluene is removed in rotary evaporator. A product therefrom is separated and purified through silica gel column chromatography (hexane:dichloromethane=a volume ratio of 1:9) to obtain 10.0 g of Compound (2) (a yield of 76%).

NMR 1H NMR (300 MHz, CD2Cl2): δ (ppm) 8.12 (dd, J=6.0, 1.2 Hz, 1H), 7.55 (dd, J=1.5, 7.2 Hz, 2H), 7.33 (dd, J=6.0, 3.6 Hz, 1H), 7.2-7.3 (m, 2H), 7.12 (dd, J=1.2, 3.6 Hz, 1H), 7.01 (dt, J=0.9, 7.2 Hz, 2H), 6.93 (d, J=9.7 Hz, 2H), 0.48 (s, 6H)

(1-iv) Synthesis of Compound (3)

2 ml of N,N-dimethylformamide (DMF) is put in 25 ml of round flask at a $N_2$ atmosphere. Then, 0.66 ml (7.10 mmol) of phosphorous oxychloride ($POCl_3$) is slowly added thereto by a syringe in −10° C. ice bath (including NaCl) and the mixture is stirred at a room temperature for 1 hour to obtain a reagent. The solution color is changed from transparent to yellow and then red. Then, 1.93 g (5.46 mmol) of 10,10-dimethyl-5-(selenophen-2-yl)-5,10-dihydrodibenzo[b,e][1,4]azasiline is dissolved in 180 ml of dichloromethane (yellow). The obtained reagent is slowly added thereto in an ice bath and the color of the mixture is changed into reddish brown. Then, the mixture is stirred at a room temperature for 1 hour and 200 ml of distilled water and NaOH aqueous solution are added thereto until pH becomes 14. After stirring the mixture for 1 hour, the mixture is extracted with dichloromethane and an organic layer is washed with NaCl saturated aqueous solution. Then, water in the organic layer is dried using magnesium sulfate and diethyl ether is removed in rotary evaporator. Then, a product therefrom is separated and purified through silica gel column chromatography (hexane:dichloromethane=a volume ratio of 3:2) to obtain 1.56 g of Compound (3) (a yield of 75%).

NMR 1H NMR (300 MHz, CD2Cl2): δ (ppm) 9.45 (s, 1H), 7.69 (d, J=7.8 Hz, 2H), 7.62-7.75 (m, 3H), 7.46 (td, J=7.8, 1.8 Hz, 2H), 7.33 (td, J=7.2, 1.2 Hz, 2H), 6.34 (d, J=4.8 Hz, 1H), 0.41 (s, 6H)

(1-v) Synthesis of Final Compound 1.146 g (2.99 mmol) of a compound (3) and 0.600 g (3.05 mmol) of a compound (4) are put in a three-necked round-bottomed flask and then purged with $N_2$ gas. Then, 80 ml of ethanol is added to the reactant and the mixture is refluxed at 75 to 80° C. for 12 hours. The resultant is cooled down to room temperature of 25° C., and water is added thereto. When a powder is formed therein, the powder is filtered. Then, chloroform and EtOH are used to perform recrystallization, obtaining 1.20 g of the compound represented by Chemical Formula D-5 (with a yield of 71%).

Synthesis Example 12

[Chemical Formula D-6]

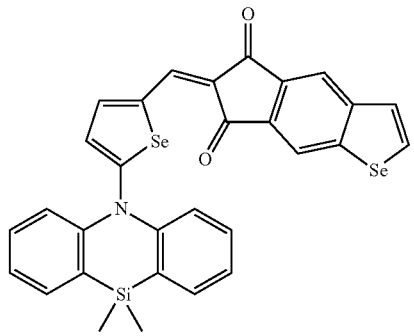

[Reaction Scheme D-6]

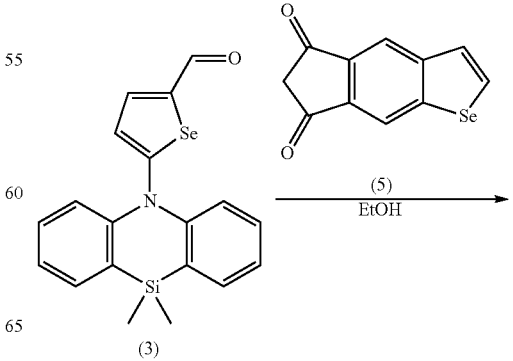

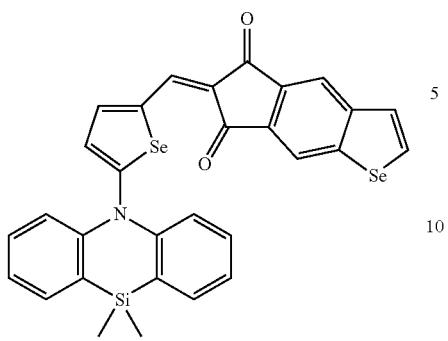

1.89 g (4.94 mmol) of a compound (3) and 1.300 g (5.21 mmol) of a compound (5) are put in a three-necked round-bottomed flask and then purged with $N_2$ gas. Then, 80 ml of ethanol is added to the reactant and the mixture is refluxed at 75 to 80° C. for 12 hours. The resultant is cooled down to room temperature of 25° C. and water is added thereto. When a powder is formed therein, the powder is filtered. Then, chloroform and EtOH are used to perform recrystallization, obtaining 2.2 g of the compound represented by Chemical Formula D-6 (with a yield of 72%).

Synthesis Example 13

[Chemical Formula D-7]

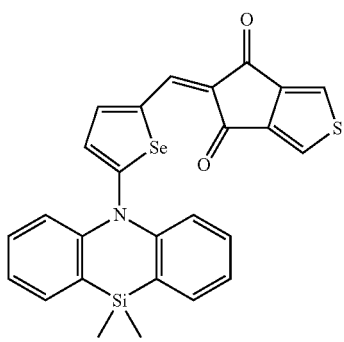

[Reaction Scheme D-7]

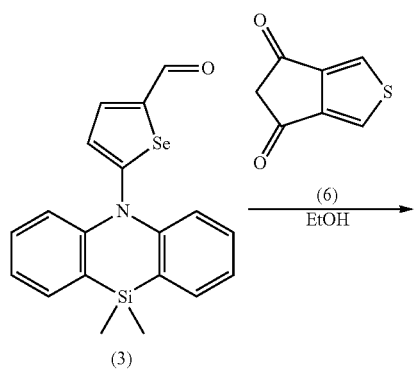

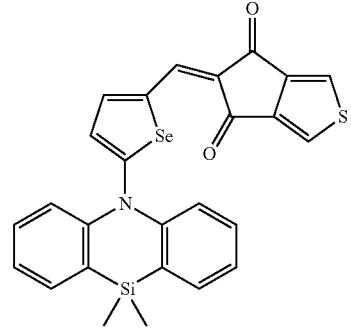

1.58 g (4.94 mmol) of a compound (3) and 0.700 g (4.60 mmol) of a compound (6) are put in a three-necked round-bottomed flask and then purged with $N_2$ gas. Then, 80 ml of ethanol is added to the reactant and the mixture is refluxed at 75 to 80° C. for 12 hours. The resultant is cooled down to room temperature of 25° C. and water is added thereto. When a powder is formed therein, the powder is filtered. Then, chloroform and EtOH are used to perform recrystallization, obtaining 1.65 g of the compound represented by Chemical Formula D-7 (with a yield of 77%).

Evaluation I

Thermal stability of the compounds according to Synthesis Examples 1 to 13 is evaluated.

The thermal stability is evaluated from a 10 wt % loss temperature (Ts, deposition temperature) at 10 Pa, and when a compound has a higher melting point (Tm) than the deposition temperature (Ts), a satisfactory thin film may be formed from the compound without decomposition during deposition.

The loss temperature is measured using a thermogravimetric analysis (TGA) method.

The results are shown in Table 1.

TABLE 1

|  | Tm (° C.) | Ts (° C.) | ΔT (° C.) (Tm − Ts) |
| --- | --- | --- | --- |
| Synthesis Example 1 | 372 | 284 | 88 |
| Synthesis Example 2 | 370 | 288 | 82 |
| Synthesis Example 3 | 258 | 254 | 4 |
| Synthesis Example 4 | 251 | 248 | 3 |
| Synthesis Example 5 | 349 | 276 | 73 |
| Synthesis Example 6 | 365 | 287 | 78 |
| Synthesis Example 7 | 366 | 282 | 84 |
| Synthesis Example 8 | 265 | 263 | 2 |
| Synthesis Example 9 | 334 | 282 | 52 |
| Synthesis Example 10 | 306 | 252 | 54 |
| Synthesis Example 11 | 323 | 257 | 66 |
| Synthesis Example 12 | 325 | 265 | 60 |
| Synthesis Example 13 | 334 | 237 | 97 |

* Tm (° C.): a melting point of Compound, a decomposition temperature of a compound
* Ts (° C.): a deposition temperature, a temperature where a compound is sublimated and loses 10% of a weight at 10 Pa Referring to Table 1, the compounds according to Synthesis Examples 1 to 13 have a high melting point and may be formed into a satisfactory thin film without decomposition during deposition.

Formation of Thin Film

Preparation Example 1

A thin film is formed by codepositing the compound of Synthesis Example 1 and C60 in a thickness ratio of 1:1.

Preparation Example 2

A thin film is formed by codepositing the compound of Synthesis Example 2 and C60 in a thickness ratio of 1:1.

Preparation Example 3

A thin film is formed by codepositing the compound of Synthesis Example 3 and C60 in a thickness ratio of 1:1.

Preparation Example 4

A thin film is formed by codepositing the compound of Synthesis Example 4 and C60 in a thickness ratio of 1:1.

Preparation Example 5

A thin film is formed by codepositing the compound of Synthesis Example 5 and C60 in a thickness ratio of 1:1.

Preparation Example 6

A thin film is formed by codepositing the compound of Synthesis Example 6 and C60 in a thickness ratio of 1:1.

Preparation Example 7

A thin film is formed by codepositing the compound of Synthesis Example 7 and C60 in a thickness ratio of 1:1.

Preparation Example 8

A thin film is formed by codepositing the compound of Synthesis Example 8 and C60 in a thickness ratio of 1:1.

Preparation Example 9

A thin film is formed by codepositing the compound of Synthesis Example 9 and C60 in a thickness ratio of 1:1.

Preparation Example 10

A thin film is formed by codepositing the compound of Synthesis Example 10 and C60 in a thickness ratio of 1:1.

Preparation Example 11

A thin film is formed by codepositing the compound of Synthesis Example 11 and C60 in a thickness ratio of 1:1.

Preparation Example 12

A thin film is formed by codepositing the compound of Synthesis Example 12 and C60 in a thickness ratio of 1:1.

Preparation Example 13

A thin film is formed by codepositing the compound of Synthesis Example 13 and C60 in a thickness ratio of 1:1.

Evaluation II

Light absorption characteristics of the thin films according to Preparation Examples 1 to 13 are evaluated.

The light absorption characteristics are evaluated by using an ultraviolet (UV)-visible ray (UV-Vis) with Cary 5000 UV Spectroscopy (Varian Medical Systems).

The results are shown in Table 2.

TABLE 2

|  | Abs. coeff. ($10^4$/cm) | $\lambda_{max}$ (nm) | FWHM (nm) |
| --- | --- | --- | --- |
| Synthesis Example 1 | 7.5 | 536 | 88 |
| Synthesis Example 2 | 8.8 | 534 | 87 |
| Synthesis Example 3 | 7.0 | 544 | 83 |
| Synthesis Example 4 | 4.6 | 548 | 124 |
| Synthesis Example 5 | 7.5 | 551 | 88 |
| Synthesis Example 6 | 7.5 | 551 | 88 |
| Synthesis Example 7 | 8.7 | 537 | 86 |
| Synthesis Example 8 | 6.7 | 556 | 88 |
| Synthesis Example 9 | 9.5 | 537 | 81 |
| Synthesis Example 10 | 6.2 | 549 | 81 |
| Synthesis Example 11 | 7.7 | 557 | 83 |
| Synthesis Example 12 | 7.8 | 543 | 76 |
| Synthesis Example 13 | 6.8 | 540 | 80 |

Referring to Table 2, the thin films of Preparation Examples 1 to 13 have high light absorption characteristics and satisfactory wavelength selectivity in a green wavelength region.

Manufacture of Photoelectric Device

Example 1

An about 150 nm-thick anode is formed by sputtering ITO on a glass substrate, and an active layer is formed by codepositing the compound of Synthesis Example 1 (a p-type semiconductor) and C60 (an n-type semiconductor) in a thickness ratio of 1:1. On the active layer, a 10 nm-thick charge auxiliary layer is formed by depositing molybdenum oxide (MoOx, 0<x≤3), and a 7 nm-thick cathode is formed thereon by sputtering ITO, manufacturing a photoelectric device.

Example 2

A photoelectric device is manufactured according to the same method as Example 1 except for using the compound of Synthesis Example 2 instead of the compound of Synthesis Example 1.

Example 3

A photoelectric device is manufactured according to the same method as Example 1 except for using the compound of Synthesis Example 3 instead of the compound of Synthesis Example 1.

Example 4

A photoelectric device is manufactured according to the same method as Example 1 except for using the compound of Synthesis Example 4 instead of the compound of Synthesis Example 1.

Example 5

A photoelectric device is manufactured according to the same method as Example 1 except for using the compound of Synthesis Example 5 instead of the compound of Synthesis Example 1.

Example 6

A photoelectric device is manufactured according to the same method as Example 1 except for using the compound of Synthesis Example 6 instead of the compound of Synthesis Example 1.

Example 7

A photoelectric device is manufactured according to the same method as Example 1 except for using the compound of Synthesis Example 7 instead of the compound of Synthesis Example 1.

Example 8

A photoelectric device is manufactured according to the same method as Example 1 except for using the compound of Synthesis Example 8 instead of the compound of Synthesis Example 1.

Example 9

A photoelectric device is manufactured according to the same method as Example 1 except for using the compound of Synthesis Example 9 instead of the compound of Synthesis Example 1.

Example 10

A photoelectric device is manufactured according to the same method as Example 1 except for using the compound of Synthesis Example 10 instead of the compound of Synthesis Example 1.

Example 11

A photoelectric device is manufactured according to the same method as Example 1 except for using the compound of Synthesis Example 11 instead of the compound of Synthesis Example 1.

Example 12

A photoelectric device is manufactured according to the same method as Example 1 except for using the compound of Synthesis Example 12 instead of the compound of Synthesis Example 1.

Example 13

A photoelectric device is manufactured according to the same method as Example 1 except for using the compound of Synthesis Example 13 instead of the compound of Synthesis Example 1.

Evaluation III

Light absorption characteristics and electric characteristics of the photoelectric devices according to Examples 1 to 13 are evaluated.

The light absorption characteristics are evaluated by using an ultraviolet (UV)-visible ray (UV-Vis) with Cary 5000 UV Spectroscopy (Varian Medical Systems).

External quantum efficiency is measured by using an IPCE measurement system (McScience Inc., Korea). First, the IPCE measurement system is calibrated by using a Si photodiode (Hamamatsu Photonics K.K., Japan) and then, respectively equipped on the photoelectric devices of Examples 1 to 6, and their external quantum efficiency at a wavelength ranging from about 350 to about 750 nm is measured. The external quantum efficiency after allowing the photoelectric devices to stand at 170° C. for 3 hours is measured in a wavelength region ranging from about 350 to about 750 nm.

The results are shown in Table 3.

TABLE 3

|  | Thickness (nm) | $\lambda_{max}$ (nm) | EQE (%) (@3 V) (170° C., 3 h) |
|---|---|---|---|
| Example 1 | 110 | 545 | 65 |
| Example 2 | 100 | 540 | 65 |
| Example 3 | 110 | 550 | 64 |
| Example 5 | 110 | 550 | 67 |
| Example 6 | 110 | 545 | 65 |
| Example 7 | 100 | 545 | 60 |
| Example 9 | 100 | 540 | 62 |
| Example 10 | 100 | 550 | 60 |
| Example 11 | 100 | 545 | 47 |
| Example 12 | 100 | 540 | 49 |
| Example 13 | 100 | 540 | 45 |

Referring to Table 3, the photoelectric devices according to Examples show high wavelength selectivity in a green wavelength region and maintain satisfactory external quantum efficiency after allowed to stand at a high temperature.

While some example embodiments have been particularly shown and described, it will be understood by one of ordinary skill in the art that variations in form and detail may be made therein without departing from the spirit and scope of the claims.

What is claimed is:

1. A compound represented by Chemical Formula 1:

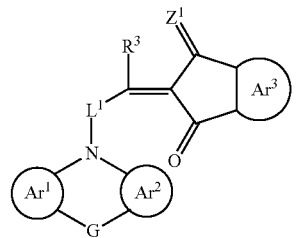

[Chemical Formula 1]

wherein, in Chemical Formula 1, $Ar^1$ to $Ar^3$ are independently one of a substituted or unsubstituted C6 to C30 arylene group, a substituted or unsubstituted C6 to C30 arene group, a substituted or unsubstituted C3 to C30 heterocyclic group, and a combination thereof in a condensed ring, $R^3$ is one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G is one of a single bond, —O—, —S—, —Se—, —N=, —(CR$^f$R$^g$)$_k$—, —NR$^h$—, —SiR$^i$R$^j$—, —GeR$^k$R$^l$—, —(C(R$^m$)=C(R$^n$))—, and SnR$^o$R$^p$ wherein R$^f$, R$^g$, R$^h$, R$^i$, R$^j$, R$^k$, R$^l$, R$^m$, R$^n$, R$^o$ and R$^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, $R^k$ and $R^l$, $R^m$ and $R^n$, and $R^o$ and $R^p$ are independently present or linked with each other to provide a ring, and k is one of 1 and 2, $Z^1$ is one of O or $CR^bR^c$, wherein $R^b$ and $R^c$ are independently one of hydrogen, a substituted or unsubstituted C1 to C10 alkyl group, a cyano group, and a cyano-containing group, provided that at least one of $R^b$ and $R^c$ is a cyano group or a cyano-containing group, and $L^1$ is one of linking groups of Group 1,

[Group 1]

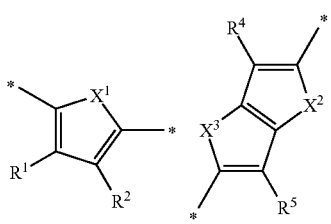

wherein, in Group 1, $X^1$ is one of —Se—, —Te—, —O—, —S(=O)—, —S(=O)$_2$—, —NR$^a$—, —SiR$^b$R$^c$—, and —GeR$^d$R$^e$—, $X^2$ and $X^3$ are independently one of —S—, —Se—, —Te—, —O—, —S(=O)—, —S(=O)$_2$—, —NR$^a$—, —SiR$^b$R$^c$—, and —GeR$^d$R$^e$—, $R^a$ to $R^e$ are independently one of hydrogen and a substituted or unsubstituted C11 to C10 alkyl group, $R^1$, $R^2$, $R^4$, and $R^5$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, and

* is a linking point.

2. The compound of claim 1, wherein $R^3$ is one of hydrogen, deuterium, and a methyl group.

3. The compound of claim 1, wherein at least one of $Ar^1$ and $Ar^2$ is a substituted or unsubstituted C3 to C30 heterocyclic group including at least one hetero atom selected from nitrogen (N), sulfur (S), selenium (Se), and a combination thereof.

4. The compound of claim 3, wherein $R^3$ is one of hydrogen, deuterium, and a methyl group.

5. The compound of claim 1, wherein $Ar^3$ is a condensed ring of a substituted or unsubstituted C6 to C30 arylene group, a substituted or unsubstituted C6 to C30 arene group, and a substituted or unsubstituted C3 to C30 heterocyclic group.

6. The compound of claim 5, wherein $Ar^3$ is a condensed ring of a substituted or unsubstituted phenylene group and a substituted or unsubstituted heterocyclic group including one of S, Se, Ge, and Te.

7. The compound of claim 6, wherein $R^3$ is one of hydrogen, deuterium, and a methyl group.

8. The compound of claim 1, wherein the compound is represented by one of Chemical Formulae 1-A to 1-D4:

[Chemical Formula 1-A]

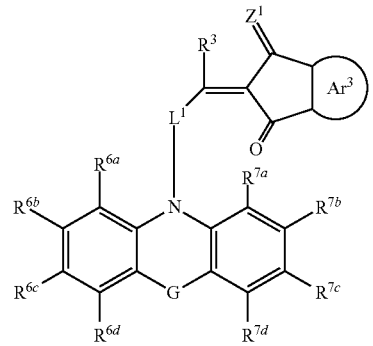

[Chemical Formula 1-B1]

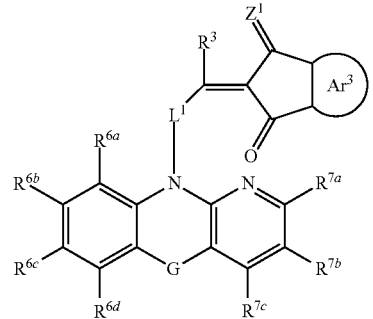

[Chemical Formula 1-B2]

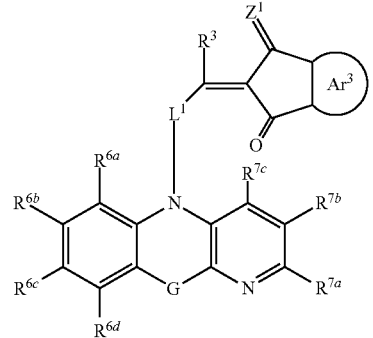

[Chemical Formula 1-C1]

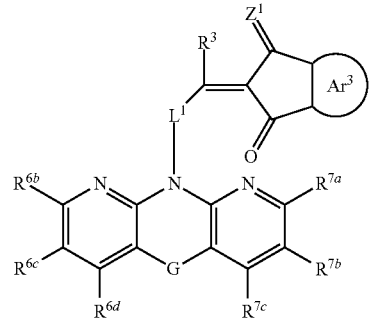

111

-continued

[Chemical Formula 1-C2]

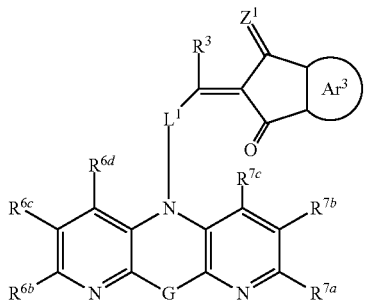

[Chemical Formula 1-D1]

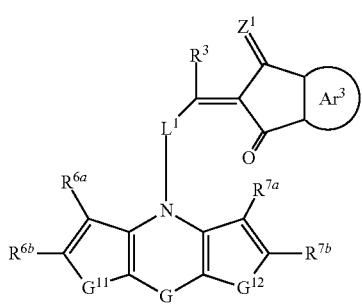

[Chemical Formula 1-D2]

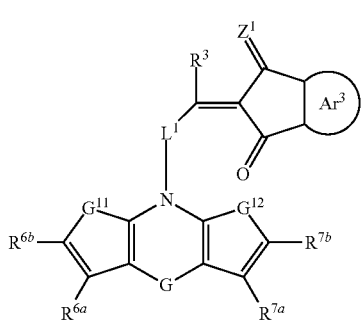

[Chemical Formula 1-D3]

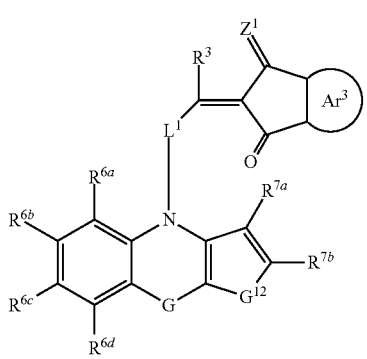

112

-continued

[Chemical Formula 1-D4]

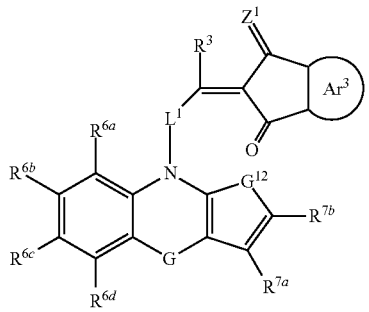

wherein in Chemical Formulae 1-D1 to 1-D4, $G^{11}$ and $G^{12}$ are independently one of —S—, —Se—, —Te—, —GeR$^x$R$^y$—, and —CR$^z$R$^w$—, wherein R$^x$, R$^y$, R$^z$, and R$^w$ are independently one of hydrogen, a halogen, a substituted or unsubstituted C1 to C10 alkyl group, and a substituted or unsubstituted C6 to C10 aryl group, wherein, in Chemical Formulae 1-A to 1-D4, $R^{6a}$ to $R^{6d}$ and $R^{7a}$ to $R^{7d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ are independently present or two adjacent groups thereof are linked with each other to provide a fused cycle, and $R^{7a}$ to $R^{7d}$ are independently present or two adjacent groups thereof are linked with each other to provide a fused cycle.

9. The compound of claim 1, wherein the compound is represented by one of Chemical Formulae 1-E to 1-G:

[Chemical Formula 1-E]

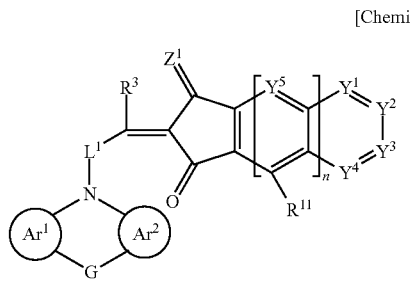

[Chemical Formula 1-F]

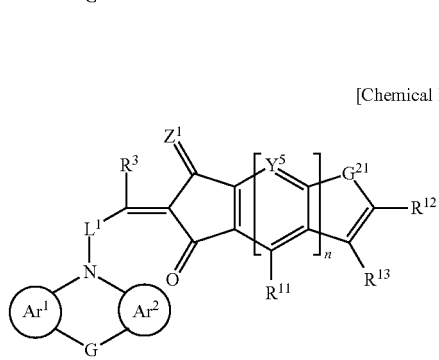

113
-continued

[Chemical Formula 1-G]

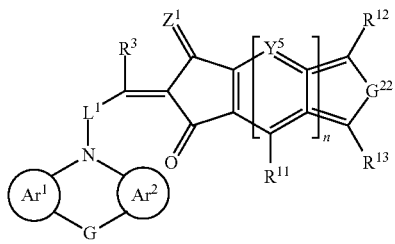

wherein, in Chemical Formulae 1-E to 1-0, $Y^1$ to $Y^5$ are independently one of N and $CR^d$, wherein $R^d$ is one of hydrogen and a substituted or unsubstituted C1 to C10 alkyl group, $R^{11}$ to $R^{13}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, n is 0 or 1, and $G^{21}$ and $G^{22}$ are independently one of —S—, —Se—, —$GeR^xR^y$—, and —Te—, wherein $R^x$ and $R^y$ are independently one of hydrogen, a halogen, a substituted or unsubstituted C1 to C10 alkyl group, and a substituted or unsubstituted C6 to C10 aryl group.

10. The compound of claim 9, wherein at least one of $Y^1$ to $Y^4$ is N.

11. The compound of claim 9, wherein at least one of $Ar^1$ and $Ar^2$ is a C3 to C30 heteroarylene group including at least one hetero atom selected from nitrogen (N), sulfur (S), selenium (Se), and a combination thereof.

12. The compound of claim 9, wherein $R^3$ is one of hydrogen, deuterium, and a methyl group.

13. The compound of claim 1, wherein the compound is represented by one of Chemical Formulae 1-H to 1-S4:

[Chemical Formula 1-H]

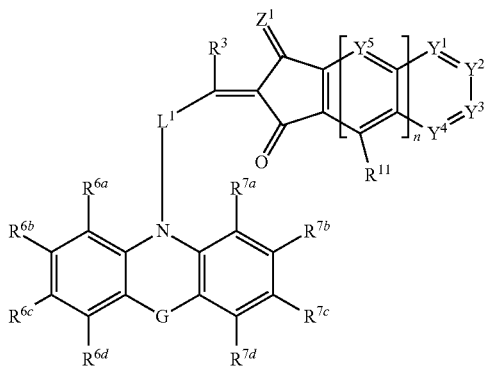

114
-continued

[Chemical Formula 1-I]

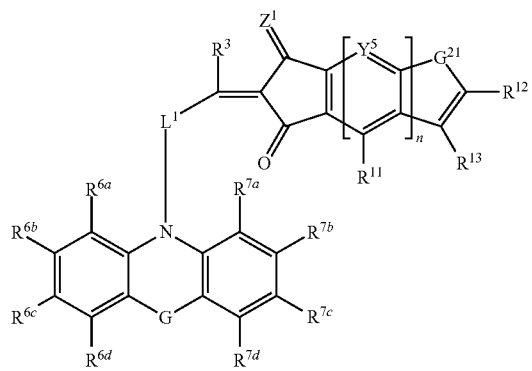

[Chemical Formula 1-J]

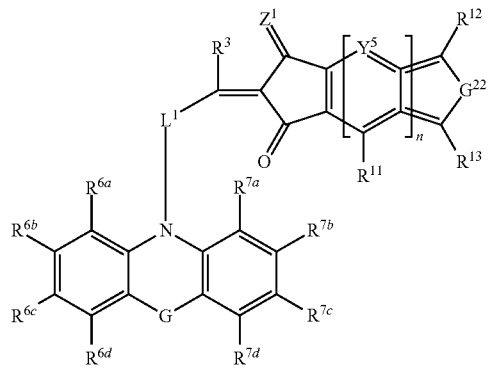

[Chemical Formula 1-K1]

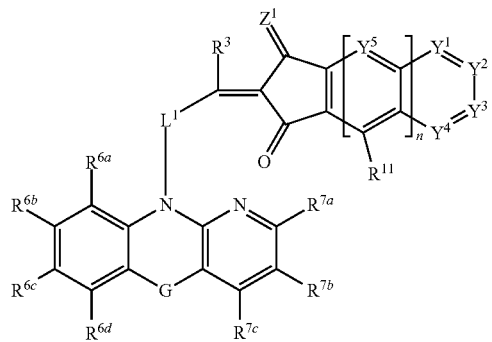

[Chemical Formula 1-L1]

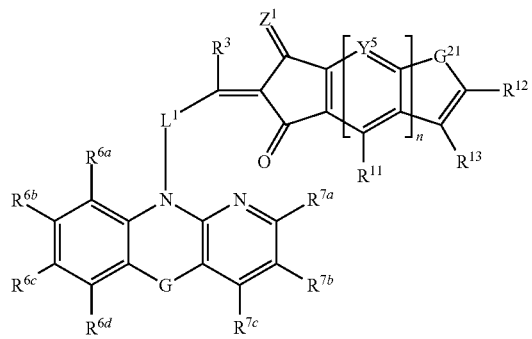

[Chemical Formula 1-M1]
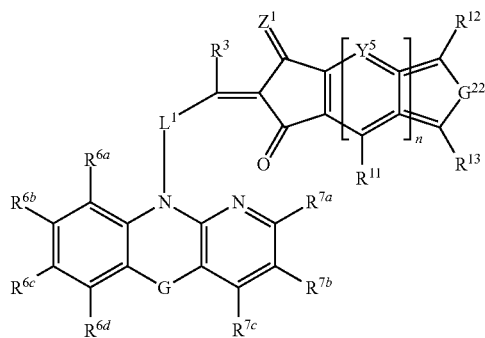
[Chemical Formula 1-K2]
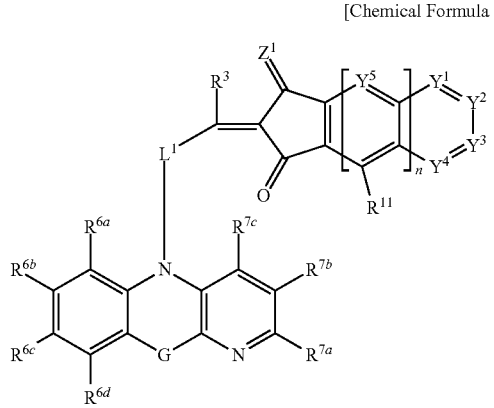
[Chemical Formula 1-L2]
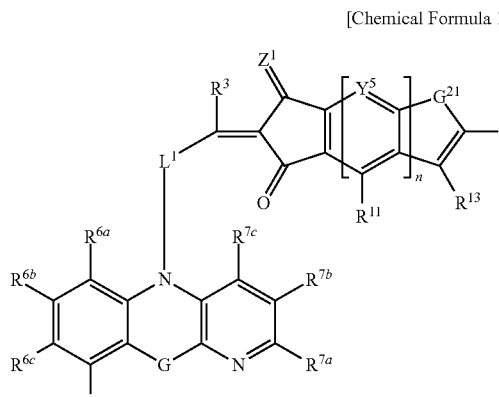
[Chemical Formula 1-M2]
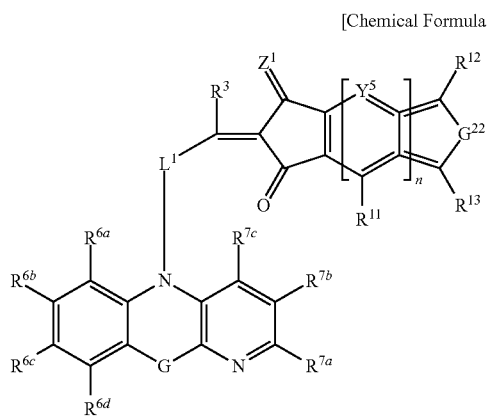
[Chemical Formula 1-N1]
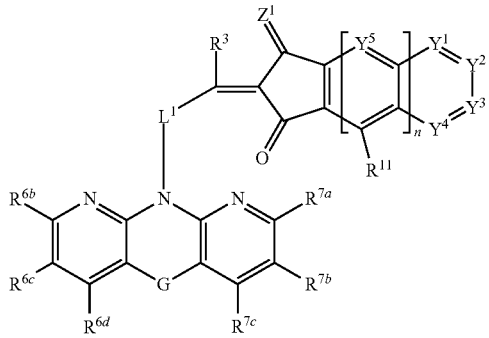
[Chemical Formula 1-O1]
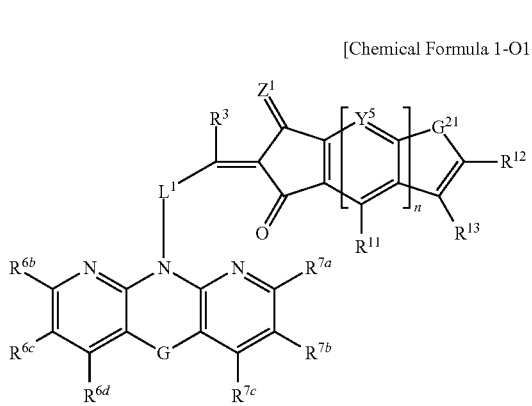
[Chemical Formula 1-P1]
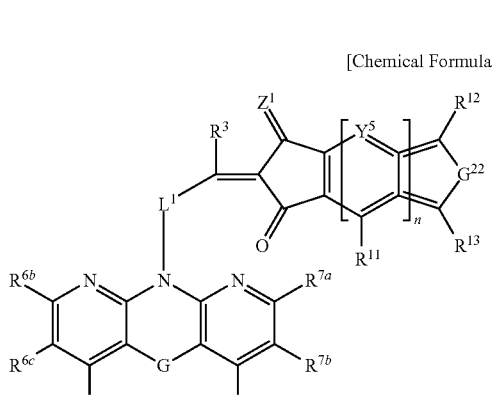
[Chemical Formula 1-N2]
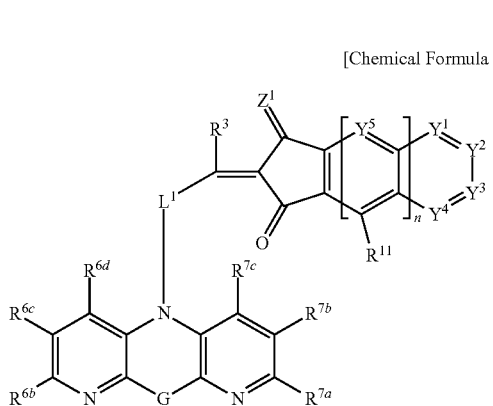

[Chemical Formula 1-O2]
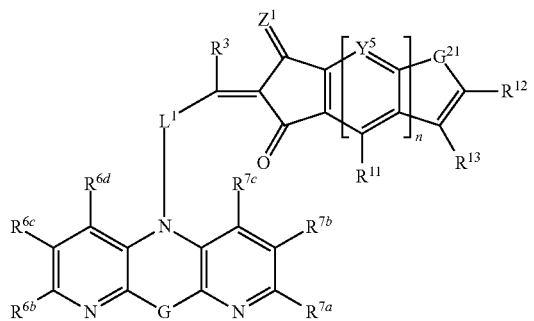
[Chemical Formula 1-S1]
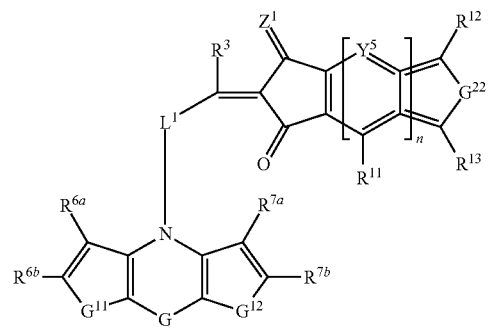
[Chemical Formula 1-P2]
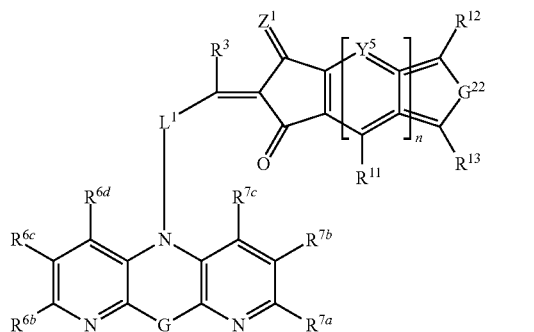
[Chemical Formula 1-Q2]
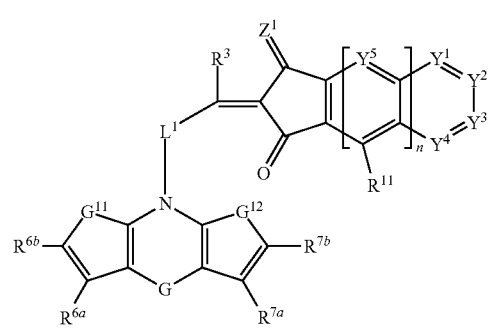
[Chemical Formula 1-Q1]
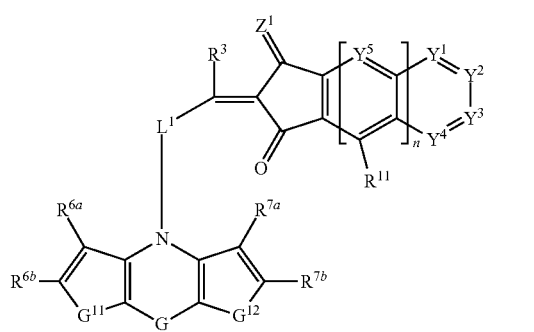
[Chemical Formula 1-R2]
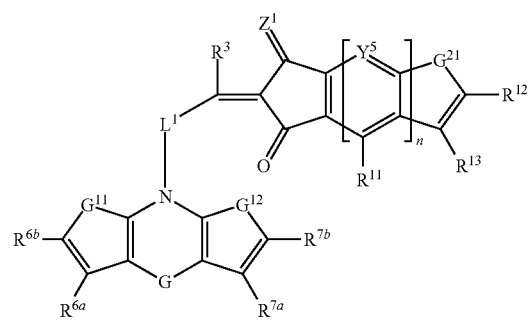
[Chemical Formula 1-R1]
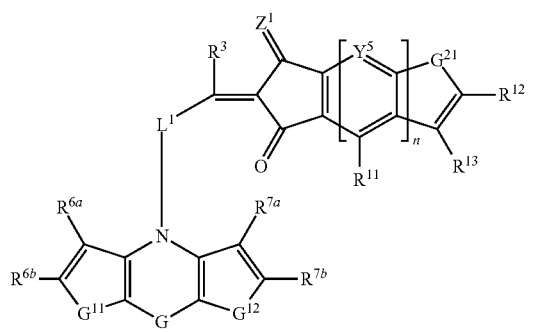
[Chemical Formula 1-S2]
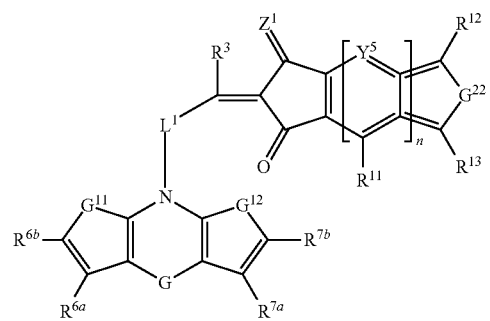

-continued

[Chemical Formula 1-Q3]

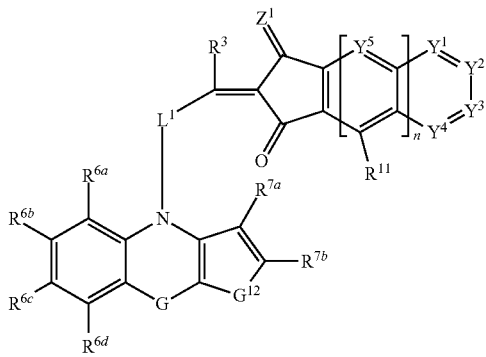

[Chemical Formula 1-R3]

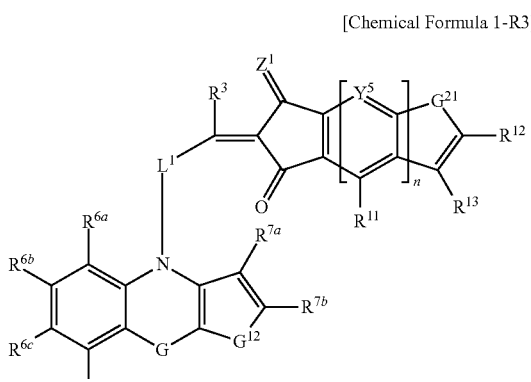

[Chemical Formula 1-S3]

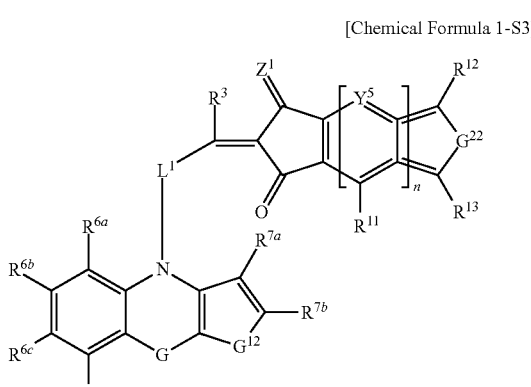

[Chemical Formula 1-Q4]

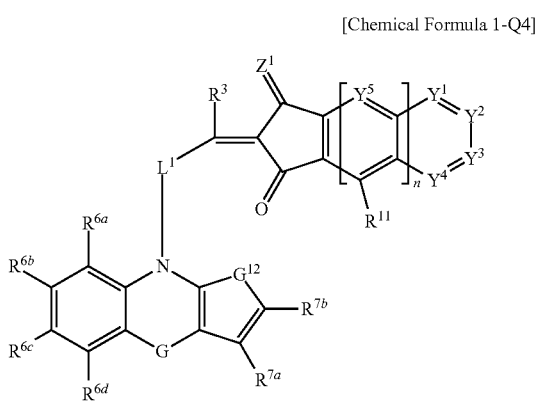

-continued

[Chemical Formula 1-R4]

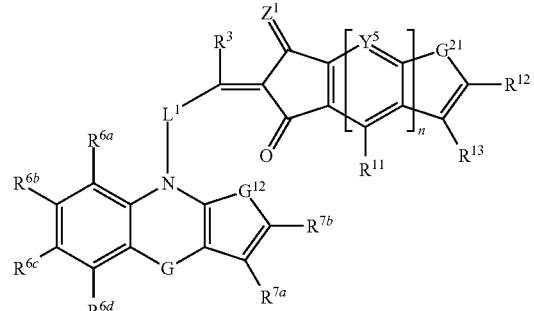

[Chemical Formula 1-S4]

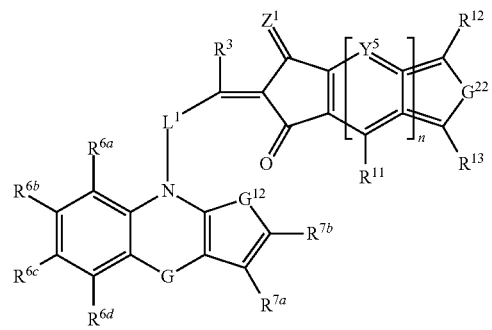

wherein, in Chemical Formulae 1-H to 1-S4, $G^{11}$ and $G^{12}$ are independently one of —S—, —Se—, —Te—, —GeR$^x$R$^y$—, and —CR$^z$R$^w$—, wherein R$^x$, R$^y$, R$^z$, and R$^w$ are independently one of hydrogen, a halogen, a substituted or unsubstituted C1 to C10 alkyl group, and a substituted or unsubstituted C6 to C10 aryl group, $R^{6a}$ to $R^{6d}$ and $R^{7a}$ to $R^{7d}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ to $R^{6d}$ are independently present or two adjacent groups thereof are linked with each other to provide a fused cycle, $R^{7a}$ to $R^{7d}$ are independently present or two adjacent groups thereof are linked with each other to provide a fused cycle, $Y^1$ to $Y^5$ are independently one of N and CR$^d$, wherein R$^d$ is one of hydrogen and a substituted or unsubstituted C1 to C10 alkyl group, $R^{11}$ to $R^{13}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, n is one of 0 and 0.1, and $G^{21}$ and $G^{22}$ are independently one of —S—, —Se—, —GeR$^x$R$^y$—, and —Te—, wherein R$^x$ and R$^y$ are independently one of hydrogen, a halogen, a substituted or unsubstituted C1 to C10 alkyl group, and a substituted or unsubstituted C6 to C10 aryl group.

14. The compound of claim 13, wherein $R^3$ is one of hydrogen, deuterium, and a methyl group.

15. The compound of claim 1, wherein the compound is represented by Chemical Formula 1-T:

[Chemical Formula 1-T]

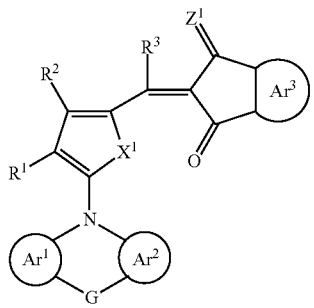

wherein, in Chemical Formula 1-T,
$Ar^3$ is a substituted or unsubstituted C6 to C30 arylene group, a substituted or unsubstituted C6 to C30 arene group, a substituted or unsubstituted C3 to C30 heterocyclic group including at least one hetero atom selected from S, Se, Te, Ge, N, and a combination thereof, and a combination thereof in a condensed ring.

16. The compound of claim 1, wherein the compound is represented by Chemical Formula 1-U:

[Chemical Formula 1-U]

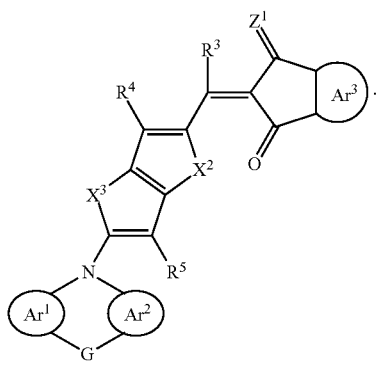

17. The compound of claim 1, wherein the compound is represented Chemical Formula 1-V:

[Chemical Formula 1-V]

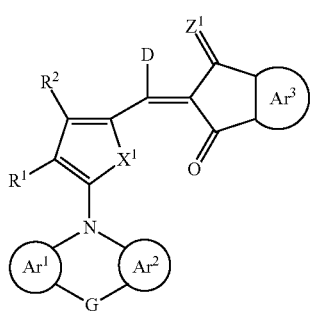

wherein, in Chemical Formula 1-V,
D is deuterium.

18. The compound of claim 1, wherein the compound is represented by Chemical Formula 1-W:

[Chemical Formula 1-W]

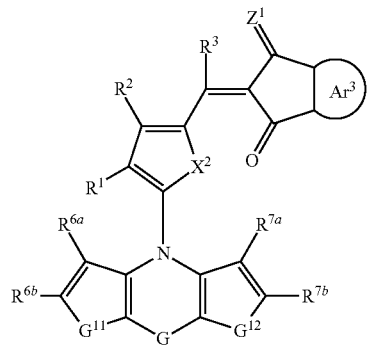

wherein, in Chemical Formula 1-W,
$G^{11}$ and $G^{12}$ are independently one of —S—, —Se—, —Te—, —GeR$^x$R$^y$—, and —CR$^z$R$^w$—, wherein $R^x$, $R^y$, $R^z$, and $R^w$ are independently one of hydrogen, a halogen, a substituted or unsubstituted C1 to C10 alkyl group, and a substituted or unsubstituted C6 to C10 aryl group, $R^{6a}$ and $R^{6b}$ and $R^{7a}$ and $R^{7b}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, $R^{6a}$ and $R^{6b}$ are independently present or linked with each other to provide a fused cycle, and $R^{7a}$ and $R^{7b}$ are independently present or linked with each other to provide a fused cycle.

19. The compound of claim 1, wherein the compound has a maximum absorption wavelength ($\lambda_{max}$) of greater than or equal to about 510 nm and less than or equal to about 565 nm in a thin film state.

20. A photoelectric device comprising:
a first electrode and a second electrode facing each other, and
an organic layer between the first electrode and the second electrode
wherein the organic layer includes the compound of claim 1.

21. The photoelectric device of claim 20, wherein
the organic layer includes an active layer,
the active layer includes a p-type semiconductor and an n-type semiconductor, and
the compound is in the active layer.

22. The photoelectric device of claim 21, wherein the active layer has a maximum absorption wavelength of greater than or equal to about 510 nm and less than or equal to about 565 nm.

23. An image sensor comprising:
the photoelectric device of claim 20.

24. The image sensor of claim 23, further comprising:
a semiconductor substrate;
a first photo-sensing device; and
a second photo-sensing device, wherein
the semiconductor substrate is integrated with the first photo-sensing device and the second photo-sensing device,
the first photo-sensing device is configured to sense light in a blue wavelength region, the second photo-sensing device is configured to sense light in a red wavelength region, the photoelectric device is on the semiconductor substrate, and the photoelectric device is configured to selectively sensing light in a green wavelength region.

25. The image sensor of claim 24, further comprising:

a color filter layer over the first photo-sensing device and the second photo-sensing device, wherein the color filter layer includes a blue filter overlapping the first photo-sensing device and a red filter overlapping the second photo-sensing device.

26. The image sensor of claim 24, wherein the first photo-sensing device and the second photo-sensing device are stacked in a vertical direction in the semiconductor substrate.

27. The image sensor of claim 24, wherein the photoelectric device is a green photoelectric device configured to sense light in a green wavelength region;

the first photo-sensing device and the second photo-sensing device are a blue photoelectric device configured to sense light in a blue wavelength region, and a red photoelectric device configured to sense light in a red wavelength region, respectively, and the green photoelectric device, the blue photoelectric device, and the red photoelectric device are stacked.

28. An electronic device comprising the image sensor of claim 23.

29. An electronic device comprising the photoelectric device of claim 20.

30. A compound comprising:

a structure represented by one of Chemical Formulae 1-T to 1-W:

[Chemical Formula 1-T]

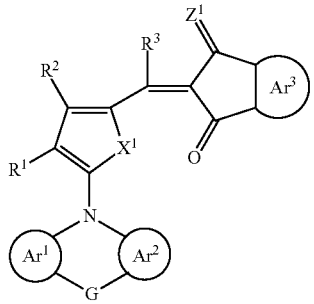

[Chemical Formula 1-U]

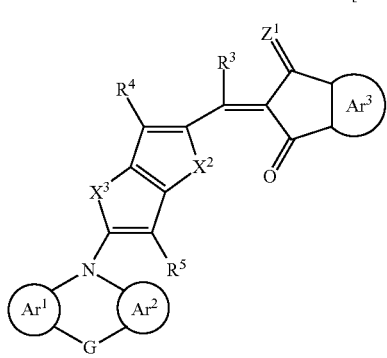

[Chemical Formula 1-V]

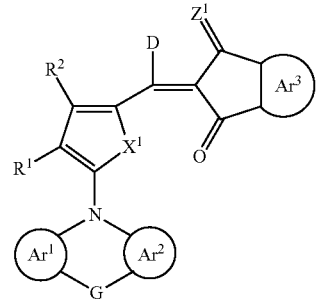

[Chemical Formula 1-W]

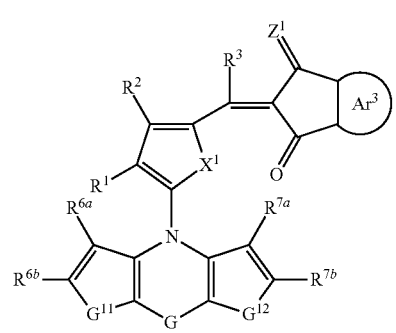

wherein in Chemical Formulae 1-T to 1-W, $Ar^1$ to $Ar^3$ are independently one of a substituted or unsubstituted C6 to C30 arylene group, a substituted or unsubstituted C6 to C30 arene group, a substituted or unsubstituted C3 to C30 heterocyclic group, and a combination thereof in a condensed ring, D is deuterium, $R^1$, $R^2$, $R^3$, $R^4$, and $R^5$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G is one of a single bond, —O—, —S—, —Se—, —N=, —$(CR^fR^g)_k$—, —$NR^h$—, —$SiR^iR^j$—, —$GeR^kR^l$—, —$(C(R^m)=C(R^n))$—, and $SnR^oR^p$ wherein $R^f$, $R^g$, $R^h$, $R^i$, $R^j$, $R^k$, $R^l$, $R^m$, $R^n$, $R^o$ and $R^p$ are independently one of hydrogen, a halogen, a substituted or unsubstituted C1 to C10 alkyl group, a substituted or unsubstituted C1 to C10 alkoxy group, and a substituted or unsubstituted C6 to C12 aryl group, and $R^i$ and $R^j$, $R^k$ and $R^l$, $R^m$ and $R^n$, and $R^o$ and $R^p$ are independently present or linked with each other to provide a ring, and k is one of 1 and 2, $Z^1$ is one of O or $CR^bR^c$, wherein $R^b$ and $R^c$ are independently one of hydrogen, a substituted or unsubstituted C1 to C10 alkyl group, a cyano group, and a cyano-containing group, provided that at least one of $R^b$ and $R^c$ is a cyano group or a cyano-containing group, and $X^1$ is one of —Se—, —Te—, —O—, —S(=O)—, —$S(=O)_2$—, —$NR^a$—, —$SiR^bR^c$—, and —$GeR^dR^e$—, $X^2$ and $X^3$ are independently one of —S—, —Se—, —Te—, —O—, —S(=O)—, —$S(=O)_2$—, —$NR^a$—, —$SiR^bR^c$—, and —$GeR^dR^e$—, $R^a$ to $R^e$ are independently one of hydrogen and a substituted or unsubstituted C1 to C10 alkyl group, $G^{11}$ and $G^{12}$ are independently one of —S—, —Se—, —Te—, —GeR$^x$R$^y$—, and —CR$^z$R$^w$—, wherein R$^x$, R$^y$, R$^z$, and R$^w$ are independently one of hydrogen, a halogen, a substituted or unsubstituted C1 to C10 alkyl group, and a substituted or unsubstituted C6 to C10 aryl group, R$^{6a}$ and R$^{6b}$ and R$^{7a}$ and R$^{7b}$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, R$^{6a}$ to R$^{6d}$ are independently present or two adjacent groups thereof are linked with each other to provide a fused cycle, and R$^{7a}$ to R$^{7d}$ are independently present or two adjacent groups thereof are linked with each other to provide a fused cycle, and

* is a linking point.

31. The compound of claim 30, wherein the structure is represented by one of the groups listed in Group 3:

[Group 3]

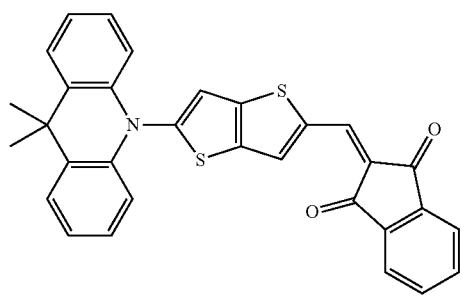

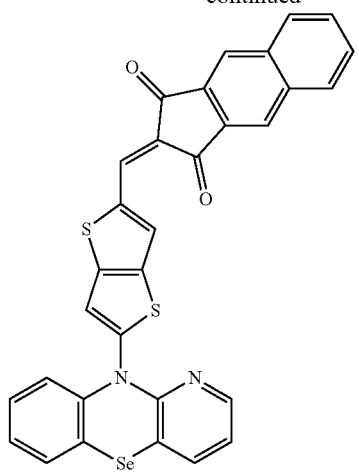

-continued

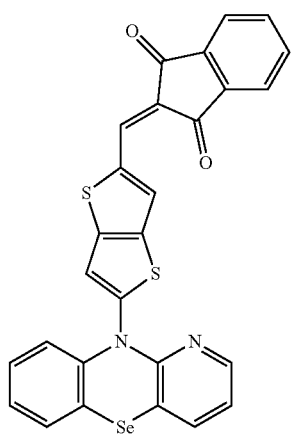

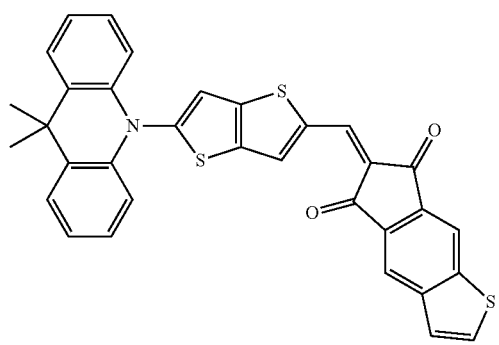

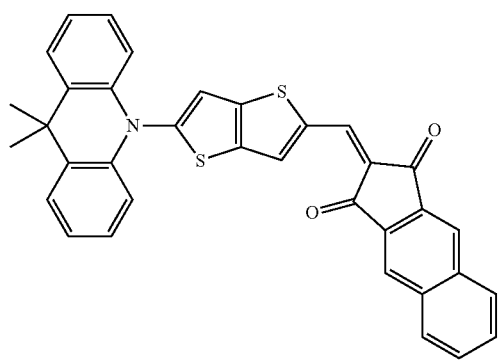

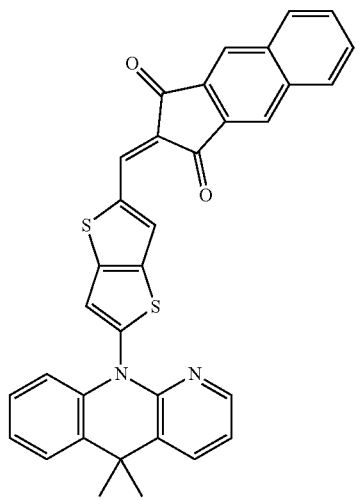

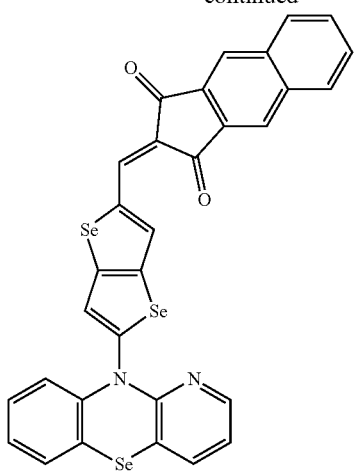
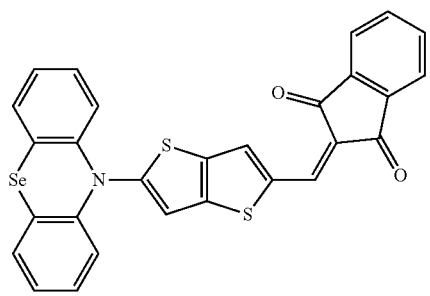
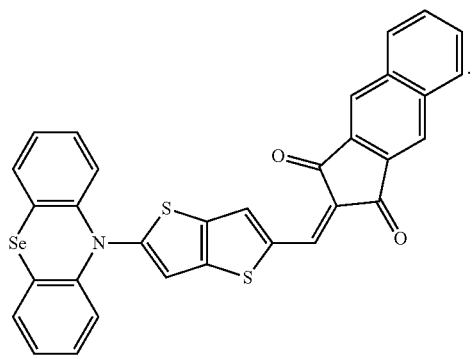
32. The compound of claim 30, wherein the structure is represented by one of the groups listed in Group 4:
[Group 4]
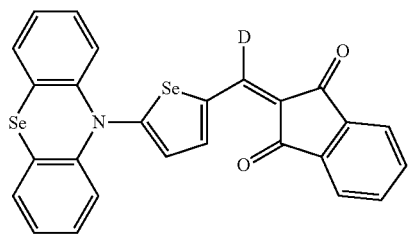
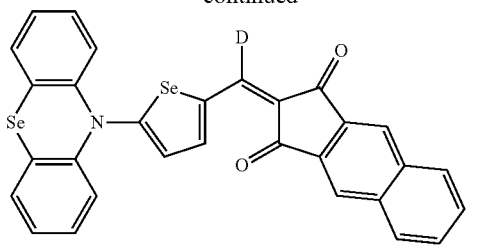
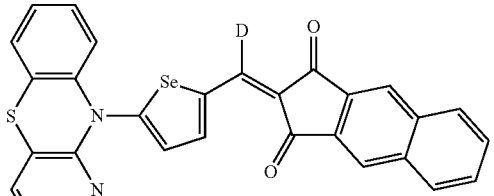
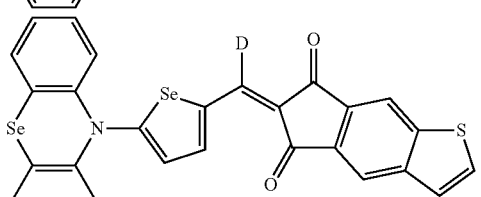
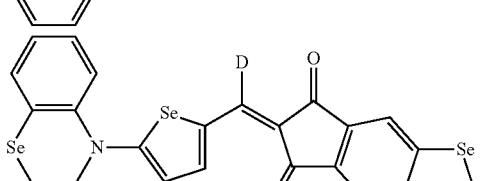
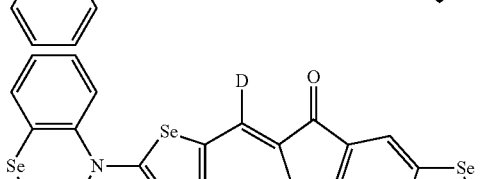
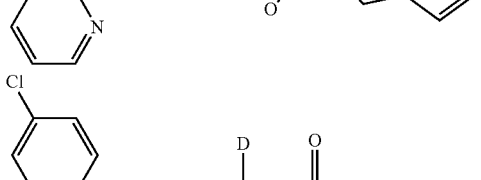
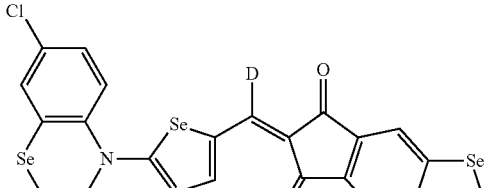

-continued
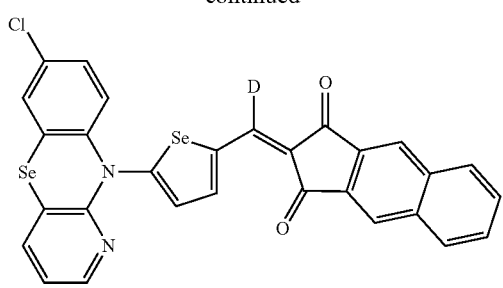
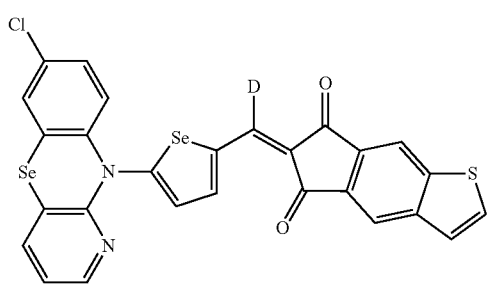
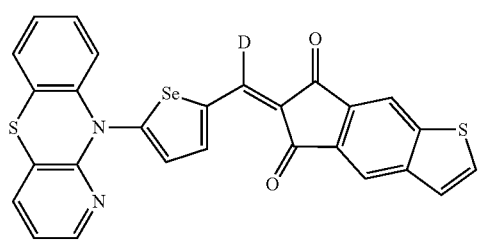
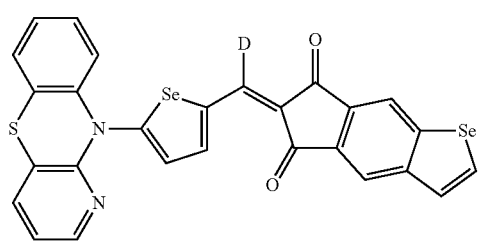
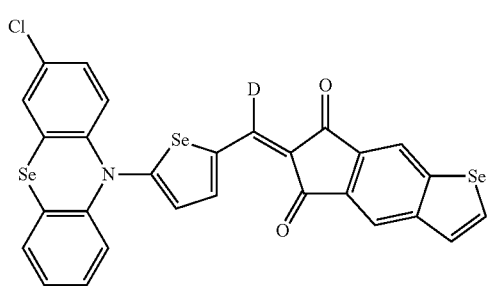
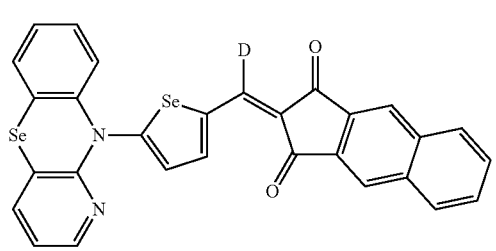
-continued
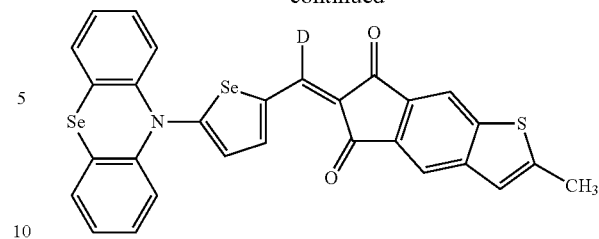
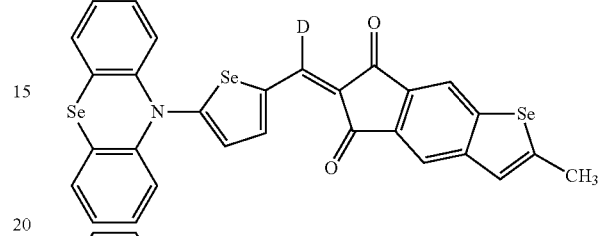
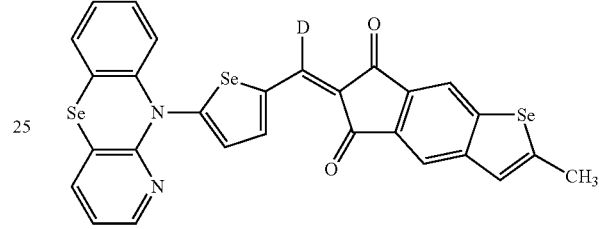
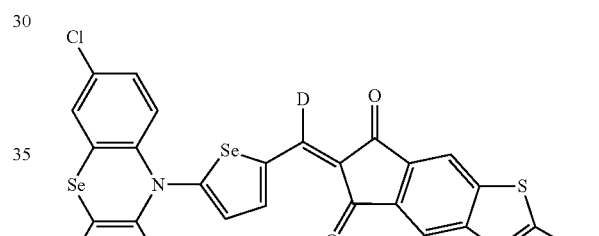
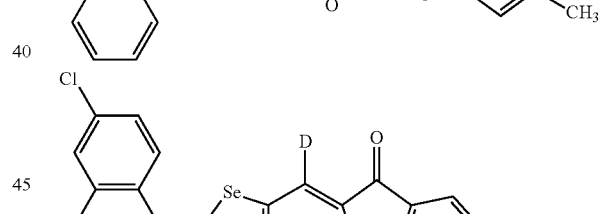
33. The compound of claim 30 wherein the structure is represented by one of the groups listed in Group 5:
[Group 5]
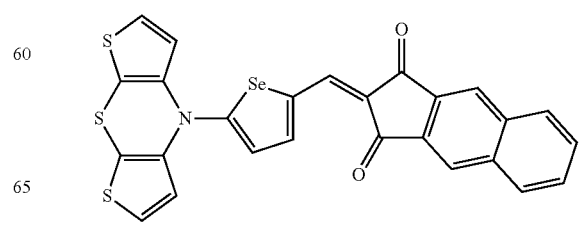

131
-continued
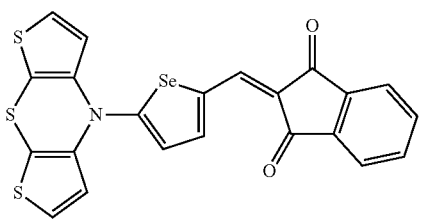
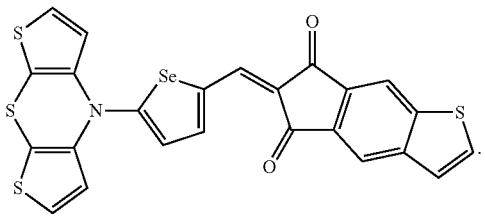
34. The compound of claim 30, wherein the structure is represented by one of the groups listed in Group 2:
[Group 2]
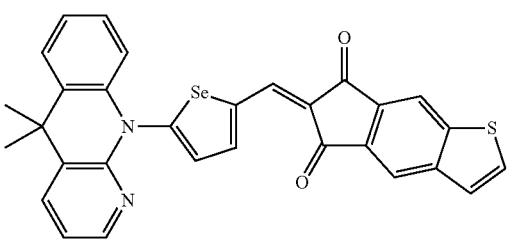
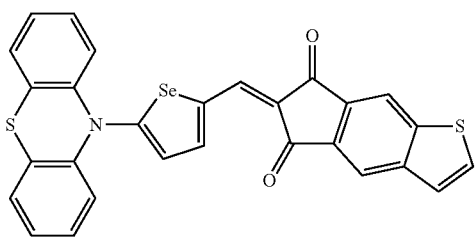
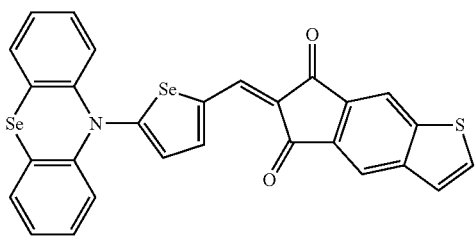
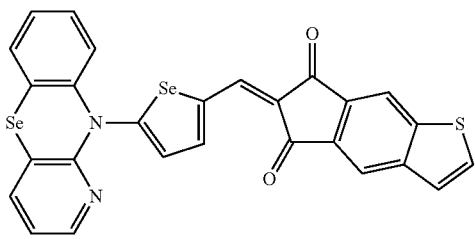
132
-continued
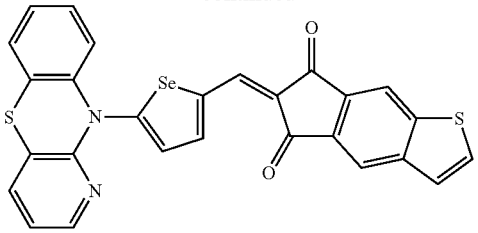
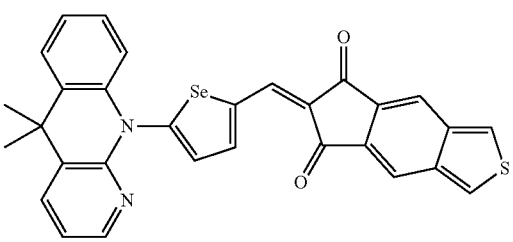
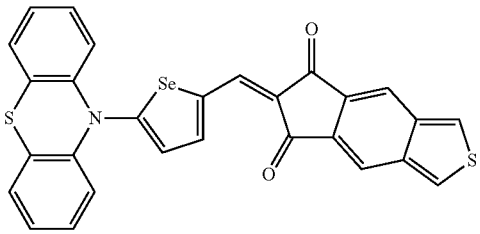
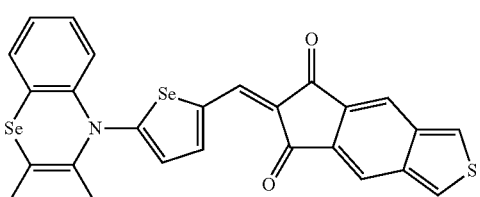
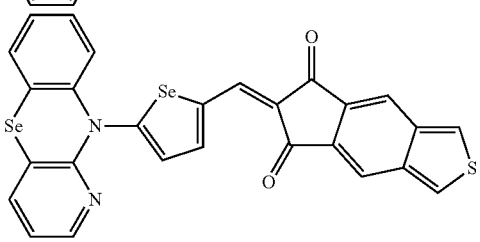
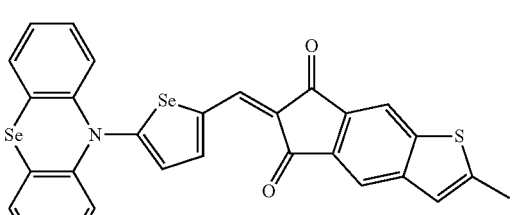
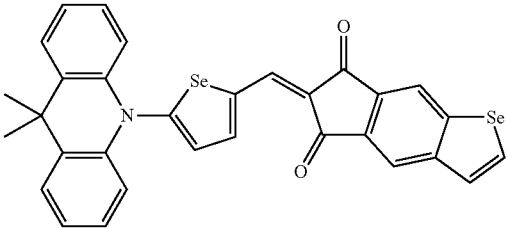

133
-continued
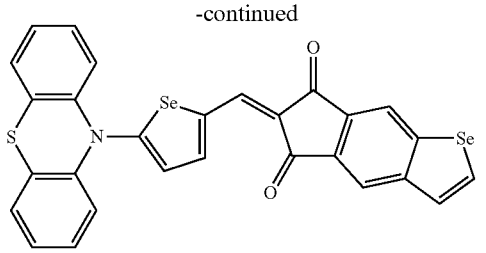
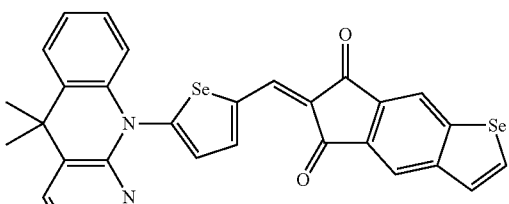
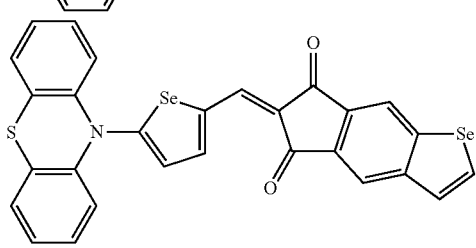
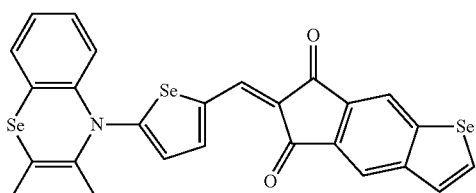
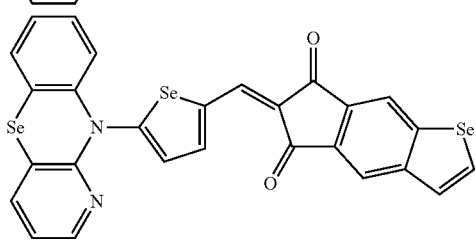
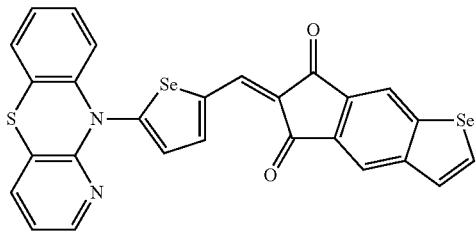
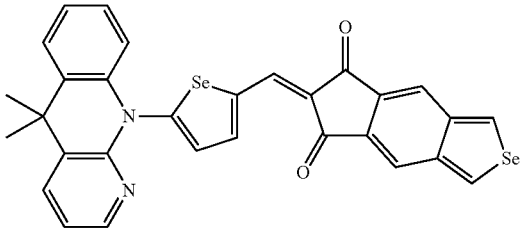
134
-continued
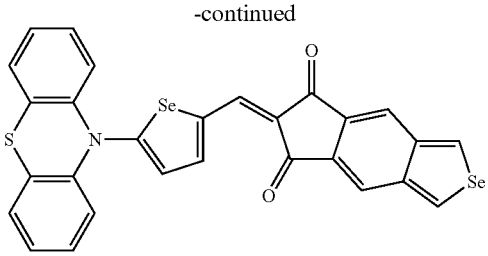
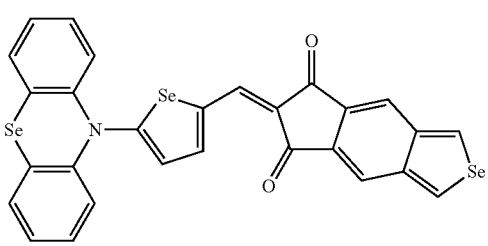
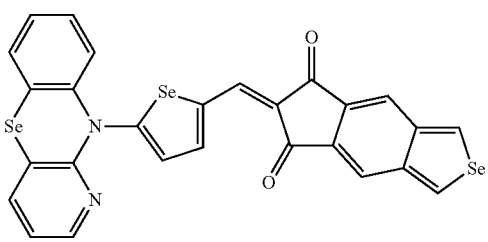
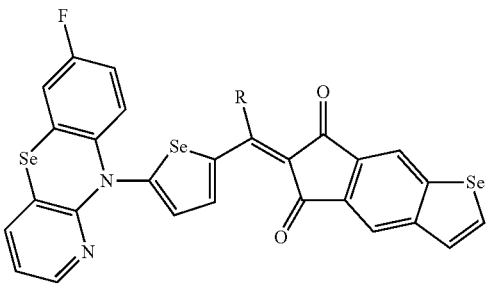
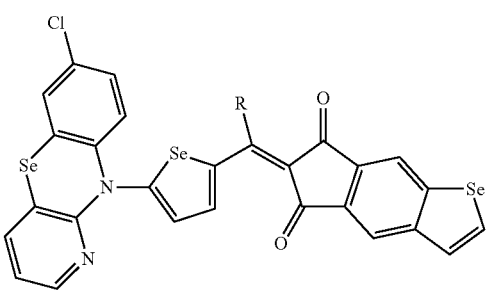
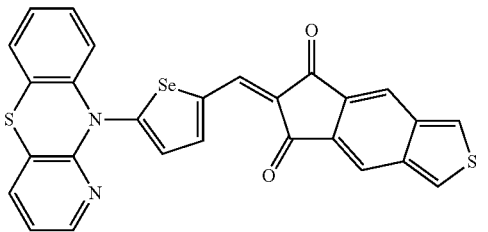

135
-continued
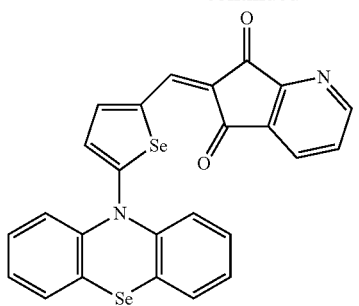
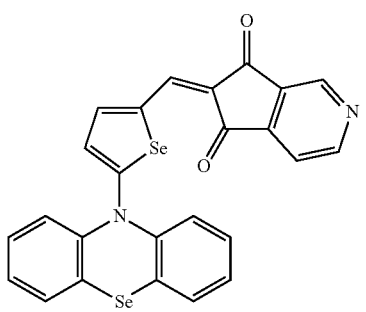
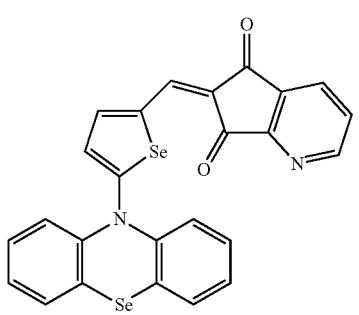
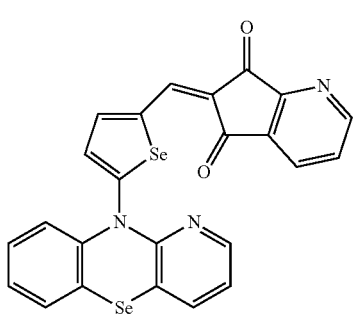
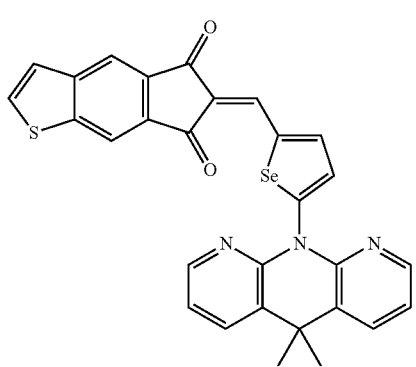
136
-continued
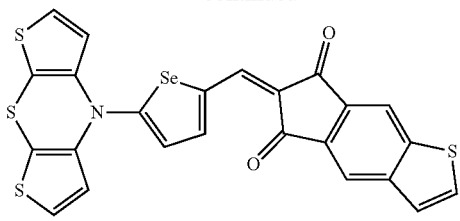
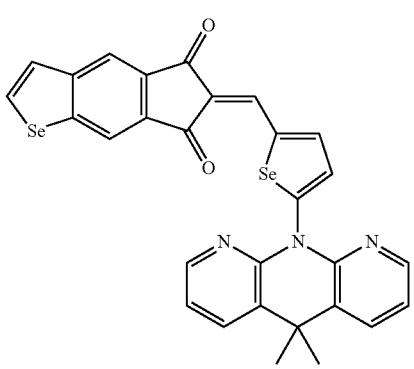
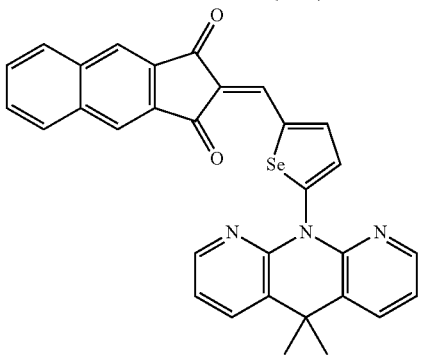
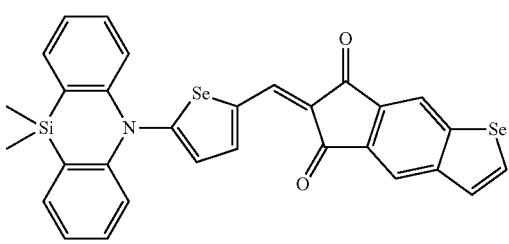
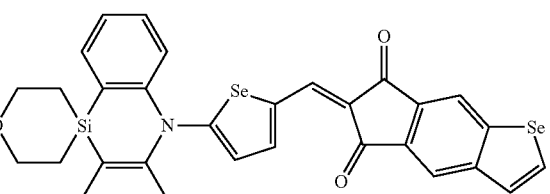
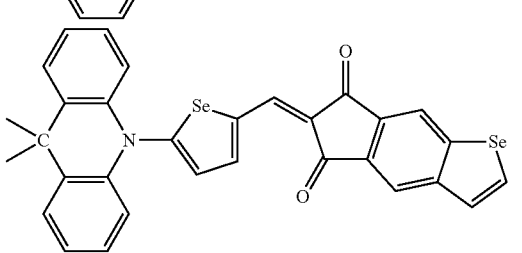

137
-continued
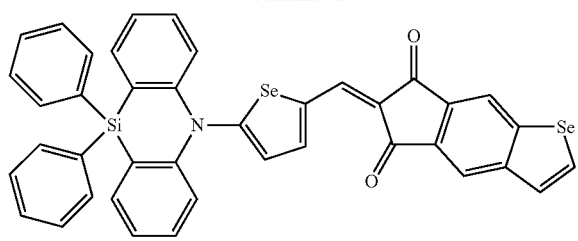
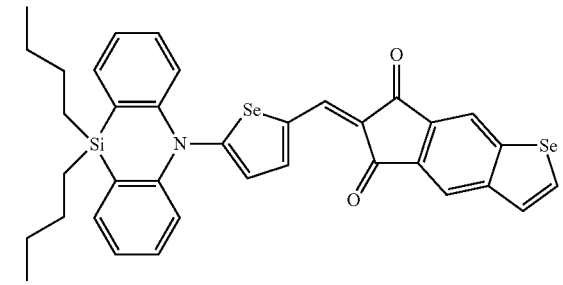
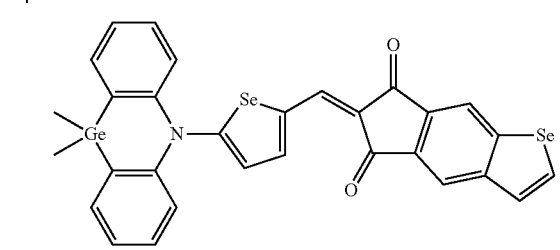
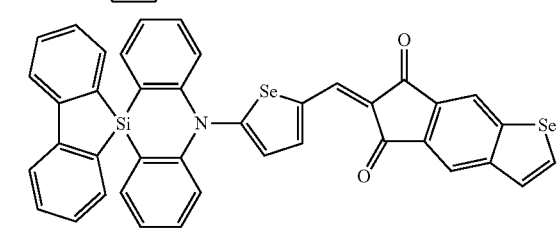
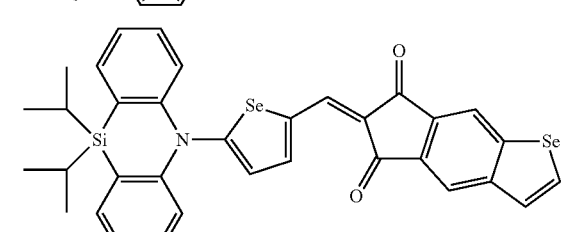
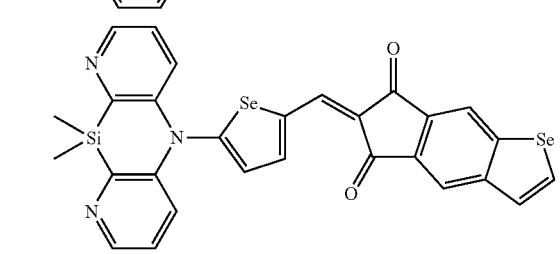
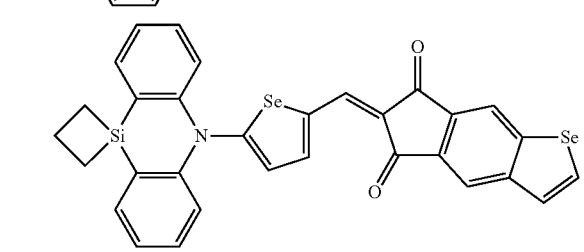
138
-continued
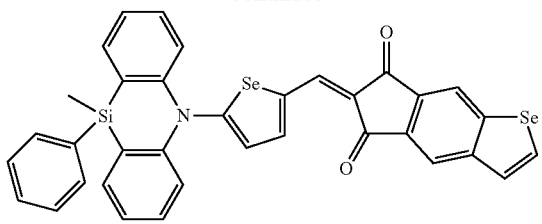
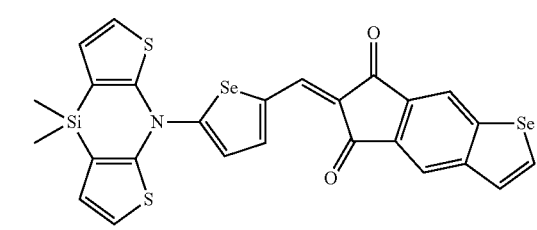
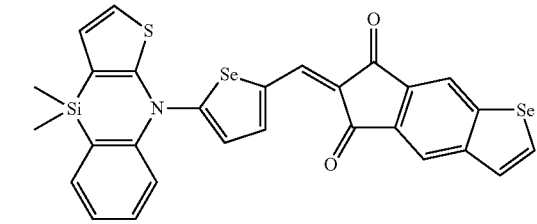
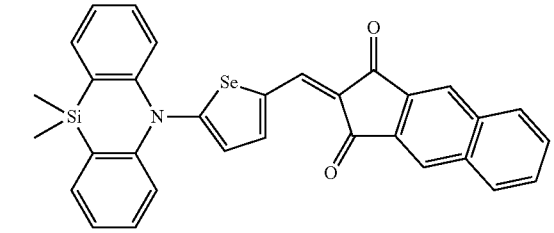
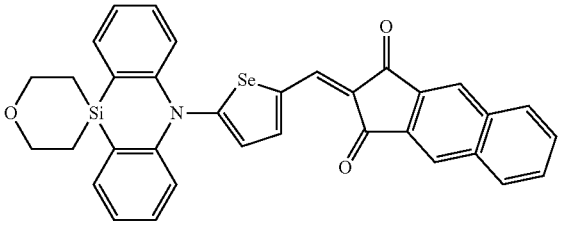
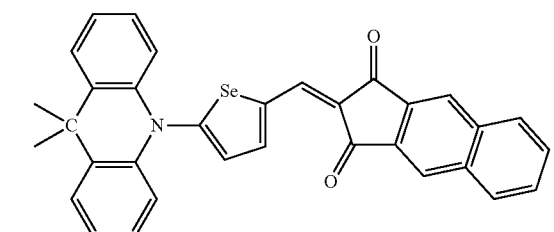
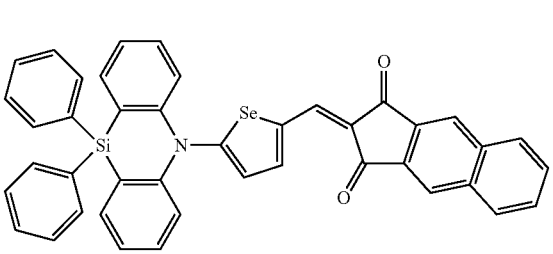

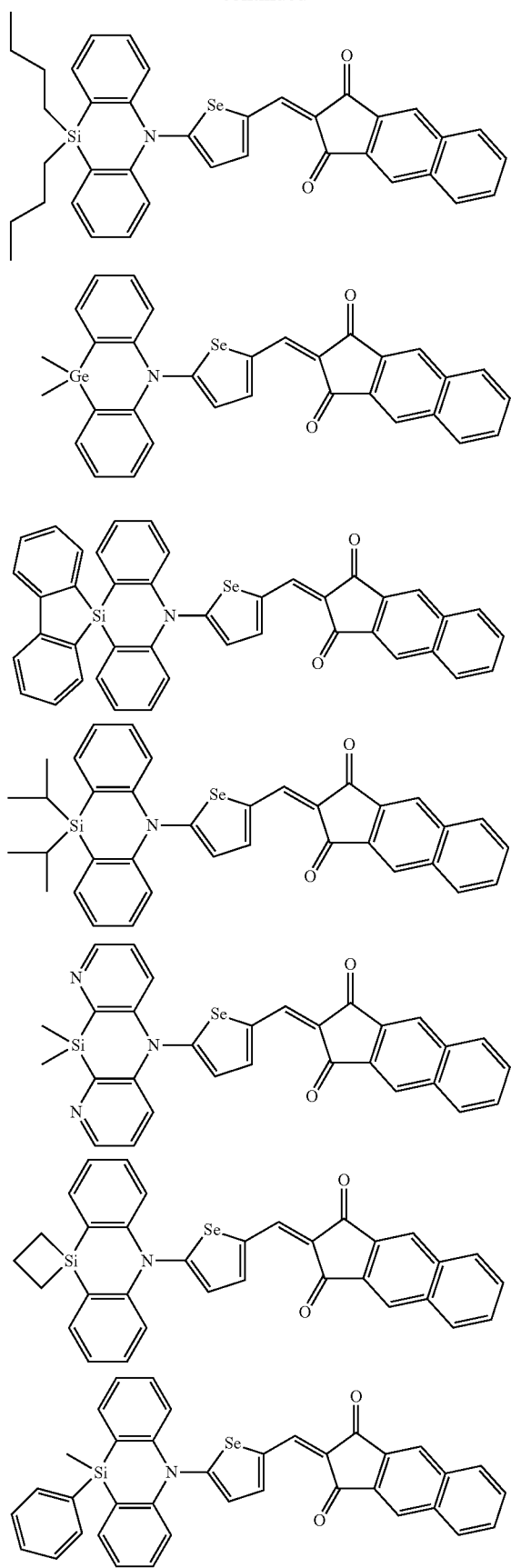
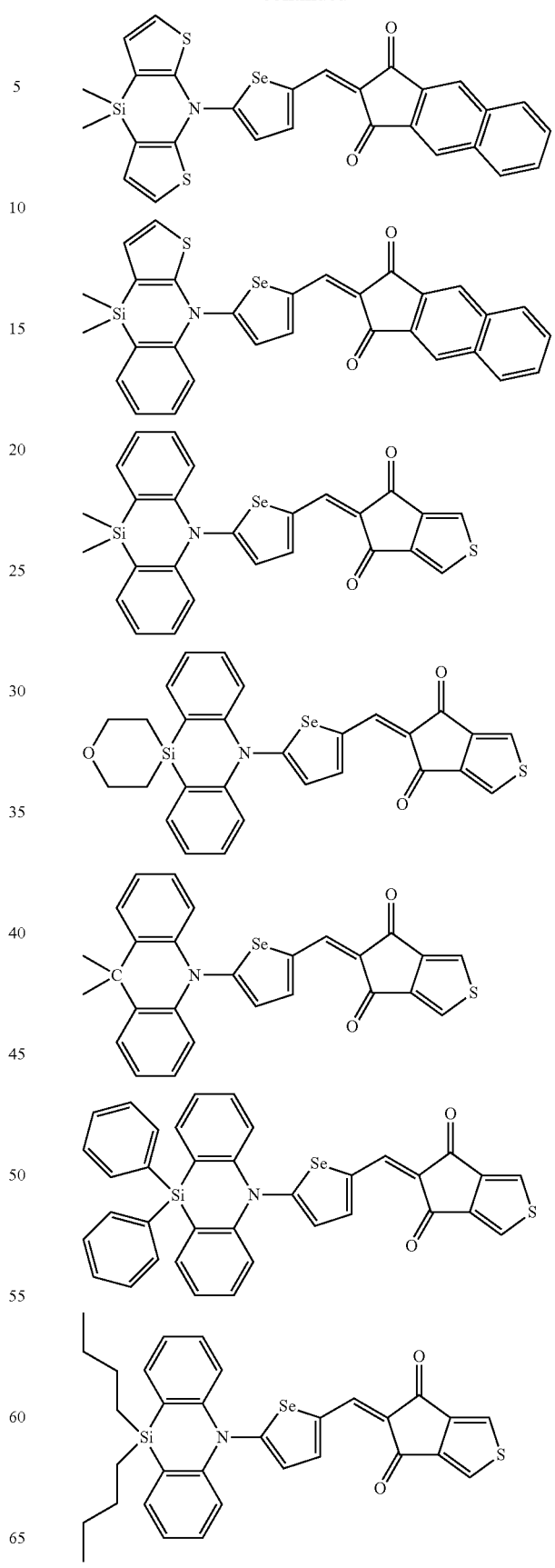

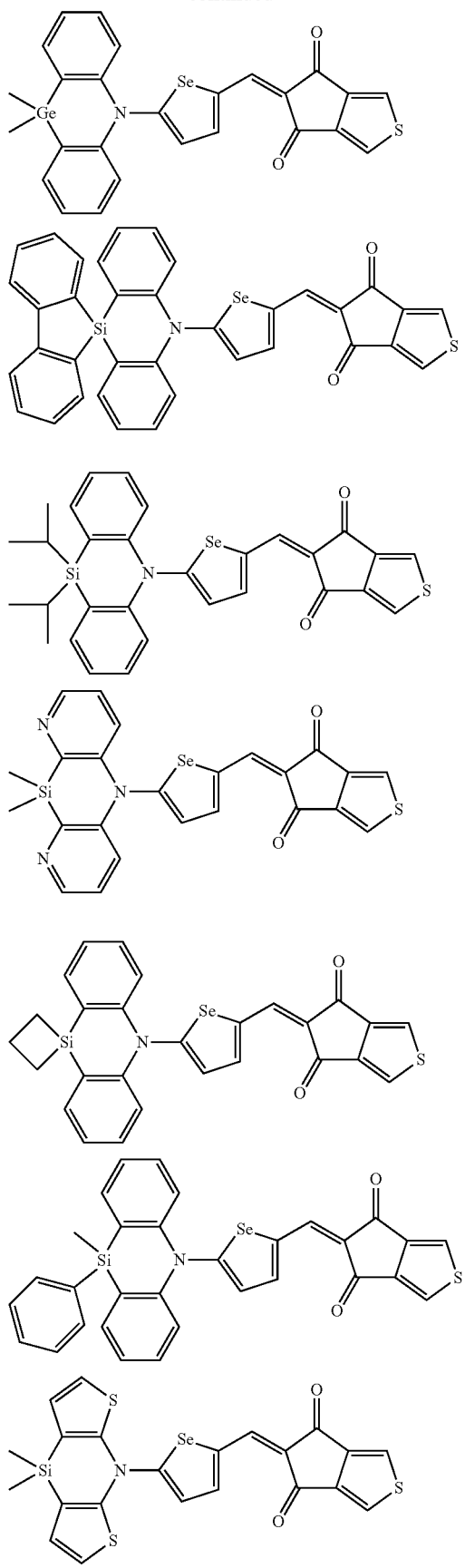
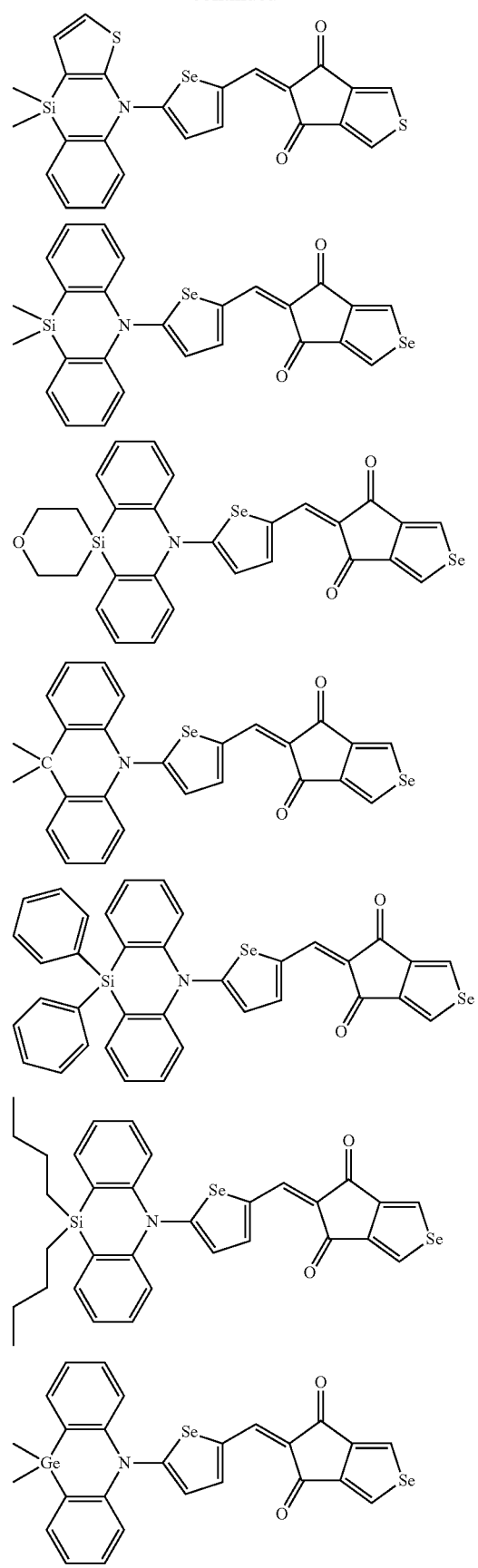

143
-continued
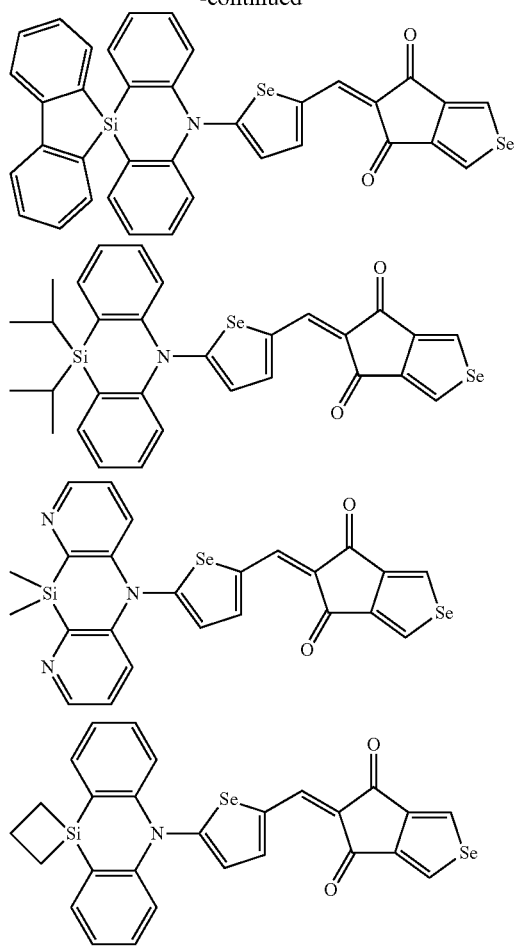
144
-continued
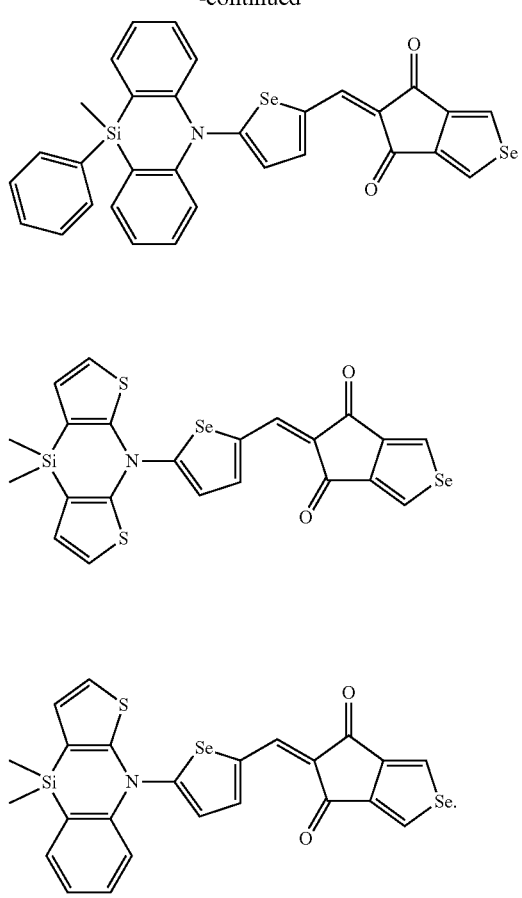
* * * * *